(12) United States Patent
Vale et al.

(10) Patent No.: US 12,268,476 B2
(45) Date of Patent: Apr. 8, 2025

(54) METHOD AND APPARATUS FOR MANAGING ACUTE ISCHEMIC EVENTS

(71) Applicant: NEURAVI LIMITED, Galway (IE)

(72) Inventors: David Vale, Galway (IE); Brendan Casey, Galway (IE); Mahmood Mirza, Galway (IE); Ray McCarthy, Galway (IE); Patrick Connolly, Galway (IE)

(73) Assignee: NEURAVI LIMITED, Galway (IE)

( * ) Notice: Subject to any disclaimer, the term of this patent is extended or adjusted under 35 U.S.C. 154(b) by 868 days.

(21) Appl. No.: 17/268,209

(22) PCT Filed: Aug. 23, 2019

(86) PCT No.: PCT/IB2019/000942
§ 371 (c)(1),
(2) Date: Feb. 12, 2021

(87) PCT Pub. No.: WO2020/039258
PCT Pub. Date: Feb. 27, 2020

(65) Prior Publication Data
US 2021/0315599 A1 Oct. 14, 2021

Related U.S. Application Data

(60) Provisional application No. 62/844,559, filed on May 7, 2019, provisional application No. 62/785,566, filed
(Continued)

(51) Int. Cl.
*A61B 17/221* (2006.01)
*A61B 5/00* (2006.01)
(Continued)

(52) U.S. Cl.
CPC ........ *A61B 5/02007* (2013.01); *A61B 5/0035* (2013.01); *A61B 5/0036* (2018.08);
(Continued)

(58) Field of Classification Search
CPC ... A61B 5/0033; A61B 5/0035; A61B 5/0036; A61B 5/02007; A61B 5/026;
(Continued)

(56) References Cited

U.S. PATENT DOCUMENTS 8,777,976 B2 7/2014 Brady et al.
8,852,205 B2 10/2014 Brady et al.
(Continued)

FOREIGN PATENT DOCUMENTS

EP   3 335 647 A2   6/2018
JP   2011-507633 A  3/2011
(Continued)

OTHER PUBLICATIONS

International Search Report issued in corresponding International Patent Application No. PCT/IB2019/000942 dated Feb. 10, 2020.
(Continued)

*Primary Examiner* — Todd J Scherbel
(74) *Attorney, Agent, or Firm* — Troutman Pepper Locke LLP

(57) ABSTRACT

A method or use for managing one or more acute ischemic events. The method can include determining criteria of a clot; classifying the clot based on the criteria and generating a classification; determining an individualized treatment protocol for the clot based on the classification, the individualized treatment protocol comprising one or more techniques selected from using aspiration, restoring perfusion using a first reperfusion device, and/or restoring perfusion using a second reperfusion device; and treating the clot based on the individualized treatment protocol.

16 Claims, 53 Drawing Sheets

Related U.S. Application Data on Dec. 27, 2018, provisional application No. 62/785,543, filed on Dec. 27, 2018, provisional application No. 62/782,217, filed on Dec. 19, 2018, provisional application No. 62/722,648, filed on Aug. 24, 2018.

(51) Int. Cl.
| | | |
|---|---|---|
| *A61B 5/02* | (2006.01) | |
| *A61B 5/055* | (2006.01) | |
| *A61B 5/145* | (2006.01) | |
| *A61B 17/00* | (2006.01) | |
| *A61B 17/22* | (2006.01) | |

(52) U.S. Cl.
CPC ........ *A61B 5/14546* (2013.01); *A61B 5/7264* (2013.01); *A61B 17/221* (2013.01); *A61B 2017/00084* (2013.01); *A61B 2017/22079* (2013.01); *A61B 2017/2212* (2013.01); *A61B 2017/2215* (2013.01); *A61B 2217/005* (2013.01)

(58) Field of Classification Search
CPC ... A61B 5/145; A61B 5/14546; A61B 5/7264; A61B 17/221; A61B 2017/00022; A61B 2017/22; A61B 2017/22079; A61B 2017/221; A61B 2017/2212; A61B 2017/2215
See application file for complete search history.

(56) References Cited

U.S. PATENT DOCUMENTS

| | | |
|---|---|---|
| 9,402,707 B2 | 8/2016 | Brady et al. |
| 9,445,829 B2 | 9/2016 | Brady et al. |
| 9,642,639 B2 | 5/2017 | Brady et al. |
| 10,667,833 B2 | 6/2020 | Vale et al. |
| 2008/0194993 A1 | 8/2008 | McLaren et al. |
| 2008/0300493 A1* | 12/2008 | Gatto ................ A61B 90/36 600/479 |
| 2016/0029960 A1 | 2/2016 | Toth et al. |
| 2017/0055908 A1 | 3/2017 | Radman et al. |
| 2017/0071614 A1* | 3/2017 | Vale ................ A61B 90/39 |
| 2017/0196577 A1 | 7/2017 | Sperry et al. |
| 2019/0000492 A1 | 1/2019 | Casey et al. |
| 2019/0374128 A1 | 12/2019 | Palushi et al. |
| 2020/0046267 A1* | 2/2020 | Govari ................ A61B 17/22 |

FOREIGN PATENT DOCUMENTS

| | | |
|---|---|---|
| JP | 2018-86267 A | 6/2018 |
| WO | 2015/000953 A1 | 1/2015 |
| WO | 2015/189354 A1 | 12/2015 |
| WO | 2017/142874 A2 | 8/2017 |
| WO | 2018-096182 A2 | 5/2018 |

OTHER PUBLICATIONS

Notification of Reasons for Refusal issued in Japanese Patent Application No. 2021-510018 dated Jun. 20, 2023, English translation only.

Translation of Chinese Office Action dated Apr. 28, 2024, issued in corresponding CN Application No. 201980070399.1.

Chinese Office Action dated Apr. 28, 2024, issued in corresponding CN Application No. 201980070399.1.

European Search Report dated Jan. 20, 2025, in corresponding EP 24209442.3, and submitted herewith.

\* cited by examiner

900

1000

- Difficult to cross
- Multiple number of passes

**Clots may be either RBC rich or Fibrin rich

Sec. A:A - 1

Sec. A:A - 2

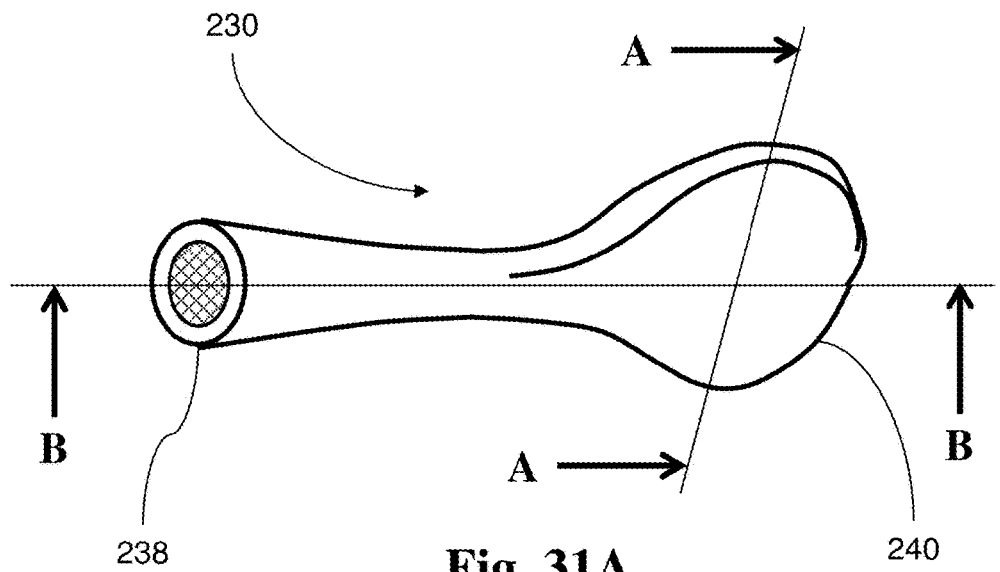
Fig. 31A
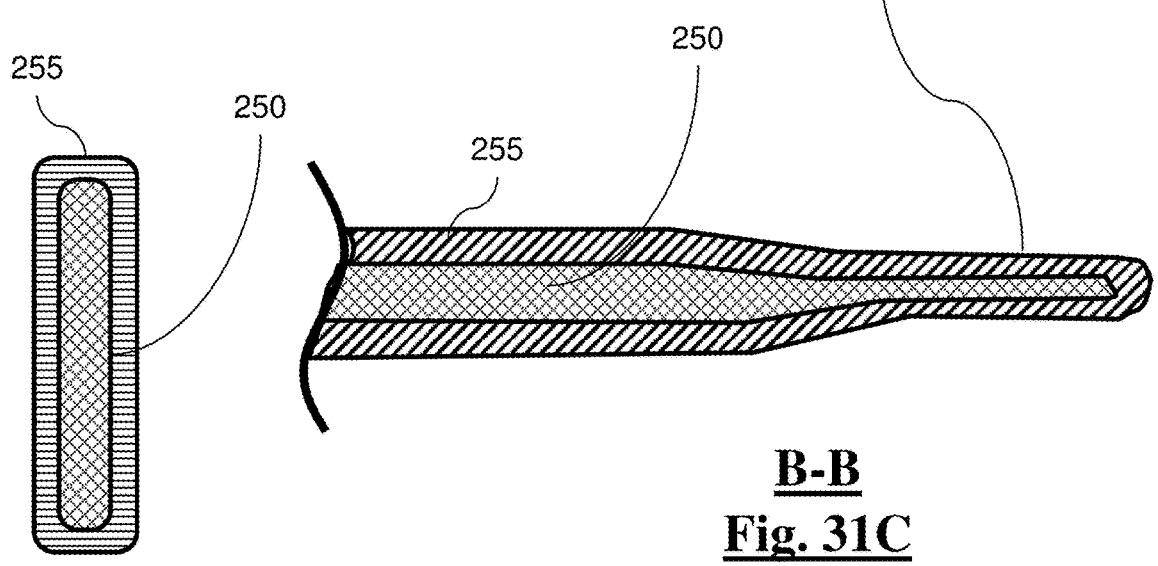
A-A
Fig. 31B
B-B
Fig. 31C

| Clinical characteristics | |
|---|---|
| Intravenous rt-PA administration, n (%) | 38 (63.3) |
| Approximate occlusion length (mm), mean ± SD | 20±30.1 |
| Occlusion site, n (%) | |
| MCA (undefined) | 6 (10) |
| M1 MCA | 20 (33.3) |
| M2 MCA | 10 (16.7) |
| ICA | 8 (13.3) |
| Combined ICA and MCA | 10 (16.7) |
| Combined ACA and MCA | 2 (3.3) |
| Basilar artery | 4 (6.7) |
| Stroke aetiology, n (%) | |
| Atheroembolic | 15 (25) |
| Cardioembolic | 20 (33.3) |
| Cryptogenic | 22 (36.7) |
| Other determined aetiology | 3 (5) |

| Final number of passes per case, n=number of cases (%) | | | | | |
|---|---|---|---|---|---|
| 1 Pass | 2 passes | 3 passes | 4 passes | 5 passes | 6 passes |
| 23 (38.3) | 17 (28.3) | 8 (13.3) | 5 (8.3) | 4 (6.7) | 3 (5) |

| Thrombectomy attempts | | | | | | | |
|---|---|---|---|---|---|---|---|
| | Pass 1 | Pass 2 | Pass 3 | Pass 4 | Pass 5 | Pass 6 | Total |
| Number of cases involving each specific pass, n (%) | 60 (100) | 37 (62) | 19 (32) | 12 (9) | 7 (2) | 3 (8) | 138 |
| Number of passes with clot material successfully retrieved, n (%) | 55 (92) | 24 (65) | 14 (74) | 6 (50) | 4 (57) | 3 (100) | 106 |

| Procedural technique per pass, n=number of passes (%) | | | | | | |
|---|---|---|---|---|---|---|
| Technique | Pass 1 (n=60) | Pass 2 (n=37) | Pass 3 (n=19) | Pass 4 (n=12) | Pass 5 (n=7) | Pass 6 (n=3) |
| Stentriever (n=124) | 50 (83.3) | 34 (91.9) | 18 (94.7) | 12 (94.7) | 7 (100) | 3 (100) |
| Direct aspiration (n=14) | 10 (16.7) | 3 (8.1) | 1 (5.3) | 0 (0) | 0 (0) | 0 (0) |

| mTICI score per pass (n=60), n=number of passes (%) | | | | | | |
|---|---|---|---|---|---|---|
| Pass number | 0 | 1 | 2a | 2b | 2c | 3 |
| Pass 1 (n=60) | 12 (20.0) | 5 (8.3) | 9 (15.0) | 12 (20.0) | 6 (10.0) | 16 (26.7) |
| Pass 2 (n=37) | 4 (10.8) | 2 (5.4) | 6 (16.2) | 10 (27.0) | 3 (8.1) | 12 (32.4) |
| Pass 3 (n=19) | 1 (5.3) | 0 (0) | 3 (15.8) | 7 (36.8) | 2 (10.5) | 6 (31.6) |
| Pass 4 (n=12) | 0 (0) | 0 (0) | 3 (25.0) | 5 (41.7) | 2 (16.7) | 2 (16.7) |
| Pass 5 (n=7) | 1 (14.3) | 0 (0) | 1 (14.3) | 2 (28.6) | 1 (14.3) | 2 (28.6) |
| Pass 6 (n=3) | 0 (0) | 0 (0) | 0 (0) | 2 (66.7) | 0 (0) | 1 (33.3) |

| Final mTICI score, n=number of cases (%) | | | | | |
|---|---|---|---|---|---|
| 0 | 1 | 2a | 2b | 2c | 3 |
| 1 (1.7) | 1 (1.7) | 4 (6.7) | 10 (16.7) | 12 (20) | 32 (53.3) |

Fig. 36

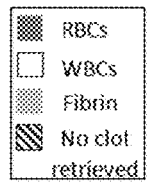
Fig. 41
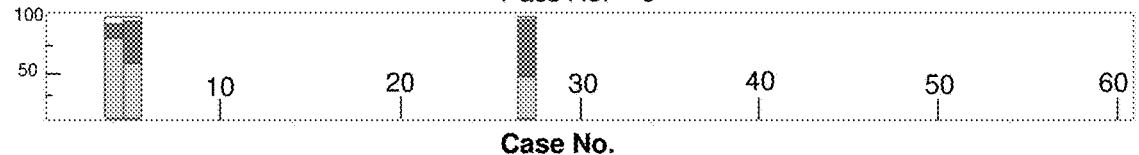
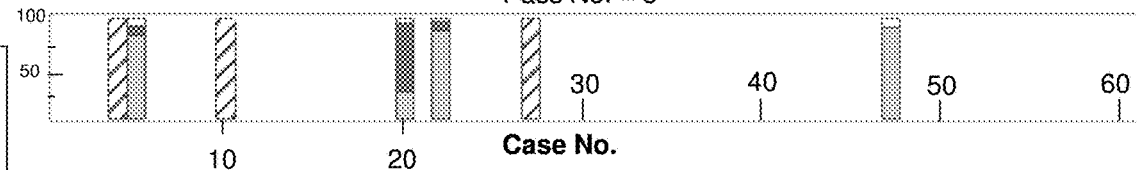
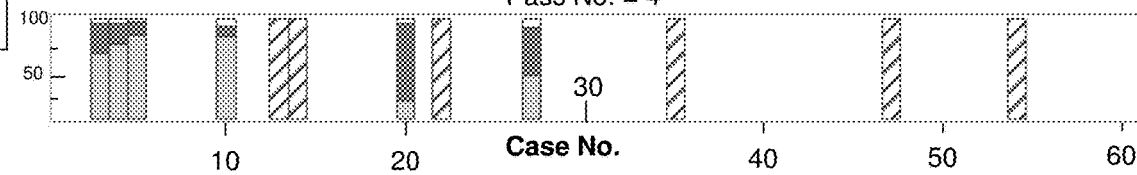
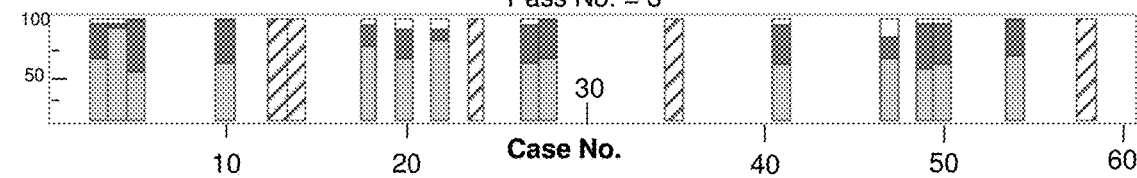
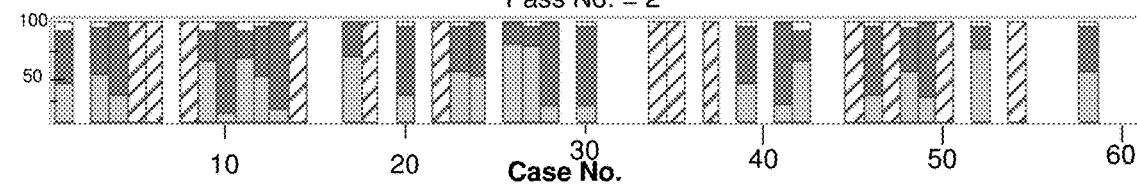
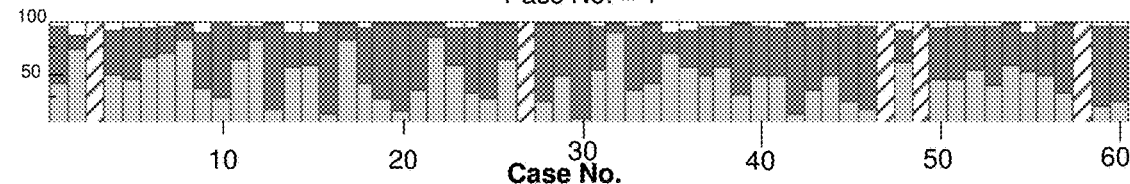

4700

```
┌─────────────────────────────────────────────────────────────┐
│ delivering a catheter to a site of a clot in the vasculature, the │
│ catheter comprising a lumen having a proximal end and a distal │
│ end; and a spectroscopic sensing device connected to the distal │
│ end, the spectroscopic sensing device configured to measure │
│ properties of the clot through the distal end of the catheter │
│                            4710                             │
└─────────────────────────────────────────────────────────────┘
                              │
                              ▼
┌─────────────────────────────────────────────────────────────┐
│ taking a first measurement of the clot using the spectroscopic │
│ sensing device at a first location of the site of the clot in the │
│ vasculature                                                 │
│                            4720                             │
└─────────────────────────────────────────────────────────────┘
                              │
                              ▼
┌─────────────────────────────────────────────────────────────┐
│ generating a spectrum from the first measurement, whereby  │
│ the spectrum relates to at least one of a chemical composition │
│ and physical properties of the clot                         │
│                            4730                             │
└─────────────────────────────────────────────────────────────┘
```

Fig. 47

4900 determining criteria of a clot;
4910 classifying the clot based on the criteria and generating a classification
4920 determining an individualized treatment protocol for the clot based on the classification, the individualized treatment protocol comprising one or more techniques selected from using aspiration, restoring perfusion using a first reperfusion device
4930 restoring perfusion using a second reperfusion device; and treating the clot based on the individualized treatment protocol
4940

```
delivering a guidewire through a microcatheter to a site of a clot
in the vasculature, the guidewire comprising one or more
sensors connected to or adjacent a distal end of the guidewire,
the one or more sensors configured to measure properties of the
clot in the vasculature
                              5010
```

```
sensing properties of the clot using the one or more sensors at
a first location of the site of the clot in the vasculature
                              5020
```

```
generating an output from the sensed properties, whereby the
output relates to at least one of a chemical composition and
physical properties of the clot
                              5030
```

```
delivering a guidewire through a microcatheter to a site of a clot
in the vasculature, the guidewire extending in a longitudinal
direction from a proximal end to a distal end and comprising a
plurality of temperature sensors, whereby at least one of
temperature sensor is positioned proximal of the distal end and
one or more of the other of the sensors are positioned on or
adjacent the distal end, the one or more sensors configured for
sensing temperature of the clot in vivo and identifying
properties of the clot
5110
```

```
sensing properties of the clot using the temperature sensors at
a first location distal of the clot, a second location in the clot,
and a third location proximal of the clot
5120
```

```
generating an output from the sensed properties, whereby the
output relates to at least one of a chemical composition and
physical properties of the clot
5130
```

Fig. 51

5200 
| forming a substantially planar distal end of the guidewire |
| --- |
| 5210 |
cutting a predetermined shape into the distal end of the guidewire, wherein the distal end is wider than a remainder of the guidewire proximal thereof, and wherein the predetermined shape is configured so that the guidewire is incapable of entering a perforating vessel when de-livered to the clot
5220
Fig. 52

5300

```
┌─────────────────────────────────────────────────────┐
│ forming a substantially planar distal end of the    │
│ guidewire                                           │
│ 5310                                                │
└─────────────────────────────────────────────────────┘
                          │
                          ▼
┌─────────────────────────────────────────────────────┐
│ cutting a predetermined shape into the distal end   │
│ of the guidewire                                    │
│ 5320                                                │
└─────────────────────────────────────────────────────┘
                          │
                          ▼
┌─────────────────────────────────────────────────────┐
│ positioning one or more sensors on the distal end   │
│ for sensing the clot                                │
│ 5330                                                │
└─────────────────────────────────────────────────────┘
                          │
                          ▼
┌─────────────────────────────────────────────────────┐
│ positioning one or more sensors on the remainder of │
│ the guidewire for sensing the vessel wall, wherein  │
│ the distal end is substantially planar for receiving│
│ the one or more sensors on the distal end and wider │
│ than a remainder of the guidewire proximal thereof, │
│ and wherein the predetermined shape is configured   │
│ so that the guidewire is capable of being oriented  │
│ in two orientations and is incapable of entering a  │
│ perforating vessel when delivered to the clot       │
│ 5330                                                │
└─────────────────────────────────────────────────────┘
```

Fig. 53

METHOD AND APPARATUS FOR MANAGING ACUTE ISCHEMIC EVENTS

CROSS REFERENCE TO RELATED APPLICATIONS

This application is a U.S. National Phase Application under 35 U.S.C. § 371 of International Patent Application No. PCT/IB2019/000942, filed Aug. 23, 2019, which claims priority to U.S. Provisional Application No. 62/722,648, filed Aug. 24, 2018. U.S. Provisional Application No. 62/782,217, filed Dec. 19, 2018. U.S. Provisional Application Nos. 62/785,543 and 62/785,566, both filed Dec. 27, 2018, and U.S. Provisional Application No. 62/844,559, filed May 7, 2019. All of these disclosures are incorporated herein by reference in their entirety.

FIELD

The disclosure relates to acute management of an ischemic event such as a stroke during the hyperacute timeframe in order to treat the patient and minimize brain injury. In particular, endovascular medical systems advanceable through vasculature for managing acute ischemic events.

BACKGROUND

The World Health Organization estimates that 15,000,000 strokes occur annually. Approximately 87% of all strokes are ischemic—where a blood clot obstructs the flow of blood to an area of the brain, starving it of oxygen and nutrients. Clots may develop and block vessels locally without being released in the form of an embolus—this mechanism is common in the formation of coronary blockages. Acute obstructions are mainly blood clots, but other sources may be fat emboli, cardiac tumors, cardiac or arterial connective tissue, misplaced devices, migrated devices, and the like. Thromboembolism occurs when part or all of a thrombus breaks away from the blood vessel wall. This clot is then carried in the direction of blood flow. Clots can include a range of morphologies and consistencies. Long strands of softer clot material may tend to lodge at bifurcations or trifurcations, resulting in multiple vessels being simultaneously occluded over significant lengths. Older clot material can also be less compressible than softer fresher clots, and under the action of blood pressure may distend the compliant vessel in which it is lodged. Clots also vary greatly in length, even if lodged in the same region of the vascular anatomy. For example, clots occluding the middle cerebral artery of an ischemic stroke patient may range from just a few millimeters to several centimeters in length.

Of the approximately 13,000,000 ischemic strokes that occur annually, one-third of patients die and another one-third are disabled. Two of the primary factors associated with mortality in these patients are the occlusion location and the time to treatment. Regarding treatment time from symptom onset, treating the occlusion as fast as practical is important to avoid complications that result in vessels deprived of flow because of said occlusion. Intravenous (IV) thrombolytics are used for patients presenting up to 4.5 hours after symptom onset. Guidelines recommend administering IV thrombolytics in the 3-4.5 hour window to those patients who meet the ECASS 3 (European Cooperative Acute Stroke Study 3) trial inclusion/exclusion criteria. As for location, large-vessel occlusions, which are present in 46% of unselected acute stroke patients presenting in academic medical centers, are associated with higher stroke severity. Additionally, not all patients may be treated with thrombolytic therapy, and so mechanical thrombectomy is a valuable alternative in patients contraindicated to t-PA (tissue plasminogen activator) or where t-PA treatment was not effective. These more proximal vessels feed a large volume of brain tissue, ergo clinicians use the presenting NIHSS (National Institute of. Health Stroke Scale) score as an indicator of large-vessel occlusion.

With this, it is understood that an ischemic stroke may result if the clot lodges in the cerebral vasculature. In the United States alone, roughly 700,000 acute ischemic stroke (AIS) cases occur every year and this number is expected to increase with an ageing population. Occlusion of these large arteries in ischemic stroke is associated with significant disability and mortality. Revascularization of intracranial artery occlusions is the therapeutic goal in stroke therapy.

Endovascular mechanical revascularization (thrombectomy) is an increasingly used method or use for intracranial large vessel recanalization in acute stroke. Such devices based on stent-like technology, referred to as "stentrievers" or "stent-retrievers", are currently displacing first generation thrombectomy devices for recanalization in acute ischemic stroke. There are significant challenges associated with designing clot removal devices that can deliver high levels of performance. There are also a number of access challenges that make it difficult to deliver devices. For example, the vasculature in the area in which the clot may be lodged is often fragile and delicate. In particular, neurovascular vessels are more fragile than similarly sized vessels in other parts of the body and are often just sparsely connected to the surrounding soft tissue bed. Excessive tensile forces applied to these vessels could result in perforations and hemorrhage. Peri-interventional subarachnoid hemorrhage (SAH) is one of the most feared complications associated with endovascular thrombectomy therapy.

There are also significant challenges associated with designing clot removal devices that can deliver high levels of performance. First, the vasculature can present a number of access challenges that make it difficult to deliver devices. In cases where access involves navigating the aortic arch (such as coronary or cerebral blockages), the configuration of the arch in some patients makes it difficult to position a guide catheter. These difficult arch configurations are classified as either type 2 or type 3 aortic arches with type 3 arches presenting the most difficulty.

The reason for poor revascularization results using current devices and approaches is multifaceted. Challenges such as the type of clot, length of the clot, vascular architecture, and patient comorbidities can play key roles. Complex vessel tortuosity in some patients, particularly in the aged can further exacerbate the difficulty of addressing these challenging occlusions. Tortuosity can make it more difficult not just to access but also to dislodge the clot, possibly due to the line of force applied to the clot by the device and the potential for vessel movement and deformation.

Regarding variation in types of clots, clots can range broadly in their composition, distribution of components (heterogeneity) and mechanical properties. The variation is due to multiple factors, including but not limited to origin of the clot, clot location, age of the clot, cellular content, non-cellular content, red blood cells, platelets, and white blood cells. Non-cellular content can include factors such as fibrin, platelets, von Willebrand factor (vWF) (i.e. a blood glycoprotein involved in hemostasis), as well as collagen. Other factors can include levels of serum in the clot, calcified deposits, lipids, clot shape, clot size, heterogeneity of distribution of constituents, as well as pathogenesis.

Because of these several factors affecting clot formation a broad spectrum of clot types are observed, for example certain clots can have long strands of deformable clot material which may tend to lodge at bifurcations or trifurcations, resulting in multiple vessels being simultaneously occluded over significant lengths. More mature and organized clot material is likely to be less compressible than a softer fresher clot, and under the action of blood pressure it may distend the compliant vessel in which it is lodged. Further, as understood throughout this disclosure, clots that have a high fibrin content (e.g., higher than 40% fibrin content) can have a high coefficient of friction (e.g., be more stiff and/or be connected more strongly to the vessel wall), which renders fibrin-rich clots very difficult to dislodge. Multiple passes by a device may be required to remove or even dislodge fibrin rich clots from the vasculature when compared to the relatively higher red blood cell (RBC) content clots, which can be softer and less stiff. Further, the properties of the clot may be significantly changed by the action of the retrieval device interacting with the clot (e.g., after the device makes a first pass of the clot). For example, compression of a blood clot can cause dehydration of the clot and result in a dramatic increase in both clot stiffness and coefficient of friction.

While it is possible to assess many of these characteristics in vitro by examining individual clots removed during mechanical thrombectomy procedures, in vitro tests have several clear limitations. Foremost, they are time consuming and often destructive to the sample. Samples may have to undergo extensive processing to make them amenable to in vitro analysis. Significantly for some pathologies, such as acute ischemic stroke, time to treatment is a critical factor for patient outcomes and in vitro tests may not be a practical way to determine the best treatment for the patient because of the time involved with sampling and analysis.

The solution of this disclosure resolves these limitations and other issues of the art through an in vivo measurement approach to improve management of acute ischemic events.

SUMMARY

Disclosed herein are various exemplary devices, systems, and method or uses of the present disclosure that can address the above needs. In some embodiments, a catheter is disclosed for delivery to and analyzing properties of a clot in a blood vessel. The catheter can include a lumen having a proximal end and a distal end; and a spectroscopic mechanism for analyzing clot composition at a site of the clot in the vasculature.

In some embodiments, a method or use for managing one or more acute ischemic events is disclosed, that can include determining criteria of a clot; classifying the clot based on the criteria and generating a classification; determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and treating the clot based on the individualized treatment protocol.

In some embodiments, the step of classifying the clot is carried out in vivo.

In some embodiments, the first reperfusion device is a stent retriever and the second reperfusion device is a pinch retriever.

In some embodiments, the classifying the clot comprises one or more of a clinical exam, a blood test, a computerized tomography (CT) scan, a magnetic resonance imaging (MRI) scan, a carotid ultrasound, a cerebral angiogram, and an echocardiogram.

In some embodiments, the determining criteria of the clot can include performing at least one of a CT scan and an MRI scan; and analyzing information from at least one of the CT scan and the MRI scan to determine physical and/or chemical composition of the clot, including levels of red blood cell content, white blood cell content, levels of fibrin, levels of platelets, level of hydration, a clot size, a clot shape, and/or a clot location in the vasculature.

In some embodiments, the first reperfusion device is a stent retriever configured to remove a clot or portions of a clot that are red blood cell rich and the second reperfusion device is a pinch retriever configured to remove a clot or portions of a clot that are fibrin-rich. In certain embodiments, if the classification demonstrates that the clot is red blood cell rich, then the individualized treatment protocol can include passing the first reperfusion device by, through, or about the clot and then retracting the first perfusion device while engaging the clot in a lumen of the first reperfusion device to restore reperfusion to the vessel.

In some embodiments, the first reperfusion device is a stent retriever configured to remove a clot or portions of a clot that are red blood cell rich and the second reperfusion device is a pinch retriever configured to remove a clot or portions of a clot that are fibrin-rich. In certain embodiments, if the classification demonstrates that the clot is fibrin-rich, then the individualized treatment protocol can include passing the second reperfusion device by, through, or about the clot and then retracting the second perfusion device while pinching the clot to restore reperfusion to the vessel.

In some embodiments, a clot is classified as red blood cell rich if the clot is comprised of 30% or more red blood cell count. In some embodiments, a clot is classified as white blood cell rich if the clot is comprised of 30% or more white blood cell count. In some embodiments. a clot is classified as fibrin rich if the clot is comprised of 30% or more fibrin.

In some embodiments, the step of determining criteria of the clot includes interpreting information, by a computing device in operative communication with the clot, about the clot to determine in real-time levels (e.g., instantly or within minutes of undertaking the analysis) of at least one of red blood cell content, white blood cell content, levels of fibrin, levels of platelets, levels of hydration, a clot size, a clot shape, and/or a clot location in the vasculature. In some embodiments, the method or use can also include receiving, through a graphical user interface of the computing device, the individualized treatment protocol, monitoring, by the computing device, perfusion of the vessel with the clot, and, alerting, by the computing device, in response to perfusion being restored in the vessel.

In some embodiments, the computing device is linked to a database comprising correlation data for interpreting information about the clot and determining the individualized treatment protocol. The database can be remote from the computing device.

In some embodiments, the determining criteria of the clot includes delivering a catheter to a site of the clot in the vasculature; and taking a first reading of the clot by a using instrumentation for near infrared spectroscopy (NIR) coupled to the catheter at a first location of the site of the clot in the vasculature, and generating a spectrum from the first reading, whereby the spectrum relates to at least one of a chemical composition and/or physical properties of the clot.

In some embodiments, the step of determining criteria of the clot further includes interpreting information contained in the spectrum to determine in real-time at least one of levels of red blood cell content, white blood cell content, levels of fibrin, levels of platelets, level of hydration, a clot size, a clot shape, and/or a clot location in the vasculature.

In some embodiments, the method or use can also include taking a second reading of the clot by using the instrumentation for NIR at a second location distal or proximal of the clot and the first location, generating a spectrum from the second reading, whereby the spectrum of the second reading relates to at least one of a chemical composition and/or physical properties of the clot, and interpreting information contained in the spectrum of the first reading and the second reading to instantly determine at least one of levels of red blood cell content, levels of white blood cell content, levels of fibrin, levels of platelets, level of hydration, a clot size, a clot shape, and/or a clot location in the vasculature.

In some embodiments, the determining criteria of the clot includes taking measurements of the clot at its proximal end and its distal end, and generating a spectrum from measurements of the clot at its proximal end and its distal end, whereby the spectrum relates to at least one of a chemical composition and/or physical properties of the clot.

In some embodiments, the step of determining criteria of the clot includes delivering a catheter to a site of the clot in the vasculature, taking a first reading of the clot by a using instrumentation for Raman spectroscopy (and/or a visible region of the spectrum) coupled to the catheter at the site of the clot in the vasculature, and generating a spectrum from the first reading, whereby the spectrum relates to at least one of a chemical composition and/or physical properties of the clot. In some embodiments, the step of determining criteria of the clot also includes interpreting information contained in the spectrum to determine in real-time levels of red blood cell content, white blood cell content, levels of fibrin, levels of platelets, level of hydration, a clot size, a clot shape, and/or a clot location in the vasculature.

In some embodiments, the method or use includes taking a second reading of the clot by using the instrumentation for Raman spectroscopy at a second location distal or proximal of the clot and the first location, generating a spectrum from the second reading, whereby the spectrum of the second reading relates to a chemical composition and/or physical properties of the clot, and interpreting information contained in the spectrum of the first reading and the second reading to determine in real-time at least one of levels of red blood cell content, white blood cell content, levels of fibrin, levels of platelets, level of hydration, a clot size, a clot shape, and/or a clot location in the vasculature.

In some embodiments, the step of treating of the clot includes retrieving a portion of the clot. The method or use can also include analyzing the retrieved clot and/or one or more fragments of the clot, and selecting a clot treatment step based on analyzing the retrieved clot or analyzing accessing and crossing the clot. However, this example is not so limited and the clot analysis of this embodiment is contemplated to include analyzing any material in communication or otherwise connected with the respective reperfusion device (e.g., serum or any other particulate associated with the clot).

In some embodiments, the step of determining criteria of the clot includes determining one or more quantitative indications selected from one or more of white blood cell levels, red blood cell levels, serum levels, fibrin levels, levels of platelets, level of hydration, clot size, clot location, clot strength, clot elasticity, rate of clot formation or rate of clot lysis. The method or use can include comparing the first and the second clot characteristic quantitative indications to correlation data and determining a selection and/or order of using one or more techniques selected from aspiration, a first reperfusion device, and/or a second reperfusion device.

In some embodiments, a system for treating an ischemic event is disclosed. The system can include a means for providing in vivo analysis information of a clot of the subject having an ischemic event, a means for providing an indication of an individualized treatment protocol for the subject based upon the analysis information, the individualized treatment comprising one or more techniques selected from using aspiration, restoring perfusion using a first reperfusion device, and/or restoring perfusion using a second reperfusion device; and means for treating the clot based on the individualized treatment protocol.

In some embodiments, the first reperfusion device of the system is a stent retriever configured to remove a clot or portions of a clot that are red blood cell rich and the second reperfusion device is a pinch retriever configured to remove a clot or portions of a clot that are fibrin-rich. In some embodiments, if the indication demonstrates that the clot is red blood cell rich, then the individualized treatment protocol includes a means for passing the first reperfusion device by, through, or about the clot and then retracting the first perfusion device while engaging the clot in a lumen of the first reperfusion device to restore reperfusion to the vessel.

In some embodiments, the first reperfusion device is a stent retriever configured to remove a clot or portions of a clot that are red blood cell rich and the second reperfusion device is a pinch retriever configured to remove a clot or portions of a clot that are fibrin-rich. In some embodiments, if the classification demonstrates that the clot is fibrin-rich, then the individualized treatment protocol includes a means for passing the second reperfusion device by, through, or about the clot and then retracting the second perfusion device while pinching the clot to restore reperfusion to the vessel.

In some embodiments, a system for treating an ischemic event is disclosed. The system can include a first reperfusion device for restoring perfusion to an occluded vessel having a clot. The system can include a second reperfusion device for restoring perfusion to the occluded vessel having the clot. The system can include a delivery system for delivering at least one of the first and second reperfusion devices to the clot in the occluded vessel. The system can include a clot analysis system for analyzing the clot of the occluded vessel and determining an individualized treatment protocol. The delivery system can include at least one of a guide catheter, a guidewire, a microcatheter and the like, each of which are operable to delivered through the vasculature to the site of the clot.

In some embodiments, the spectroscopic mechanism is configured to emit light capable of penetrating the clot to produce a spectrum that relates to the chemical composition and/or physical properties of one or more portions of the clot exposed to light of the spectroscopic mechanism. The spectrum can include spectral bands that provide indications related to the chemical composition and/or physical properties of one or more portions of the clot.

In some embodiments, the spectroscopic mechanism includes an optical fiber or bundle of fibers extended up to or adjacent the distal end of the catheter; and a mirror oriented at a predetermined angle adjacent or at the distal end. Light can be emitted from the fiberoptic bundle and reflected towards a vessel wall and/or the clot. The predetermined angle can be approximately 45°. The light can be reflected towards the vessel wall from the mirror at approximately 90°.

In some embodiments, the catheter is capable of rotating 360° and taking a 360° scan of the vessel with the clot.

In some embodiments, the spectroscopic mechanism is integrated with the catheter and is configured to emit light capable of penetrating the clot to analyze the clot using near-infrared spectroscopy (NIRS). The spectroscopic mechanism can include a near infrared region of the electromagnetic spectrum (780 to 2500 micrometers).

In some embodiments, the spectroscopic mechanism is integrated with the catheter and is configured to analyze the clot composition using Raman spectroscopy.

In some embodiments, the spectroscopic mechanism is integrated with the catheter and is configured as a visible light diagnostic device that emits light capable of penetrating the clot to analyze the clot composition.

In some embodiments, a microcatheter is disclosed for analyzing an ischemic clot in the vasculature. The microcatheter can include a lumen having a proximal end and a distal end. A spectroscopic sensing device can be connected to the distal end whereby the spectroscopic sensing device can be configured to measure properties of the clot through the distal end of the microcatheter. The distal end can include a window portion that is transparent and an absorbent portion adjacent the window portion that is opaque. The window portion is constructed using one or more of Polycarbonate, Poly methylmethacrylate (PMMA), and perfluorinated polymers.

In some embodiments, the spectroscopic sensing device can include a near infrared region of the electromagnetic spectrum (780 to 2500 micrometers).

In some embodiments, a method or use is disclosed for managing one or more acute ischemic events. The method or use can include delivering a catheter to a site of a clot in the vasculature. The catheter can include a lumen having a proximal end and a distal end; and a spectroscopic sensing device connected to the distal end, the spectroscopic sensing device configured to measure properties of the clot through the distal end of the catheter. The method or use can include taking a first measurement of the clot using the spectroscopic sensing device at a first location of the site of the clot in the vasculature. The method or use can also include generating a spectrum from the first measurement, whereby the spectrum relates to at least one of a chemical composition and physical properties of the clot.

In some embodiments, the method or use includes classifying the clot based on the criteria and generating a classification.

In some embodiments, the method or use includes advancing the distal end of the catheter distal of the clot and then retracting the distal end of the catheter backwards through the clot while simultaneously spinning the catheter to produce a spectral map over a length of vessel that is occluded by the clot.

In some embodiments, the method or use includes ascertaining one or more physical properties of the clot by measuring different spectral features of the clot based on the spectrum.

In some embodiments, the method or use includes interpreting information contained in the spectrum to determine in real-time at least one of levels of red blood cell content, white blood cell content, levels of fibrin, a clot size, a clot shape, and a clot location in the vasculature.

In some embodiments, the method or use includes taking a second measurement of the clot using the spectroscopic sensing device at a second location distal or proximal of the clot and the first location; and generating a spectrum from the second measurement, whereby the spectrum of the second measurement relates to at least one of a chemical composition and physical properties of the clot.

In some embodiments, the step of taking the first measurement or the second measurement or multiple measurements includes emitting light from the spectroscopic sensing device that penetrates the clot at the respective first or second or multiple locations and generating the spectrum that relates to the chemical composition and/or physical properties of the clot region exposed to the emitted light of the spectroscopic device.

In some embodiments, the method or use includes rotating the catheter 360° and scanning inside of the vessel of the clot to generate a 360° scan.

In some embodiments, the method or use includes pulling the catheter tip backwards, after being initially placed distal to the thrombus, through an occlusion whilst simultaneously spinning.

In some embodiments, the method or use includes advancing the catheter tip forwards, after being initially placed proximal to the thrombus, through an occlusion whilst simultaneously spinning.

In some embodiments, the spectroscopic sensing devices includes a fiberoptic bundle disposed inside the microcatheter and extended up to or adjacent the distal end of the microcatheter and a mirror oriented at a predetermined angle adjacent or at the distal end. In this respect, the step of taking the first measurement or the second measurement includes emitting emitted from the fiberoptic bundle and reflecting the light towards the clot and/or a vessel wall of the vasculature of the clot. The predetermined angle of the mirror can be approximately 45°. The light can be reflected towards the vessel wall from the mirror at approximately 90°.

In some embodiments, the spectroscopic sensing device can be integrated with the catheter and is configured to emit light capable of penetrating the clot to analyze the clot using near-infrared spectroscopy.

In some embodiments, the spectroscopic sensing device can be integrated with the catheter and is configured to emit light capable of penetrating the clot to analyze the clot using Raman spectroscopy.

In some embodiments, the spectroscopic sensing device is a visible light diagnostic device integrated with the catheter and is configured to emit light capable of penetrating and analyzing the clot.

In some embodiments, the step of classifying the clot comprises one or more of histological quantification of clot components, mechanical engineering test of the clot, a computerized tomography (CT) scan, a magnetic resonance imaging (MRI) scan, a carotid ultrasound, and a cerebral angiogram.

In some embodiments, the method or use also includes determining criteria of the clot by performing at least one of a CT scan and an MRI scan and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

In some embodiments, the step of determining criteria of the clot further includes: interpreting information, by a computing device in operative communication with the clot, about the clot to determine in real-time levels of red blood cell content, white blood cell content, levels of fibrin, a clot size, a clot shape, and/or a clot location in the vasculature. In this respect, the method or use can include receiving, through a graphical user interface of the computing device, the individualized treatment protocol; monitoring, by the computing device, perfusion of the vessel with the clot; and, alerting, by the computing device, in response to perfusion being restored in the vessel. The computing device can be linked to a database comprising correlation data for interpreting information about the clot and determining the individualized treatment protocol and the database is remote from the computing device.

In some embodiments, the step of determining criteria of the clot includes determining one or more quantitative indications selected from one or more of white blood cell levels, red blood cell levels, serum levels, fibrin levels, clot size, clot location, clot strength or clot elasticity. In this respect, the step of determining can include one or more quantitative indications selected from one or more of white blood cell levels, red blood cell levels, serum levels, fibrin levels, clot size, clot location, clot strength or clot elasticity. The method or use can also include comparing the first and the second clot characteristic quantitative indications to correlation data and determining at least one of a selection and order of using one or more techniques selected from aspiration, a first reperfusion device, and/or a second reperfusion device.

In some embodiments, a method or use is disclosed for calibrating a system for analyzing clots. The method or use can include providing a database of at least one of a chemical composition and physical properties of one or more clots previously scanned using a spectrophotometer; generating a calibration set of data using the database and a reference analytical method or use; and correlating the calibration set of data with spectral features of a spectroscopic sensing device of the system for analyzing clots.

In some embodiments, the system includes a catheter comprising a lumen having a proximal end and a distal end; and the spectroscopic sensing device connected to the distal end, the spectroscopic sensing device configured to measure properties of the clot through the distal end of the catheter.

In some embodiments, a system is disclosed for use with a clot located in a target vessel for managing one or more acute ischemic events. The system can include a guidewire extending in a longitudinal direction from a proximal end to a distal end, the distal end being configured to control its orientation relative to the clot and the target vessel. The guidewire can include one or more sensors disposed on or adjacent the distal end, the one or more sensors configured for sensing properties of the clot in vivo and treating the clot based on the sensed properties.

In some embodiments, the distal end of the guidewire is configured to prevent injury to an inner wall of the target vessel.

In some embodiments, the one or more sensors are near infrared (NIR) sensors disposed on an outer surface of the guidewire.

In some embodiments, the one or more sensors are impedance sensors disposed on an outer surface of the guidewire.

In some embodiments, the one or more sensors are Raman spectroscopy sensors disposed on an outer surface of the guidewire and operable to transmit and collect certain ranges of the electromagnetic spectrum.

In some embodiments, the one or more sensors are one or more fiberoptic strands or bundles disposed on an outer surface of the guidewire and operable to transmit and collect certain ranges of the electromagnetic spectrum.

In some embodiments, the distal end of the guidewire is an atraumatic clot-circumventing configured distal end, and wherein the one or more sensors are circumferentially disposed about an outer surface of the guidewire.

In some embodiments, the distal end of the guidewire is a flattened distal portion having a planar geometric shape and thickness less than an outer diameter of a remaining non-flattened portion. In some embodiments, at least one of the one or more sensors is disposed on the flattened distal portion for sensing properties of the clot and the other of the one or more sensors is disposed on the remaining non-flattened portion for sensing properties of the vessel wall.

In some embodiments, the flattened distal portion has a paddle geometric shape.

In some embodiments, the distal end of the guidewire is an atraumatic clot-circumventing configured distal end that is conformable in the lateral direction complementary to a contour of the inner wall of the target vessel when passed between the inner wall of the target vessel and the clot. When in a compressed state subject to application of an external mechanical force, a widest width in a lateral direction of the distal end of the guidewire is reduceable.

In some embodiments, the system also includes a microcatheter comprising a proximal end and a distal end, wherein the guidewire is advanceable through the microcatheter. While in a non-compressed state not subject to application of an external mechanical force, the atraumatic clot-circumventing distal end of the guidewire having the widest width in the lateral direction greater than the inner diameter of the lumen (e.g., twice as big, thrice as big, etc.).

In some embodiments, a method or use for managing one or more acute ischemic events, is disclosed. The method or use can include delivering a guidewire through a microcatheter to a site of a clot in the vasculature, the guidewire comprising one or more sensors connected to or adjacent a distal portion of the guidewire, the one or more sensors configured to measure properties of the clot in the vasculature; sensing properties of the clot using the one or more sensors at a first location of the site of the clot in the vasculature; and generating an output from the sensed properties, whereby the output relates to at least one of a chemical composition and physical properties of the clot.

In some embodiments, the method or use includes positioning at least one of the one or more sensors on a flattened distal portion for sensing properties of the clot; and positioning the other of the one or more sensors on the remaining non-flattened portion for sensing properties of the vessel wall.

In some embodiments, the method or use includes classifying the clot based on the sensed properties and generating a classification.

In some embodiments, the method or use includes ascertaining one or more physical properties of the clot by measuring different spectral features of the clot based on the output.

In some embodiments, the method or use includes interpreting information contained in the output to determine in real-time at least one of levels of red blood cell content, white blood cell content, levels of fibrin, a clot size, a clot shape, and a clot location in the vasculature.

In some embodiments, the method or use includes sensing properties of the clot using the one or more sensors at a second location distal or proximal of the clot and the first location; and generating an output from the second location, whereby the output of the second location relates to at least one of a chemical composition and physical properties of the clot.

In some embodiments, the method or use includes classifying the clot based on the output and one or more of a clinical exam, a blood test, a computerized tomography (CT) scan, a magnetic resonance imaging (MRI) scan, a carotid ultrasound, a cerebral angiogram, and an echocardiogram.

In some embodiments, the method or use includes determining criteria of the clot by performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

In some embodiments, the method or use includes determining criteria of the clot by determining one or more quantitative indications selected from one or more of white blood cell levels, red blood cell levels, serum levels, fibrin levels, clot size, clot location, clot strength, clot elasticity, rate of clot formation or rate of clot lysis.

In some embodiments, an endovascular medical system is disclosed for use with a clot located in a target vessel for managing one or more acute ischemic events. The system can include a guidewire extending in a longitudinal direction from a proximal end to a distal end, wherein the guidewire comprises a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot.

In some embodiments, the one or more sensors are configured to simultaneously measure temperature of a plurality of locations of the clot and target vessel.

In some embodiments, the sensors are selectively positioned at locations along the distal end to measure regions of the clot.

In some embodiments, the one or more sensors are each separated a predetermined distance at locations along the distal end to measure regions of the clot.

In some embodiments, the distal end of the guidewire comprises an expanded perimeter with an atraumatic clot-circumventing configured distal end in a delivery configuration, and wherein the one or more sensors are disposed about the expanded perimeter.

In some embodiments, the expanded perimeter has an elliptical, curved, or paddle geometric shape.

In some embodiments, the distal end of the guidewire comprises an expanded perimeter defined by a loop with a void therebetween in a delivery configuration, the loop comprising two elongate sections extended distally and joined at the distal end, and wherein the one or more sensors are disposed about the elongate sections.

In some embodiments, the loop and the void have an elliptical, curved, or paddle geometric shape.

In some embodiments, the distal end of the guidewire is conformable in the lateral direction complementary to a contour of the inner wall of the target vessel when passed between the inner wall of the target vessel and the clot; and when in a compressed state subject to application of an external mechanical force, a widest width in a lateral direction of the distal end of the guidewire is reduceable.

In some embodiments, a method or use is disclosed for managing one or more acute ischemic events. The method or use can include delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot; sensing properties of the clot using the temperature sensors at a first location distal of the clot, a second location in the clot, and third location proximal of the clot; and generating an output from the sensed properties, whereby the output relates to at least one of a chemical composition and physical properties of the clot.

In some examples, the step of sensing properties with the temperature sensors is done simultaneously at each location.

In some examples, the method or use can include selectively positioning the sensors at predetermined locations along the distal end to measure regions of the clot.

In some examples, the method or use can include separating each sensor a predetermined distance at locations along the distal end to measure regions of the clot.

In some examples, the distal end of the guidewire comprises an expanded perimeter with an atraumatic clot-circumventing configured distal end in a delivery configuration, and wherein the one or more sensors are disposed about the expanded perimeter.

In some examples, the method or use can include classifying the clot based on the sensed properties and generating a classification.

In some embodiments, the method or use can include selecting one or more devices and/or procedural steps to treat the clot based on the output.

In some examples, the method or use can include interpreting information contained in the output to determine in real-time at least one of levels of red blood cell content, white blood cell content, platelet content, levels of fibrin, a clot size, a clot shape, clot density, and a clot location in the vasculature.

In some examples, the method or use can include classifying the clot based on the output and one or more of a clinical exam, a blood test, a computerized tomography (CT) scan, a magnetic resonance imaging (MRI) scan, an ultrasound, a cerebral angiogram, and an echocardiogram.

In some embodiments, a method or use is disclosed for managing one or more acute ischemic events. The method or use can include delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot; sensing properties of the clot using the temperature sensors at a plurality of locations in the clot; and generating an output from the sensed properties, whereby the output relates to at least one of a chemical composition and physical properties of the clot.

In some examples, the method or use can include classifying sensing properties of the clot at a location distal and/or proximal of the clot.

In some embodiments, a method or use for managing one or more acute ischemic events is disclosed. The method or use can include determining criteria of a clot; classifying the clot based on the criteria and generating a classification; determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and treating the clot based on the individualized treatment protocol.

In some embodiments, the step of classifying the clot is carried out in vivo, for example, using any of the herein disclosed sensing instrumentalities such as the guidewire with one or more sensors.

In some embodiments, the first reperfusion device is a stent retriever and the second reperfusion device is a pinch retriever.

In some embodiments, the classifying the clot comprises one or more of a clinical exam, a blood test, a computerized tomography (CT) scan, a magnetic resonance imaging (MRI) scan, a carotid ultrasound, a cerebral angiogram, and an echocardiogram.

In some embodiments, the determining criteria of the clot can include performing at least one of a CT scan and an MRI scan; and analyzing information from at least one of the CT scan and the MRI scan to determine physical and/or chemical composition of the clot, including levels of red blood cell content, white blood cell content, levels of fibrin, levels of platelets, level of hydration, a clot size, a clot shape, and/or a clot location in the vasculature.

In some embodiments, the first reperfusion device is a stent retriever configured to remove a clot or portions of a clot that are red blood cell rich and the second reperfusion device is a pinch retriever configured to remove a clot or portions of a clot that are fibrin-rich and/or platelet-rich. In certain embodiments, if the classification demonstrates that the clot is red blood cell rich, then the individualized treatment protocol can include passing the first reperfusion device by, through, or about the clot and then retracting the first perfusion device while engaging the clot in a lumen of the first reperfusion device to restore reperfusion to the vessel.

In some embodiments, the first reperfusion device is a stent retriever configured to remove a clot or portions of a clot that are red blood cell rich and the second reperfusion device is a pinch retriever configured to remove a clot or portions of a clot that are fibrin-rich and/or platelet-rich. In certain embodiments, if the classification demonstrates that the clot is fibrin-rich and/or platelet-rich, then the individualized treatment protocol can include passing the second reperfusion device by, through, or about the clot and then retracting the second perfusion device while pinching the clot to restore reperfusion to the vessel.

In some embodiments, a clot is classified as red blood cell rich if the clot is comprised of 30% or more red blood cell count. In some embodiments, a clot is classified as white blood cell rich if the clot is comprised of 30% or more white blood cell count. In some embodiments, a clot is classified as fibrin rich and/or platelet rich if the clot is comprised of 30% or more fibrin.

In some embodiments, the step of determining criteria of the clot includes interpreting information, by a computing device in operative communication with the clot, about the clot to determine in real-time levels (e.g., instantly or within minutes of undertaking the analysis) of at least one of red blood cell content, white blood cell content, levels of fibrin, levels of platelets, levels of hydration, a clot size, a clot shape, and/or a clot location in the vasculature. In some embodiments, the method or use can also include receiving, through a graphical user interface of the computing device, the individualized treatment protocol, monitoring, by the computing device, perfusion of the vessel with the clot, and, alerting, by the computing device, in response to perfusion being restored in the vessel.

In some embodiments, the computing device is linked to a database comprising correlation data for interpreting information about the clot and determining the individualized treatment protocol. The database can be remote from the computing device.

In some embodiments, the determining criteria of the clot includes delivering a guidewire to a site of the clot in the vasculature, such as the herein disclosed guidewire with one or more sensors; and taking a first reading of the clot by a using instrumentation for near infrared spectroscopy (NIR) coupled to the guidewire at a first location of the site of the clot in the vasculature, and generating a spectrum from the first reading, whereby the spectrum relates to at least one of a chemical composition and/or physical properties of the clot.

In some embodiments, the step of determining criteria of the clot further includes interpreting information contained in the spectrum to determine in real-time at least one of levels of red blood cell content, white blood cell content, levels of fibrin, levels of platelets, level of hydration, a clot size, a clot shape, and/or a clot location in the vasculature.

In some embodiments, the method or use can also include taking a second reading of the clot by using the instrumentation for NIR at a second location distal or proximal of the clot and the first location, generating a spectrum from the second reading, whereby the spectrum of the second reading relates to at least one of a chemical composition and/or physical properties of the clot, and interpreting information contained in the spectrum of the first reading and the second reading to instantly determine at least one of levels of red blood cell content, levels of white blood cell content, levels of fibrin, levels of platelets, level of hydration, a clot size, a clot shape, and/or a clot location in the vasculature.

In some embodiments, the determining criteria of the clot includes taking measurements of the clot at its proximal end and its distal end, and generating a spectrum from measurements of the clot at its proximal end and its distal end, whereby the spectrum relates to at least one of a chemical composition and/or physical properties of the clot.

In some embodiments, the step of determining criteria of the clot includes delivering a guidewire to a site of the clot in the vasculature, such as any of the herein disclosed guidewires with one or more sensors, taking a first reading of the clot by a using instrumentation for Raman spectroscopy (and/or a visible region of the spectrum) coupled to the guidewire at the site of the clot in the vasculature, and generating a spectrum from the first reading, whereby the spectrum relates to at least one of a chemical composition and/or physical properties of the clot. In some embodiments, the step of determining criteria of the clot also includes interpreting information contained in the spectrum to determine in real-time levels of red blood cell content, white blood cell content, levels of fibrin, levels of platelets, level of hydration, a clot size, a clot shape, and/or a clot location in the vasculature.

In some embodiments, the method or use includes taking a second reading of the clot by using the instrumentation for Raman spectroscopy at a second location distal or proximal of the clot and the first location, generating a spectrum from the second reading, whereby the spectrum of the second reading relates to a chemical composition and/or physical properties of the clot, and interpreting information contained in the spectrum of the first reading and the second reading to determine in real-time at least one of levels of red blood cell content, white blood cell content, levels of fibrin, levels of platelets, level of hydration, a clot size, a clot shape, and/or a clot location in the vasculature.

In some embodiments, the step of treating of the clot includes retrieving a portion of the clot. The method or use can also include analyzing the retrieved clot and/or one or more fragments of the clot, and selecting a clot treatment step based on analyzing the retrieved clot or analyzing accessing and crossing the clot. However, this example is not so limited and the clot analysis of this embodiment is contemplated to include analyzing any material in communication or otherwise connected with the respective reperfusion device (e.g., serum or any other particulate associated with the clot).

In some embodiments, the step of determining criteria of the clot includes determining one or more quantitative indications selected from one or more of white blood cell levels, red blood cell levels, serum levels, fibrin levels, levels of platelets, level of hydration, clot size, clot location, clot strength, clot elasticity, rate of clot formation or rate of clot lysis. The method or use can include comparing the first and the second clot characteristic quantitative indications to correlation data and determining a selection and/or order of using one or more techniques selected from aspiration, a first reperfusion device, and/or a second reperfusion device.

In some embodiments, a system for treating an ischemic event is disclosed. The system can include a means for providing in vivo analysis information of a clot of the subject having an ischemic event, a means for providing an indication of an individualized treatment protocol for the subject based upon the analysis information, the individualized treatment comprising one or more techniques selected from using aspiration, restoring perfusion using a first reperfusion device, and/or restoring perfusion using a second reperfusion device; and means for treating the clot based on the individualized treatment protocol.

In some embodiments, the first reperfusion device of the system is a stent retriever configured to remove a clot or portions of a clot that are red blood cell rich and the second reperfusion device is a pinch retriever configured to remove a clot or portions of a clot that are fibrin-rich and/or platelet-rich. In some embodiments, if the indication demonstrates that the clot is red blood cell rich, then the individualized treatment protocol includes a means for passing the first reperfusion device by, through, or about the clot and then retracting the first perfusion device while engaging the clot in a lumen of the first reperfusion device to restore reperfusion to the vessel.

In some embodiments, the first reperfusion device is a stent retriever configured to remove a clot or portions of a clot that are red blood cell rich and the second reperfusion device is a pinch retriever configured to remove a clot or portions of a clot that are fibrin-rich and/or platelet-rich. In some embodiments, if the classification demonstrates that the clot is fibrin-rich and/or platelet-rich, then the individualized treatment protocol includes a means for passing the second reperfusion device by, through, or about the clot and then retracting the second perfusion device while pinching the clot to restore reperfusion to the vessel.

In some embodiments, a system for treating an ischemic event is disclosed. The system can include a first reperfusion device for restoring perfusion to an occluded vessel having a clot. The system can include a second reperfusion device for restoring perfusion to the occluded vessel having the clot. The system can include a delivery system for delivering at least one of the first and second reperfusion devices to the clot in the occluded vessel. The system can include a clot analysis system for analyzing the clot of the occluded vessel and determining an individualized treatment protocol. The delivery system can include at least one of a guide catheter, a guidewire, a microcatheter and the like, each of which are operable to delivered through the vasculature to the site of the clot.

In some embodiments, a method or use is disclosed for making a guidewire for an endovascular medical system for treating a clot located in a target vessel. The method or use can include forming a substantially planar distal end of the guidewire; positioning one or more sensors on the guidewire for sensing the clot; and wherein the distal end is substantially planar on the distal end and wider than a remainder of the guidewire proximal thereof, and wherein the predetermined shape is configured to prevent (e.g., to minimize the likelihood of the guidewire tip entering a perforating vessel) the guidewire tip from entering a perforating vessel when the guidewire is delivered to the clot.

In some embodiments, the one or more sensors are positioned on the distal end of the guidewire.

In some embodiments, the one or more sensors are positioned on the guidewire proximal of the distal end.

In some embodiments, the method or use includes positioning one or more sensors on the remainder of the guidewire for sensing the vessel wall.

In some embodiments, the method or use includes positioning one or more sensors symmetrically on opposite sides of the guidewire; and sensing both the clot and the vessel wall.

In some embodiments, the distal end is substantially planar for protecting perforators and to control orientation of the guidewire relative to clot.

In some embodiments, the distal end is substantially planar for receiving the one or more sensors.

In some embodiments, the method or use includes cutting a predetermined shape into the distal end of the guidewire.

In some embodiments, the sensors are near infrared (NIR) sensors configured to transmit an NIR signal from between proximal and distal ends of the guidewire.

In some embodiments, the one or more sensors are impedance sensors disposed on an outer surface of the guidewire.

In some embodiments, the one or more sensors are Raman spectroscopy sensors disposed on an outer surface of the guidewire and operable to transmit and collect certain ranges of the electromagnetic spectrum.

In some embodiments, the sensors are one or more fiberoptic strands or bundles disposed on an outer surface of the guidewire and operable to transmit and collect certain ranges of the electromagnetic spectrum.

In some embodiments, a method or use is disclosed for making a guidewire for an endovascular medical system for treating a clot located in a target vessel. The method or use can include forming a substantially planar distal end of the guidewire; cutting a predetermined shape into the distal end of the guidewire, wherein the distal end is wider than a remainder of the guidewire proximal thereof, and wherein the predetermined shape is configured to prevent the guidewire tip from entering a perforating vessel when the guidewire is delivered to the clot.

In some embodiments, the step of forming the substantially planar distal end of the guidewire further includes providing a shaft of memory alloy; and flattening or rendering substantially planar the distal end of the shaft into a paddle-like shape.

In some embodiments, the step of forming the substantially planar distal end of the guidewire further includes grinding a shaft; and flattening or rendering substantially planar the distal end of the shaft into a paddle-like shape.

In some embodiments, the step of cutting the predetermined shape into the distal end of the guidewire includes laser cutting the distal end along a predetermined contour.

In some embodiments, the step of cutting the predetermined shape into the distal end of the guidewire includes stamping, water jetting, pressing, or electrical discharge machining the distal end along a predetermined contour.

In some embodiments, the step of cutting the predetermined shape into the distal end of the guidewire includes stamping the distal end along a predetermined contour.

In some embodiments, the method or use includes adding an outer polymer layer or coat or jacket to the guidewire.

In some embodiments, the layer or coat or jacket includes radiopaque material.

In some embodiments, the layer or coat or jacket is substantially radiopaque.

In some embodiments, the method or use includes tapering a portion of the guidewire so that a proximal end is thicker than the distal end.

In some embodiments, the method or use includes tapering a core of the guidewire so that a proximal end is thicker than the distal end.

In some embodiments, the proximal end of a core of the guidewire is at least 0.004" thicker than the distal end.

In some embodiments, a diameter of the substantially planar distal end is greater than a diameter of a proximal portion proximal of the distal end.

In some embodiments, the diameter of the proximal portion is at least 50% less than the diameter of the distal end.

In some embodiments, the diameter of the proximal portion is at least 0.014" less than the diameter of the distal end.

In some embodiments, the distal end of the guidewire is an atraumatic clot-circumventing configured distal end.

In some embodiments, the distal end of the guidewire includes a planar geometric shape and thickness less than an outer diameter of a remaining non-flattened portion.

In some embodiments, the flattened distal portion has a paddle geometric shape.

In some embodiments, the distal end of the guidewire is an atraumatic clot-circumventing configured distal end that is conformable in the lateral direction complementary to a contour of the inner wall of the target vessel when passed between the inner wall of the target vessel and the clot; and the distal end of the guidewire is capable of elastic recovery to the substantially planar distal end shape after deployment from a microcatheter.

In some embodiments, the method or use includes advancing the guidewire through a microcatheter comprising a proximal end and a distal end. The distal end of the guidewire can be greater than twice the inner diameter of a lumen of the microcatheter after deployment from a microcatheter.

In some embodiments, the method or use includes advancing the guidewire through a microcatheter comprising a proximal end and a distal end. The distal end of the guidewire can be greater than the inner diameter of a lumen of the microcatheter after deployment from a microcatheter.

In some embodiments, use for managing one or more acute ischemic events is disclosed is disclosed, including determining criteria of a clot; classifying the clot based on the criteria and generating a classification; determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and treating the clot based on the individualized treatment protocol.

In some embodiments, the classifying the clot is carried out in vivo.

In some embodiments, the first reperfusion device is a stent retriever and the second reperfusion device is a pinch retriever.

In some embodiments, the classifying the clot comprises one or more of a clinical exam, a blood test, a computerized tomography (CT) scan, a magnetic resonance imaging (MRI) scan, a carotid ultrasound, a cerebral angiogram, and an echocardiogram.

In some embodiments, the determining criteria of the clot includes performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

In some embodiments, the first reperfusion device is a stent retriever configured to remove a clot or portions of a clot that are red blood cell rich and the second reperfusion device is a pinch retriever configured to remove a clot or portions of a clot that are fibrin-rich; and wherein if the classification demonstrates that the clot is red blood cell rich, then the individualized treatment protocol includes passing the first reperfusion device by, through, or about the clot and then retracting the first perfusion device while engaging the clot in a lumen of the first reperfusion device to restore reperfusion to the vessel.

In some embodiments, the first reperfusion device is a stent retriever configured to remove a clot or portions of a clot that are red blood cell rich and the second reperfusion device is a pinch retriever configured to remove a clot or portions of a clot that are fibrin-rich; and wherein if the classification demonstrates that the clot is fibrin-rich, then the individualized treatment protocol includes passing the second reperfusion device by, through, or about the clot and then retracting the second perfusion device while pinching the clot to restore reperfusion to the vessel.

In some embodiments, the determining criteria of the clot further includes interpreting information, by a computing device in operative communication with the clot, about the clot to determine in real-time levels of red blood cell content, white blood cell content, levels of fibrin, a clot size, a clot shape, and/or a clot location in the vasculature; and wherein the use further includes receiving, through a graphical user interface of the computing device, the individualized treatment protocol; monitoring, by the computing device, perfusion of the vessel with the clot; and, alerting, by the computing device, in response to perfusion being restored in the vessel.

In some embodiments, the computing device is linked to a database comprising correlation data for interpreting information about the clot and determining the individualized treatment protocol; wherein the database is remote from the computing device.

In some embodiments, the determining criteria of the clot includes delivering a catheter to a site of the clot in the vasculature; taking a first reading of the clot by a using instrumentation for near infrared spectroscopy (NIR) coupled to the catheter at a first location of the site of the clot in the vasculature; and generating a spectrum from the first reading, whereby the spectrum relates to at least one of a chemical composition and physical properties of the clot.

In some embodiments, the determining criteria of the clot further includes interpreting information contained in the spectrum to determine in real-time at least one of levels of red blood cell content, white blood cell content, levels of fibrin, a clot size, a clot shape, and a clot location in the vasculature.

In some embodiments, the use includes taking a second reading of the clot by using the instrumentation for NIR at a second location distal or proximal of the clot and the first location; generating a spectrum from the second reading, whereby the spectrum of the second reading relates to at least one of a chemical composition and physical properties of the clot; and interpreting information contained in the spectrum of the first reading and the second reading to determine in real-time at least one of levels of red blood cell content, levels of white blood cell content, levels of fibrin, a clot size, a clot shape, and a clot location in the vasculature.

In some embodiments, the determining criteria of the clot includes delivering a catheter to a site of the clot in the vasculature; taking a first reading of the clot by a using instrumentation for Raman spectroscopy coupled to the catheter at the site of the clot in the vasculature; and generating a spectrum from the first reading, whereby the spectrum relates to at least one of a chemical composition and physical properties of the clot.

In some embodiments, the determining criteria of the clot further includes interpreting information contained in the spectrum to determine in real-time at least one of levels of red blood cell content, white blood cell content, levels of fibrin, a clot size, a clot shape, and a clot location in the vasculature.

In some embodiments, the use includes taking a second reading of the clot by using the instrumentation for Raman spectroscopy at a second location distal or proximal of the clot and the first location; generating a spectrum from the second reading, whereby the spectrum of the second reading relates to a chemical composition and/or physical properties of the clot; and interpreting information contained in the spectrum of the first reading and the second reading to determine in real-time at least one of levels of red blood cell content, white blood cell content, levels of fibrin, a clot size, a clot shape, and/or a clot location in the vasculature.

In some embodiments, the treating of the clot comprises retrieving a portion of the clot, further including analyzing the retrieved clot and/or one or more fragments of the clot, and selecting a clot treatment step based on analyzing the retrieved clot or analyzing accessing and crossing the clot.

In some embodiments, the determining criteria of the clot includes determining one or more quantitative indications selected from one or more of white blood cell levels, red blood cell levels, serum levels, fibrin levels, clot size, clot location, clot strength, clot elasticity, rate of clot formation or rate of clot lysis.

In some embodiments, the use includes comparing the first and the second clot characteristic quantitative indications to correlation data and determining at least one of a selection and order of using one or more techniques selected from aspiration, a first reperfusion device, and/or a second reperfusion device.

In some embodiments, use is disclosed of any system of this disclosure for treating an ischemic event, the system including a first reperfusion device for restoring perfusion to an occluded vessel having a clot; a second reperfusion device for restoring perfusion to the occluded vessel having the clot; a delivery system for delivering at least one of the first and second reperfusion devices to the clot in the occluded vessel; and a clot analysis system analyzing the clot of the occluded vessel and determining an individualized treatment protocol using at least one of the first and the second reperfusion devices.

In some embodiments, use is disclosed of any previously described system for treating an ischemic event, the system including means for providing in vivo analysis information of a clot of the subject having an ischemic event; means for providing an indication of an individualized treatment protocol for the subject based upon the analysis information, the individualized treatment comprising one or more techniques selected from using aspiration, restoring perfusion using a first reperfusion device, and/or restoring perfusion using a second reperfusion device; and means for treating the clot based on the individualized treatment protocol.

In some embodiments, use is disclosed of any previously described catheter for analyzing a clot in a blood vessel.

In some embodiments, use is disclosed of any previously described system for managing one or more acute ischemic events, including delivering a catheter to a site of a clot in the vasculature, the catheter including a lumen having a proximal end and a distal end; and a spectroscopic sensing device connected to the distal end, the spectroscopic sensing device configured to measure properties of the clot through the distal end of the catheter; taking a first measurement of the clot using the spectroscopic sensing device at a first location of the site of the clot in the vasculature; and generating a spectrum from the first measurement, whereby the spectrum relates to at least one of a chemical composition and physical properties of the clot.

In some embodiments, the catheter used includes a window portion adjacent the distal end; and an opaque absorbent portion adjacent the window portion.

In some embodiments, the use includes advancing the distal end of the catheter distal of the clot; and then retracting the distal end of the catheter backwards through the clot while simultaneously spinning the catheter to produce a spectral map over a length of vessel that is occluded by the clot.

In some embodiments, the use includes ascertaining one or more physical properties of the clot by measuring different spectral features of the clot based on the spectrum.

In some embodiments, the use includes interpreting information contained in the spectrum to determine in real-time at least one of levels of red blood cell content, white blood cell content, levels of fibrin, a clot size, a clot shape, and a clot location in the vasculature.

In some embodiments, the use includes taking a second measurement of the clot using the spectroscopic sensing device at a second location distal or proximal of the clot and the first location; and generating a spectrum from the second measurement, whereby the spectrum of the second measurement relates to at least one of a chemical composition and physical properties of the clot.

In some embodiments, the use includes the step of taking the first measurement or the second measurement includes emitting light from the spectroscopic sensing device that penetrates the clot at the respective first or second location; and generating the spectrum that relates to the one of chemical composition and physical properties of the clot exposed to the emitted light of the spectroscopic device.

In some embodiments, the use includes interpreting information contained spectral bands of the spectrum of the first or second measurement to determine in real-time at least one of levels of red blood cell content, levels of white blood cell content, levels of fibrin, a clot size, a clot shape, and a clot location in the vasculature.

In some embodiments, the use includes rotating the catheter 360° and scanning inside of the vessel of the clot to generate a 360° scan.

In some embodiments, the use includes pulling the catheter tip backwards, after being initially placed distal to the thrombus, through an occlusion whilst simultaneously spinning.

In some embodiments, the spectroscopic sensing devices further includes a fiberoptic bundle disposed inside the microcatheter and extended up to or adjacent the distal end of the microcatheter, and a mirror oriented at a predetermined angle adjacent or at the distal end; wherein the step of taking the first measurement or the second measurement includes emitting emitted from the fiberoptic bundle; and reflecting the light towards the clot and/or a vessel wall of the vasculature of the clot.

In some embodiments, the predetermined angle of the mirror is approximately 45°.

In some embodiments, the light is reflected towards the vessel wall from the mirror at approximately 90°.

In some embodiments, the spectroscopic sensing device is integrated with the catheter and is configured to emit light capable of penetrating the clot to analyze the clot using near-infrared spectroscopy.

In some embodiments, the spectroscopic sensing device is integrated with the catheter and is configured to emit light capable of penetrating the clot to analyze the clot using Raman spectroscopy.

In some embodiments, the spectroscopic sensing device is a visible light diagnostic device integrated with the catheter and is configured to emit light capable of penetrating and analyzing the clot.

In some embodiments, the use includes classifying the clot based on criteria and generating a classification.

In some embodiments, the step of classifying the clot comprises one or more of a clinical exam, a blood test, a computerized tomography (CT) scan, a magnetic resonance imaging (MRI) scan, a carotid ultrasound, a cerebral angiogram, and an echocardiogram.

In some embodiments, the step of classifying the clot comprises one or more of histological quantification of clot components, mechanical engineering test of the clot.

In some embodiments, the use includes determining criteria of the clot by performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

In some embodiments, the step of determining criteria of the clot further includes interpreting information, by a computing device in operative communication with the clot, about the clot to determine in real-time levels of red blood cell content, white blood cell content, levels of fibrin, a clot size, a clot shape, and/or a clot location in the vasculature; and wherein the use further includes receiving, through a graphical user interface of the computing device, the individualized treatment protocol; monitoring, by the computing device, perfusion of the vessel with the clot; and, alerting, by the computing device, in response to perfusion being restored in the vessel.

In some embodiments, the computing device is linked to a database comprising correlation data for interpreting information about the clot and determining the individualized treatment protocol; wherein the database is remote from the computing device.

In some embodiments, the determining criteria of the clot includes determining one or more quantitative indications selected from one or more of white blood cell levels, red blood cell levels, serum levels, fibrin levels, clot size, clot location, clot strength, clot elasticity, rate of clot formation or rate of clot lysis.

In some embodiments, the use further includes comparing the first and the second clot characteristic quantitative indications to correlation data and determining at least one of a selection and order of using one or more techniques selected from aspiration, a first reperfusion device, and/or a second reperfusion device.

In some embodiments, use is disclosed of calibrating a system for analyzing clots, including providing a database of at least one of a chemical composition and physical properties of one or more clots previously scanned using a spectrophotometer; generating a calibration set of data using the database and a reference analytical method; and correlating the calibration set of data with spectral features of a spectroscopic sensing device of the system for analyzing clots.

In some embodiments, the system for analyzing clots includes a catheter comprising a lumen having a proximal end and a distal end; and the spectroscopic sensing device connected to the distal end, the spectroscopic sensing device configured to measure properties of the clot through the distal end of the catheter.

In some embodiments, the spectroscopic sensing device is integrated with the catheter and is configured to emit light capable of penetrating the clot to analyze the clot using near-infrared spectroscopy (NIRS).

In some embodiments, the spectroscopic sensing device comprises a near infrared region of the electromagnetic spectrum (780 to 2500 micrometers).

In some embodiments, the spectroscopic sensing device is integrated with the catheter and is configured to analyze the clot composition using Raman spectroscopy.

In some embodiments, the spectroscopic sensing device is integrated with the catheter and is configured as a visible light diagnostic device that emits light capable of penetrating the clot to analyze the clot composition.

In some embodiments, use is disclosed of an endovascular medical system with a clot located in a target vessel for managing one or more acute ischemic events, the system including a guidewire extending in a longitudinal direction from a proximal end to a distal end, the distal end being configured to control its orientation relative to the clot and the target vessel, wherein the guidewire comprises one or more sensors disposed on or adjacent the distal end, the one or more sensors configured for sensing properties of the clot in vivo and treating the clot based on the sensed properties.

In some embodiments, use is disclosed for managing one or more acute ischemic events, including delivering a guidewire through a microcatheter to a site of a clot in the vasculature, the guidewire comprising one or more sensors connected to or adjacent a distal portion of the guidewire, the one or more sensors configured to measure properties of the clot in the vasculature; sensing properties of the clot using the one or more sensors at a first location of the site of the clot in the vasculature; and generating an output from the sensed properties, whereby the output relates to at least one of a chemical composition and physical properties of the clot.

In some embodiments, the use includes selecting one or more devices and/or procedural steps to treat the clot based on the output.

In some embodiments, the distal portion of the guidewire is an atraumatic clot-circumventing configured distal end, and wherein the one or more sensors are circumferentially disposed or wrapped about an outer surface of the guidewire.

In some embodiments, the distal portion of the guidewire is a flattened distal portion having a planar geometric shape and thickness less than an outer diameter of a remaining non-flattened portion.

In some embodiments, the use includes positioning at least one of the one or more sensors on a flattened distal portion for sensing properties of the clot; and positioning the other of the one or more sensors on the remaining non-flattened portion for sensing properties of the vessel wall.

In some embodiments, the use includes classifying the clot based on the sensed properties and generating a classification.

In some embodiments, the one or more sensors are near infrared (NIR) sensors disposed on an outer surface of the guidewire.

In some embodiments, the one or more sensors are impedance sensors disposed on an outer surface of the guidewire.

In some embodiments, the one or more sensors are impedance sensors disposed on an outer surface of the guidewire.

In some embodiments, the one or more sensors are Raman spectroscopy sensors disposed on an outer surface of the guidewire and operable to transmit and collect certain ranges of the electromagnetic spectrum.

In some embodiments, the one or more sensors are one or more fiberoptic strands or bundles disposed on an outer surface of the guidewire and operable to transmit and collect certain ranges of the electromagnetic spectrum.

In some embodiments, the use includes ascertaining one or more physical properties of the clot by measuring different spectral features of the clot based on the output.

In some embodiments, the use includes interpreting information contained in the output to determine in real-time at least one of levels of red blood cell content, white blood cell content, platelet content, levels of fibrin, a clot size, a clot shape, a clot density, and a clot location in the vasculature.

In some embodiments, the use includes sensing properties of the clot using the one or more sensors at a second location distal or proximal of the clot and the first location; and
generating an output from the second location, whereby the output of the second location relates to at least one of a chemical composition and physical properties of the clot.

In some embodiments, the use includes classifying the clot based on the output and one or more of a clinical exam, a blood test, a computerized tomography (CT) scan, a magnetic resonance imaging (MRI) scan, an ultrasound scan, a cerebral angiogram, and an echocardiogram.

In some embodiments, the use includes determining criteria of the clot by performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

In some embodiments, the use includes determining criteria of the clot by determining one or more quantitative indications selected from one or more of white blood cell levels, red blood cell levels, serum levels, fibrin levels, clot size, clot location, clot strength, clot elasticity, rate of clot formation or rate of clot lysis.

In some embodiments, use is disclosed of an endovascular medical system for use with a clot located in a target vessel for managing one or more acute ischemic events, the system including a guidewire extending in a longitudinal direction from a proximal end to a distal end, wherein the guidewire comprises a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot.

In some embodiments, use is disclosed for managing one or more acute ischemic events, including delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot; sensing properties of the clot using at least one of the temperature sensors at a first location distal of the clot, a second location in the clot, and a third location proximal of the clot; and generating an output from the sensed properties, whereby the output relates to at least one of a chemical composition and physical properties of the clot.

In some embodiments, the step of sensing properties with the temperature sensors is done simultaneously at each location.

In some embodiments, the use includes selectively positioning the sensors at predetermined locations along the distal end to measure regions of the clot.

In some embodiments, the use includes separating each sensor a predetermined distance at locations along the distal end to measure regions of the clot.

In some embodiments, the distal end of the guidewire comprises an expanded perimeter with an atraumatic clot-circumventing configured distal end in a delivery configuration, and wherein the one or more sensors are disposed about the expanded perimeter.

In some embodiments, the use includes classifying the clot based on the sensed properties and generating a classification.

In some embodiments, the use includes interpreting information contained in the output to determine in real-time at least one of levels of red blood cell content, white blood cell content, levels of fibrin, a clot size, a clot shape, and a clot location in the vasculature.

In some embodiments, the use includes classifying the clot based on the output and one or more of a clinical exam, a blood test, a computerized tomography (CT) scan, a magnetic resonance imaging (MRI) scan, a carotid ultrasound, a cerebral angiogram, and an echocardiogram.

In some embodiments, the use includes determining criteria of the clot by performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

In some embodiments, use is disclosed for managing one or more acute ischemic events, including delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot; sensing properties of the clot using the temperature sensors at a plurality of locations in the clot; and generating an output from the sensed properties, whereby the output relates to at least one of a chemical composition and physical properties of the clot.

In some embodiments, the use includes sensing properties of the clot at a location distal and/or proximal of the clot.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The disclosure will be more clearly understood from the following description of some embodiments thereof, given by way of example only with reference to the accompanying drawings in which:

FIG. 31A illustrates an example guidewire of this disclosure.

FIG. 31B illustrates a cross section view of FIG. 31A taken along section A-A.

FIG. 31C illustrates a cross section view of FIG. 31A taken along section B-B.

FIG. 36 is a table that shows clinical characteristics of the patients in the first study from whom clot fragments were retrieved by endovascular therapy for histopathological analysis.

FIG. 41 shows a bar graph illustrating the percentage RBCs, fibrin and WBCs of the clot fragments retrieved in each pass for every case of the first study.

FIG. 47 shows a flow diagram depicting an example method or use of this disclosure for managing one or more acute ischemic events.

FIG. 49 shows a flow diagram depicting an example method or use of this disclosure for managing one or more acute ischemic events.

FIG. 50 shows a flow diagram depicting an example method or use of this disclosure for managing one or more acute ischemic events.

FIG. 51 shows a flow diagram depicting an example method or use of this disclosure for managing one or more acute ischemic events.

FIG. 52 shows a flow diagram depicting an example method or use of this disclosure for managing one or more acute ischemic events.

FIG. 53 shows a flow diagram depicting an example method or use of this disclosure for managing one or more acute ischemic events.

DETAILED DESCRIPTION

Figure 1:
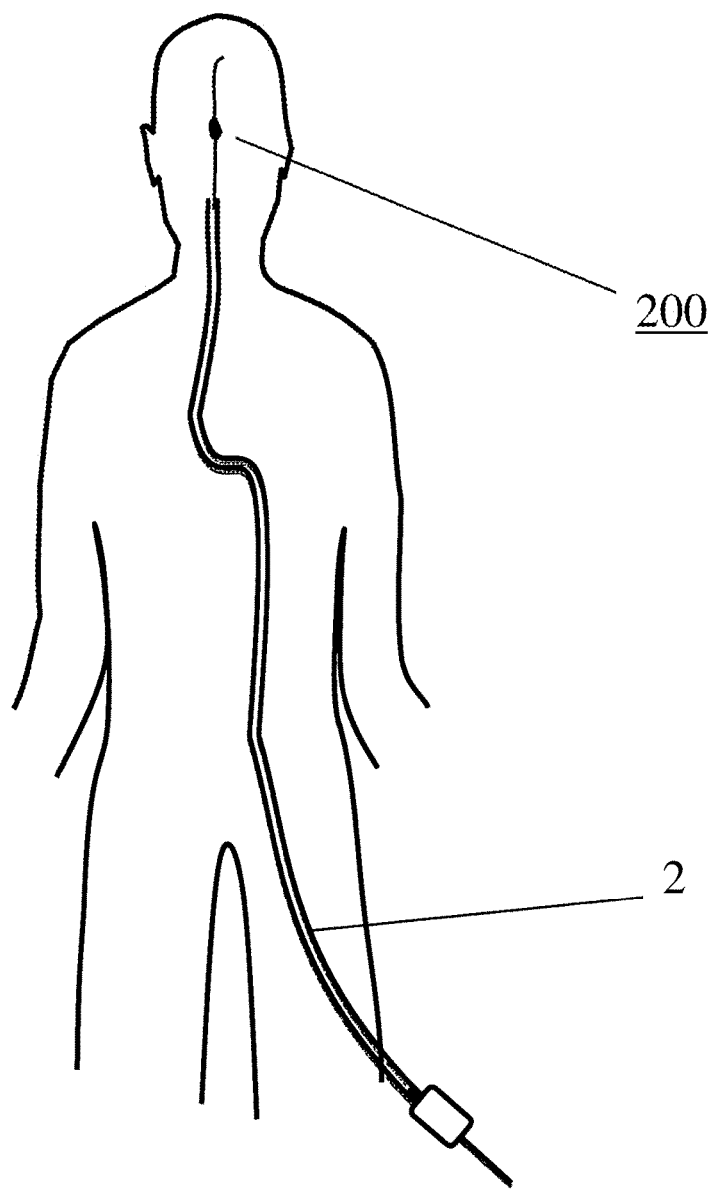
FIG. 1 shows a patient catheterized via femoral access with an example clot retrieval device positioned in a cerebral vessel using the arterial system for its delivery.

Some aspects of the present disclosure relate to method or uses and systems for analyzing and/or classifying acute ischemic events, in vivo and/or in vitro, as well as individualizing a treatment protocol for the particular acute ischemic event. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

As discussed herein, the terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot", "thrombus" or "blockage" are used interchangeably.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

As discussed herein, a "sensor" may be any device or element of a device that is capable of detecting or measuring or reading or storing or otherwise communicating a physical property of the clot or vasculature or other feature of a subject of this disclosure.

As discussed herein, "treatment protocol" may be any plan to resolve an ischemic event observed in a patient, such as restoring perfusion to an occluded vessel. For example, a treatment protocol can include one or a combination of using aspiration, a stent retriever device, a pinch retriever device, thrombolytic infusion, or any other mechanical, fluid, or other means to restore perfusion to the occluded vessel. The treatment protocol can be individualized based on a number of factors for a particular patient, as discussed more particularly below.

An "ASPECT" score means the Alberta Stroke Program Early computed tomography (CT) score (ASPECTS) that includes a 10-point quantitative topographic CT scan score.

As discussed herein, "mRS" means the modified Rankin Scale (mRS) that is a commonly used scale for measuring the degree of disability or dependence in the daily activities of people who have suffered a stroke or other causes of neurological disability. The mRS scale runs from 0-6, running from perfect health without symptoms to death. An mRS score of 0 is understood as no symptoms being observed. An mRS score of 1 is understood as no significant disability is observed and the patient is able to carry out all usual activities, despite some symptoms. An mRS score of 2 is understood as slight disability and the patient is able to look after own affairs without assistance, but unable to carry out all previous activities. An mRS score of 3 is understood as moderate disability whereby the patient can require some help, but is able to walk unassisted. An mRS score of 4 is understood as moderate severe disability and the patient is unable to attend to own bodily needs without assistance or walk unassisted. An mRS score of 5 is understood as severe disability and the patient requires constant nursing care and attention, bedridden, incontinent. An mRS score of 6 is understood as the patient being deceased.

As discussed herein, the term "computed tomography" or CT means one or more scans that make use of computer-processed combinations of many X-ray measurements taken from different angles to produce cross-sectional (tomographic) images (virtual "slices") of specific areas of a scanned object, allowing the user to see inside the object without cutting. Such CT scans of this disclosure can refer to X-ray CT as well as many other types of CT, such as positron emission tomography (PET) and single-photon emission computed tomography (SPECT).

As discussed herein, modified treatment in cerebral ischemia (mTICI) score categorizes the amount of flow restoration after endovascular revascularization. Specifically, the mTICI score was developed from the original Thrombolysis in Cerebral Infarction (TICI) scale by a consensus group in 2013. The recommendations included a name change to better reflect the increasing use of endovascular therapy for stroke, and simplification of the TICI 2 component to less than half of the target vascular territory (mTICI 2a) or more than half (mTICI 2b). Classification: Grade 0: no perfusion; Grade 1: antegrade reperfusion past the initial occlusion, but limited distal branch filling with little or slow distal reperfusion; Grade 2; Grade 2a: antegrade reperfusion of less than half of the occluded target artery previously ischemic territory (e.g. in one major division of the middle cerebral artery (MCA) and its territory); Grade 2b: antegrade reperfusion of more than half of the previously occluded target artery ischemic territory (e.g. in two major divisions of the MCA and their territories); Grade 3: complete antegrade reperfusion of the previously occluded target artery ischemic territory, with absence of visualized occlusion in all distal branches. Although in most cases excellent rates of mTICI 2b or 3 reperfusion can be achieved using current technology, challenging cases remain in which satisfactory reperfusion is not achieved despite several passes and manipulations of the thrombectomy device in a large percentage of cases (e.g., approximately 20% or more cases). The solution of this disclosure provides systems and method or uses for all types of cases, including the approximately 20% or more excluded under current approaches.

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures. As an example, FIG. 1 depicts a schematic representation of the catheterization of a patient with a clot retrieval device 200 via the femoral artery with a microcatheter 10. Example device 200 can restore blood flow in the neurovascular by removing thrombus in patients experiencing ischemic stroke within a certain period of time from symptom onset (e.g., 8 hours, 12 hours, 24 hours, etc.).

Figure 2:
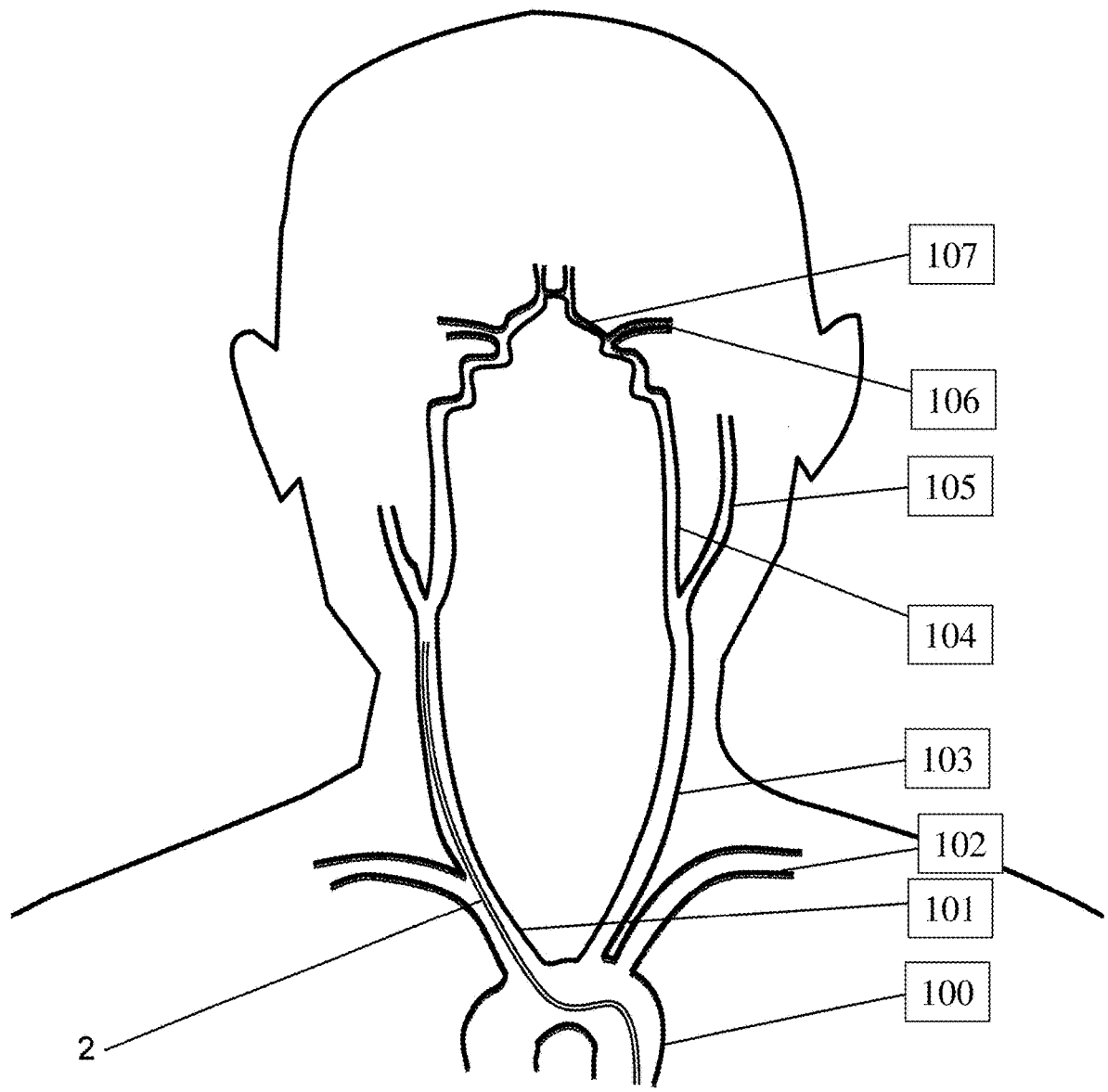
FIG. 2 shows certain anatomy of cerebral arteries above the aortic arch leading to the brain.

FIG. 2 shows a schematic representation of certain example cerebral vessels. Vessel 100 is the Aorta. Vessel 101 is the brachiocephalic artery. Vessel 102 is the subclavian artery. Vessel 103 is the common carotid artery. Vessel 104 is the internal carotid artery. Vessel 105 is the external carotid artery. Vessel 106 is the middle cerebral artery. Vessel 107 is the anterio-cerebral artery. The microcatheter 10 from FIG. 1 is shown with its distal end in the common carotid artery. In the more detailed drawings of the invention the details of the access site will not be shown but in general access and delivery is in accordance with FIG. 1 and/or FIG. 2. In addition, device 200 can be delivered through the vascular in the wrist (radially) or directly by accessing the carotid artery. Device 200 can be designed for use in the anterior and posterior neurovasculature in vessels such as the internal carotid artery, the M1 and M2 segments of the middle cerebral artery, the vertebral artery, and the basilar arteries. Device 200 can be delivered endovascularly under fluoroscopic guidance in a similar manner to that of other neurovascular clot-retrieval systems.

Once across the site of vessel occlusion, the stent-like element of device 200 is deployed to entrap the clot and allow it to be retrieved, hence restoring blood flow. Device 200 can be a dual-layer stent retriever, with articulating petals, and a distal capture zone for effectively trapping, retaining, and removing various clot types to restore blood flow in patients with AIS secondary to large-vessel occlusion. Device 200 can be available in two lengths, 5×21 mm and 5×33 mm.

Figure 3:
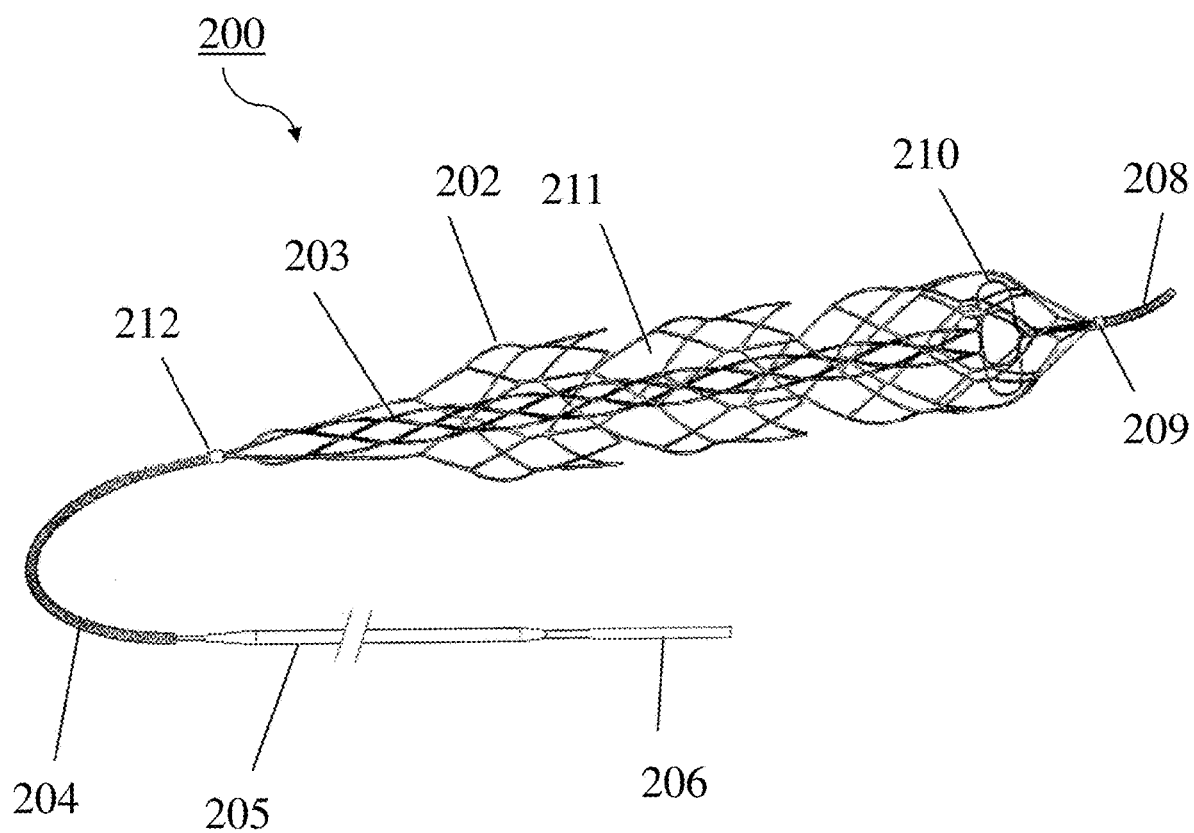
FIG. 3 shows an isometric view of an example stent retriever device of this disclosure.

FIG. 3 shows one embodiment of an example stent retriever device 200 of this disclosure. Device 200 can be understood as including features more clearly described in U.S. Pat. Nos. 8,777,976; 8,852,205; 9,402,707; 9,445.829; and 9,642,639, each of which are incorporated by reference in their entirety as if set forth verbatim herein. Device 200 can have an elongate shaft 206. Shaft 206 can have a distal end that extends interior of the artery and a proximal end that extends exterior of the artery. Shaft 206 can also have a clot engaging portion configured at its distal end having an outer expandable member 202 and an inner expandable member 203 to facilitate restoration of blood flow through the clot after device 200 is deployed. Members 202 and 203 can be configured to have a collapsed configuration for delivery and an expanded configuration for clot retrieval, restoration of perfusion, and fragmentation protection in general.

Shaft 206 may be a tapered wire shaft, and may be made of stainless steel, MP35N. Nitinol or other material of a suitably high modulus and tensile strength. Shaft 206 has a coil 204 adjacent its distal end and proximal of the outer member and inner tubular member. The coil may be coated with a low friction material or have a polymeric jacket positioned on the outer surface. Sleeve 205 may be positioned on shaft 206 adjacent coil 204. Sleeve 205 may be polymeric and may be positioned over the tapered section of shaft 206.

The outer member 202 is configured to self-expand upon release from a microcatheter to a diameter larger than that of the inner tubular member 203. Expansion of the outer member 202 causes compression and/or displacement of the clot during expansion for purposes of restoring perfusion to the vessel. A radiopaque coil 208 (which may be platinum or gold or an alloy of same) is positioned over the distal end of member 203 and butts against the distal collar 209 of the outer member 202, where it is connected by an adhesive joint to the collar 209. Inlet openings of outer member 202 can provide the primary movement freedom available to the clot and so the expansion of the outer member 202 urges the clot into the reception space 211 and outer member 202 can have multiple inlet mouths to accept the clot. Optionally expanded distal struts 210 can be included with the inner member 203 and function as an additional three-dimensional filter to prevent the egress of clot or clot fragments.

Figure 4:
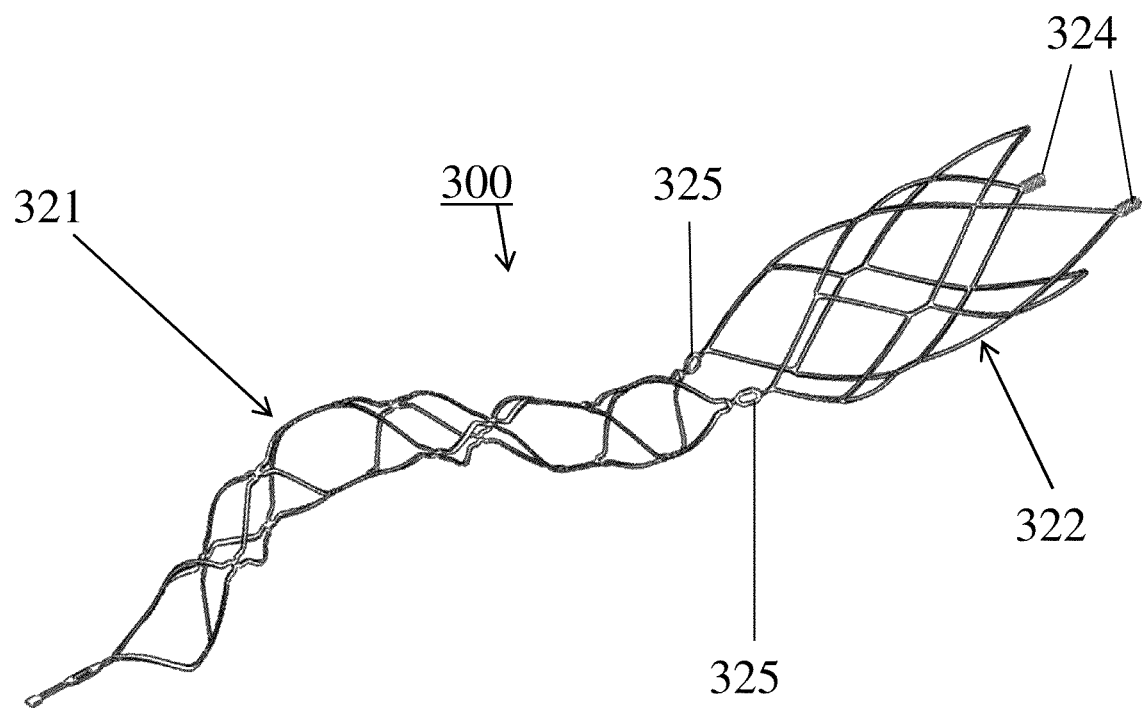
FIG. 4 is a perspective view of a pinching retriever device according to an embodiment of this disclosure.

Referring to FIG. 4 there is illustrated an example pinching retriever device 300 according to an embodiment of this disclosure that can be configured for removing fibrin rich and/or platelet rich clots. Device 300 can be understood as including features more clearly described in U.S. application Ser. No. 16/021,505, now U.S. Publication No. 2019/0000492 A1 published Jan. 3, 2019, which is incorporated by reference in its entirety as if set forth verbatim herein. Device 300 can include a proximal pinch section 321, a distal section 322, distal marker coils 324 and radiopaque markers 325. The proximal pinch section 321 can be heat set into a spiral shape having the following features: spiral pitch—14 mm (within a range of 10-25 mm); spiral outer diameter—5 mm (within a range of 4.0 to 10 mm); and the spiral typically may form a 360° curve, or range from 180 to 720°. A longitudinal center axis of the distal barrel section 322 may be offset from a center line of the spiral to assist in achieving uniform (low strain) connection between the sections.

Device 300 can have an expandable structure with a constrained delivery configuration, an expanded clot engaging deployed configuration, and an at least partially constrained clot pinching configuration, whereby at least a portion of the expandable structure is configured to engage the clot in the expanded deployed configuration and to pinch clot on movement from the deployed configuration to the clot pinching configuration. The distal end of device 300 can have a spiral section orientated so that it is perpendicular to the proximal face of the barrel section. In this orientation, both the struts connecting the spiral section to the barrel section are equal length and have equivalent levels of strain regardless of the cut pattern orientation on the heat forming mandrel. In other embodiments, the spiral section may be orientated at an angle to the barrel section. Device 300 can include staggering of the radiopaque markers 325 as well as longitudinal staggering of the markers. The proximal end of the pinch section of the device 300 in some cases is attached to a shaft (similar to device 200) using a mechanical locking system.

Figure 5:
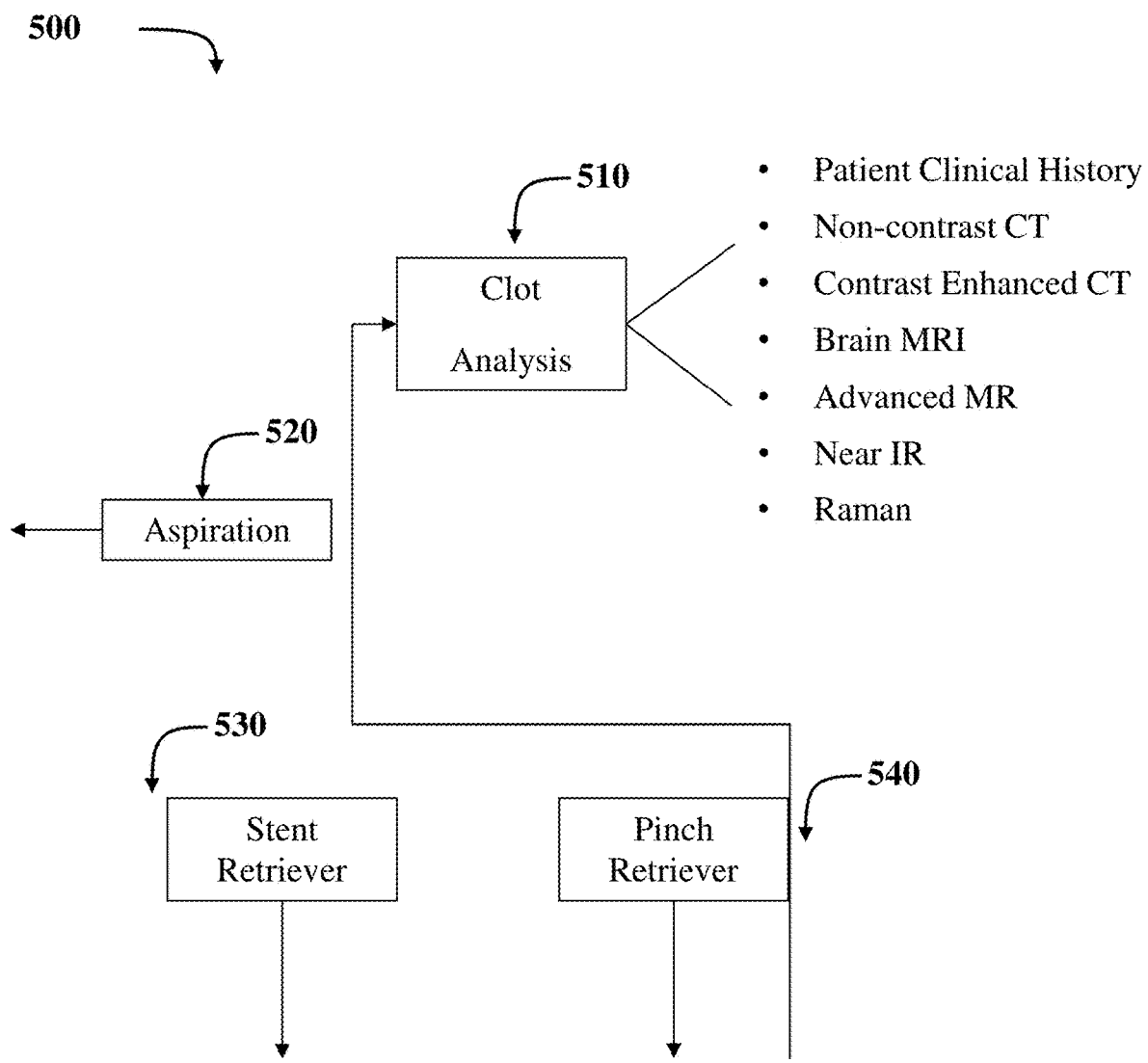
FIG. 5 is a schematic overview of an example of this disclosure.

Turning to FIG. 5 is a graphical overview of one embodiment of the method or use 500. As can be seen, one step of method or use 500 can include clot analysis 510. Clot analysis 510 can include a variety of some or all of a range of steps, without limitation: considering the patient's clinical history, stroke severity, such as the National Institute of Health Stroke Severity (NIHSS) clinical exam and/or neurological exam. Steps of clot analysis 510 can also include blood tests, non-contrast computerized tomography (CT) scan, including quantitative method or uses to analyze stroke severity, such as Alberta stroke program early CT score (e.g., ASPECTS), and automatic assessments of ASPECTS using software (e-ASPECTS).

The clinical history of the patient may include factors such as whether the patient is aged between 18 years and 85 years; an mRS score of 0 or 1; angiographic confirmation of an occlusion of an internal carotid artery (ICA) (including T or L occlusions). M1 or M2 MCA, VA, or BA with mTICI flow of 0-1; MRI criterion: volume of diffusion restriction visually assessed≤50 mL.; CT criterion that includes an ASPECTS score of 6 to 10 on baseline CT or CTA-source images, or, volume of significantly lowered CBV≤50 mL; life expectancy likely less than 6 months; females who were pregnant or breastfeeding; history of severe allergy to contrast medium; known nickel allergy at time of treatment; known current use of cocaine at time of treatment; patient has suffered a stroke in the past 3 months; the patient presents with an NIHSS score<8 or >25 or is physician assessed as being in a clinically relevant uninterrupted coma; the use of warfarin anticoagulation or any Novel Anticoagulant with International Normalized Ratio (INR) >3.0; platelet count<50,000/μL; glucose<50 mg/dL.; any known hemorrhagic or coagulation deficiency; unstable renal failure with serum creatinine>3.0 or Glomerular Filtration Rate (GFR)<30; patients who received a direct thrombin inhibitor within the last 48 hours; a partial thromboplastin time (PTT) less than 1.5 times the normal to be eligible; patients with severe hypertension on presentation (SBP>220 mmHg and/or DBP>120 mm Hg); cerebral vasculitis; improving neurological status; clinical symptoms suggestive of bilateral stroke or stroke in multiple territories; ongoing seizure due to stroke; evidence of active systemic infection; cancer with metastases; CT or MRI evidence of recent hemorrhage on presentation; baseline CT or MRI showing mass effect or intracranial tumor (except small meningioma); suspicion of aortic dissection, presumed septic embolus, or suspicion of bacterial endocarditis; stenosis, or any occlusion, in a proximal vessel that requires treatment or prevents access to the site of occlusion; evidence of dissection in the extra or intracranial cerebral arteries; and/or occlusions in multiple vascular territories (e.g., bilateral anterior circulation, or anterior/posterior circulation).

Step 510 can also include dual energy CT scanning whereby one normal X-ray and also a second less powerful X-ray are used concurrently to make the images. The two X-rays will generate different spectra using different tube potentials. Step 510 can also include an approach that uses CT scanning as described in U.S. application Ser. No. 16/001,427, now U.S. Publication No. 2018/0374128 A1 published Dec. 12, 2019, which is incorporated by reference in its entirety as if set forth verbatim herein.

Step 510 can also include an MRI and/or advanced MR images of the patient's brain to evaluate the clot. Advanced MR images can include sophisticated magnetic resonance imaging techniques that evaluate freedom of water molecule movement in a selected area, the microvascular integrity and hemodynamic characteristics, and the chemical makeup of the clot. Advanced MR can include perfusion imaging, diffusion-weighted imaging, and MR spectroscopy, as well as magnetic resonance angiography, and/or magnetic resonance venography.

Step 510 can also include advanced MR sequences, such as T1-weighted imaging, T2-weighted imaging, diffusion weighted imaging (DWI), proton density imaging, fluid attenuated inversion recovery (FLAIR), Short T1 inversion recovery (STIR), perfusion imaging, apparent diffusion coefficient maps (ADC), gradient echo imaging (GRE), Post-Gadolinium enhancement scans, and/or T2 relaxation time.

Step 510 can also include carotid ultrasound, cerebral angiogram, echocardiogram, intravascular ultrasound (IVUS), and/or optical coherence tomography (OCT).

Step 510 can also include one or more blood tests as well as a non-contrast and/or contrast CT scan of the patient, including the brain area to look at the structures of the brain and evaluate the clot or clots, particularly since no preparation is required for the patient.

Step 510 can also include spectroscopic techniques such as Near Infrared Spectroscopy (NIR) and/or Raman spectroscopy to take readings at one or more locations on the clot and corresponding vasculature to produce a spectrum that relates to the chemical composition and physical properties of the respective occlusion. In this respect, information contained in the spectral bands can be interpreted to provide almost instant analysis of the nature of the material being tested. In certain embodiments, instrumentation associated with the NIR and/or Raman spectroscopy can be included in a microcatheter associated with the delivery system that is delivered to the site of the occlusion in connection with steps 520, 530, and/or 540.

In certain embodiments, in step 510, the occlusion can be scanned in vivo using a catheter having a fiberoptic bundle core connected to a NIR or Raman spectrophotometer. The distal end of the catheter can have a mirror set at 45° on to which light coming from the spectrophotometer via the fiberoptic will be reflected 900 towards the wall of the vessel. Light that is scattered and reflected can be transmitted back to the spectrophotometer via the same mirror and fiberoptic bundle. A spectrum of the transmitted light can be generated, and this information can be used to predict the composition of the material that the light was reflected from. For example, chemical information that corresponds to the bulk composition of the clot and vessel can be deciphered from light absorptions in the near infrared portion of the electromagnetic spectrum and can be used to measure the relative composition of RBC, water, fibrin, or the like within the clot and presence of underlying atheroma in the vessel. Physical information that can be detected in this embodiment can relate to the compactness and organization in the clot resulting from scattering and diffusion of light.

Step 510 can also include analyzing content that may be embedded with a stent retriever after each pass. For example, after a first pass, in certain embodiments the clot, or fragments thereof, can be analyzed in vitro to determine criteria associated therewith. For example, a red blood cell count, a white blood cell count, serum level, fibrin level, or the like can be established to classify the clot. A sample of the clot may then undergo visual or tactile analysis to assist in selection of the proper device used for further procedures.

As a result of analysis stage 510, an indication of clot composition can be provided that advantageously allows classification of the clot in both qualitative and quantitative terms as follows, including the exclusion of presence of a hemorrhagic stroke. Such information can include cellular constituents, extracellular constituents, morphology, organization and distribution of components, permeability, adhesion, water content, resistance to degradation, fibrin cross-link density, fiber diameter, modulus, strain, deformation (e.g., elastic, plastic, viscoelastic), compressibility, and/or fracture behavior. An example table of such indications is provided herein without limitation and other qualitative and/or quantitative indications are contemplated for use with the herein disclosed embodiments:

| Classification Parameter | Range | Procedure 520, 530, 540 Indicator |
|---|---|---|
| Hyperdense middle cerebral artery sign (HMCAS) | Present or absent in relation to contralateral vessel | Present suggestive of aspiration 520 and a stent retriever 530 Absent suggestive of pinch retriever 540 |
| Susceptibility Vessel Sign (SVS) or blooming artefact (BA) | Present or absent in relation to contralateral vessel | Present suggestive of aspiration 520 and a stent retriever 530 Absent suggestive of pinch retriever 540 |
| Catheter angiography, tactile feedback | Subjective force required to pass thrombus | High suggestive of pinch retriever 540 Low suggestive of aspiration 520 and stent retriever 530 |
| Catheter angiography, success of recanalization | Number of attempts, >=1 | >1 suggestive of pinch retriever 540 |
| Clot retrieval, color on gross morphology | White (devoid or RBCs) to dark red (full or RBCs) | Closer to white suggestive of pinch retriever 540. Closer to dark red suggestive of aspiration 520 or stent retriever 530. |
| Clot retrieval, tactile feedback | Soft and friable to Firm and cohesive | Firm clot suggestive of pinch retriever 540. Soft and friable clot suggestive of aspiration 520, stent retriever 530. |

Step 510 can include one or a combination of the foregoing clot analysis embodiments. For example, step 510 can include analyzing criteria of the CT scan and the MRI scan, comparing data analyzed in each to determine levels of red blood cell content, white blood cell content, levels of fibrin, levels of platelets, levels of hydration, a clot size, a clot shape, a clot location in the vasculature, and/or the like. Depending on the classification following step 510, a treatment protocol can be individualized for a patient that dictates whether step 520, 530, and/or 540 is carried out, which advantageously avoids needless use of time from the available timeframe in attempting procedures which are not effective in the circumstances, especially in the context of treatment of acute ischemic stroke. For example, if the red blood cell count and/or the fibrin levels cause the clot to be classified as fibrin-rich and/or platelet-rich, then step 540 may be carried out for a device operable to dislodge and retrieve the fibrin-rich and/or platelet-rich clot. The result of step 510 can also be a decision to either take no action, or to implement the one or more of steps 520, 530, and/or 540.

In some embodiments, step 520 of method or use 500 can include aspiration of the clot through a catheter and/or a syringe and/or one or more electromechanical pump in accordance with the embodiments of this disclosure, including devices and corresponding systems described in WO 2015/189354 A1 dated Dec. 17, 2015, which is incorporated herein by reference. Step 520 can also be initiated based on information (e.g., classification) from the step of clot analysis 510.

In some embodiments, step 530 can include introducing a stent retriever of this disclosure into the vasculature of the patient for intracranial large vessel recanalization in acute stroke in accordance with the embodiments of this disclosure. Example stent retrievers can include the device 200. Step 530 can also be initiated based on information from the step of clot analysis 510.

Step 540 can include introducing a pinch retriever into the vasculature, which can also be informed by clot analysis 510, including devices and corresponding systems as previously described with respect to device 300. It is understood that the pinch retriever associated with step 540 can be operable to be delivered through the vasculature to the site of the clot to pinch at least a portion of the clot body as its expandable element is at least partially collapsed from a fully expanded configuration. The expandable element of the pincher device can be configured to come into contact with at least a portion of the clot, while maintaining the position of the elongate member steadfast and effecting pinching substructure of the device so as to pinch at least a portion of the clot and retracting the clot retrieval device and the pinched occlusive clot from the patient. Step 540 can also be initiated based on information from the step of clot analysis 510.

Each of the steps of method or use 500 can be carried concurrent with clot analysis 510 in a feedback loop so that information from any of the steps of method or use 500 are executed dependent on information relative to the clot being treated. Clot analysis 510 can be performed by example systems and method or uses discussed more particularly in FIGS. 6-11. However, the embodiments depicted in these figures are by no way limiting and other clot analysis approaches are contemplated as included in this disclosure.

Figure 6:
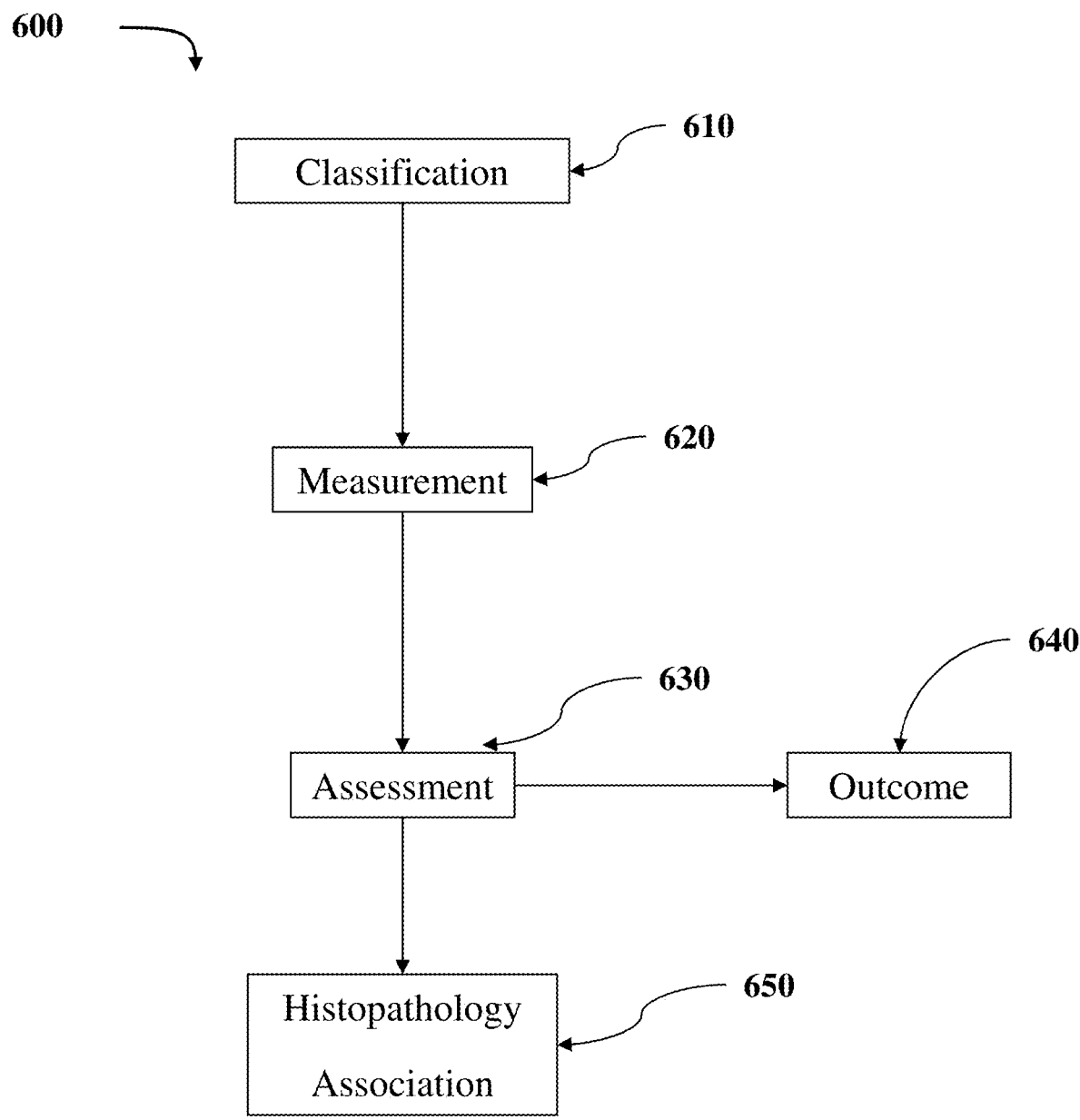
FIG. 6 is a schematic overview of one example of a clot analysis approach of this disclosure.

Turning to FIG. 6 is a graphical overview of one embodiment of the method or use 500. As can be seen, one step of method or use 600 can include classification 610 of the clot present in the vessel. Classification 610 can be carried out by analyzing criteria based on one or more of the embodiments previously described in regards to the clot analysis of method or use 500. Classification 610 can be selected amongst one or more predetermined classifications. For example, classifications of the clot can include levels or concentration of fibrin, red blood cells, white blood cells, serum, friction, or the like.

Step 620 of method or use 600 can include taking one or more measurements of the clot, in vivo and/or in vitro, depending on the method or use employed in classification 610. Once the measurement 620 is taken, the step of assessment 630 can be carried out for the step of histopathology association 650 and/or individualized treatment, device selection for restoring perfusion to the vessel, and corresponding outcome 640.

Figure 7:
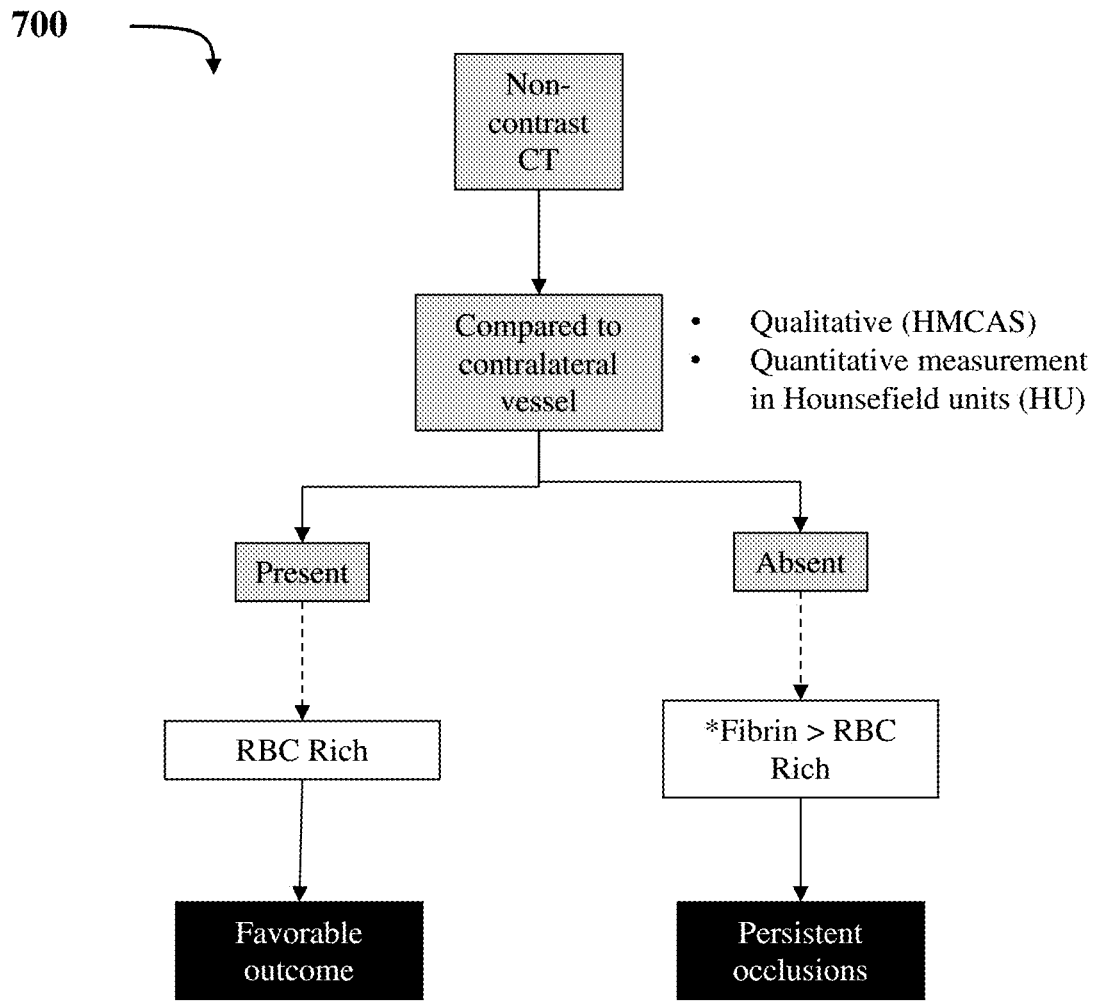
FIG. 7 is a schematic overview of an example of clot analysis using non-contrast CT.

Turning to FIG. 7 is a graphical overview of one embodiment of the method or use 600 of a specific clot analysis embodiment. As can be seen, one step of method or use 600 can include carrying out non-contrast CT of the clot in the vessel. The non-contrast CT is compared to the contralateral vessel, including qualitatively with respect to hyperdense middle cerebral artery signs (HMCAS) and quantitatively in household units (HU). Based on this analysis of method or use 700, it can be determined whether present in the clot is a red blood cell (RBC) rich structure or a fibrin-rich and/or platelet-rich structure, since clots may be either RBC rich or fibrin rich and/or platelet rich. If following the analysis in vivo of method or use 700 it is determined that the clot is RBC rich, then the outcome of thrombectomy using the stent retriever of this disclosure will likely be favorable. Conversely, if following the analysis in vivo of method or use 700 it is determined that the clot is fibrin rich and/or platelet rich, then the outcome of thrombectomy using the stent retriever of this disclosure will likely be unfavorable and instead, a pinch retriever may be preferable.

Figure 8:
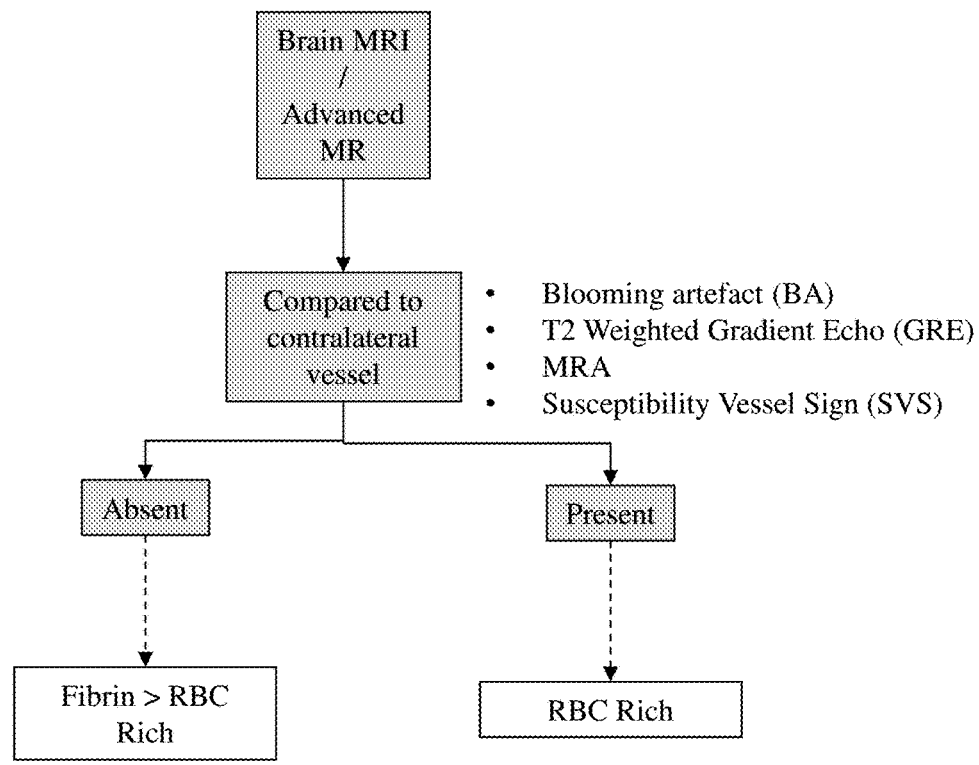
FIG. 8 is a schematic overview of an example of clot analysis using brain MRI and/or advanced MR.

Turning to FIG. 8 is a graphical overview of one embodiment of the method or use 800 of a specific clot analysis embodiment. As can be seen, one step of method or use 800 can include carrying out a brain MRI and/or advanced MR of the clot in the vessel. The brain MRI and/or advanced MR is compared to the contralateral vessel, including qualitatively with respect to blooming artefact (BA), T2 weighted gradient echo (GRE), MRA, and susceptibility vessel sign. Based on this analysis of method or use 800, it can be determined whether present in the clot is a red blood cell (RBC) rich structure or a fibrin-rich and/or platelet-rich structure. If following the analysis in vivo of method or use 800 it is determined that the clot is RBC rich, then the outcome of thrombectomy using the stent retriever of this disclosure will likely be favorable. Conversely, if following the analysis in vivo of method or use 800 it is determined that the clot is fibrin rich and/or platelet rich, then the outcome of thrombectomy using the stent retriever of this disclosure will likely be unfavorable and instead, a pinch retriever may be preferable.

Figure 9:
FIG. 9 is a schematic overview of an example of clot analysis using contrast enhanced CT.

Turning to FIG. 9 is a graphical overview of one embodiment of the method or use 800 of a specific clot analysis embodiment. As can be seen, one step of method or use 800 can include carrying out contrast enhanced CT scan of the brain whereby depending on the scan, it can be determined that a large vessel occlusion (LVO) is present or not to initiate one or more steps of method or useologies of this disclosure.

Figure 10:
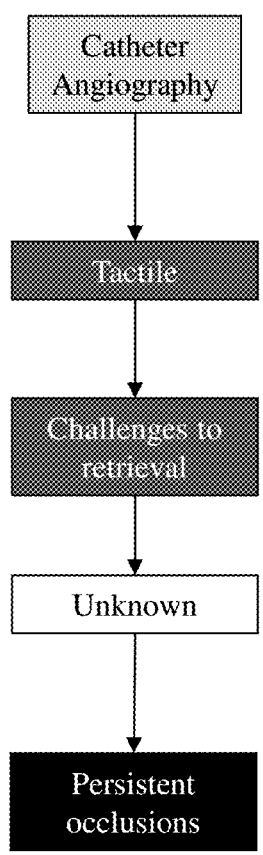
FIG. 10 is a schematic overview of an example of clot analysis using catheter angiography.

Turning to FIG. 10 is a graphical overview of one embodiment of the method or use 1000 of a specific clot analysis embodiment. As can be seen, one step of method or use 1000 can include catheter angiography to visualize the inside, or lumen, of the occluded vessel. Based on this visualization, method or use 1000 can determine if the clot is tactile or exhibits other physical properties. As a result, it can be determined whether there will be challenges to retrieval of the clot, including as a result of tortuosity of the respective vessel and visualized characteristics of the clot. For example, if it is determined that tactility of the clot is related to a fibrin rich and/or platelet rich composition, this can dictate that the correct treatment protocol to restore perfusion may be multiple passes of one or more retriever devices (e.g., a stent retriever and/or a pincher retriever). It is also contemplated that one retriever may retrieve portions of the visualized clot whereas the other retriever may retriever the remainder.

Figure 11:
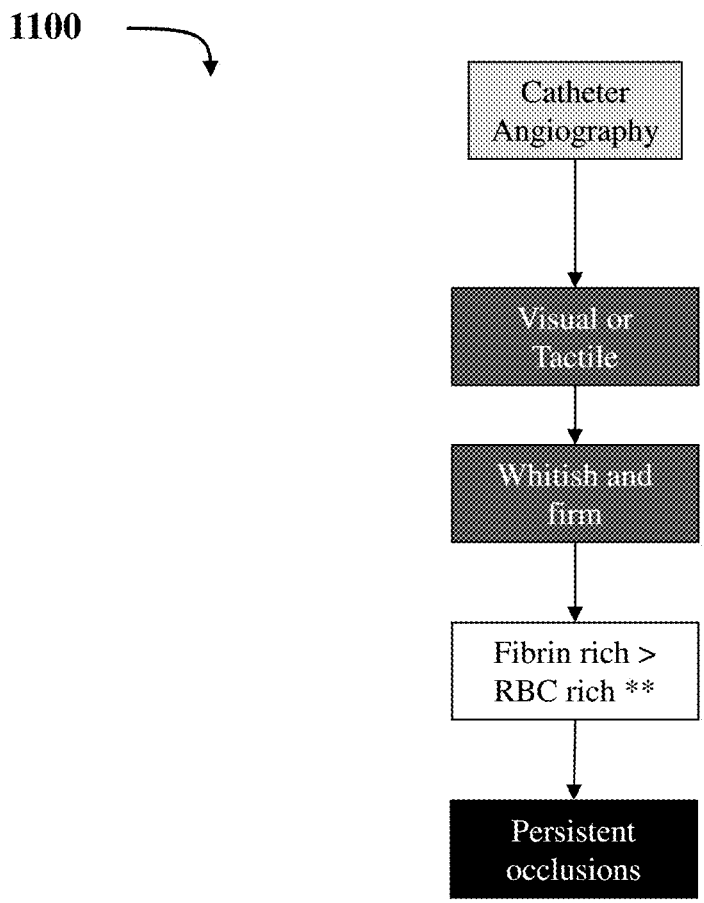
FIG. 11 is schematic overview of an example of clot analysis using catheter angiography.

Turning to FIG. 11 is a graphical overview of one embodiment of the method or use 1100 of a specific clot analysis embodiment. As can be seen, one step of method or use 1100 can include catheter angiography to visualize the inside, or lumen, of the occluded vessel. Based on this visualization, method or use 1100 can visualize the clot as well as determine if the clot is tactile or exhibits other physical properties. As a result, it can be determined features of the clot, for example, based on color or firmness, and this can be a telltale to the extent of the challenges to retrieval of the clot. For example, in some embodiments, firmness or whitish color visualized of the clot can indicate that the clot should be classified as fibrin rich and/or platelet rich, rather than RBC rich. Depending on this analysis, the proper treatment protocol can be selected to restore perfusion to the vessel.

Figure 12:
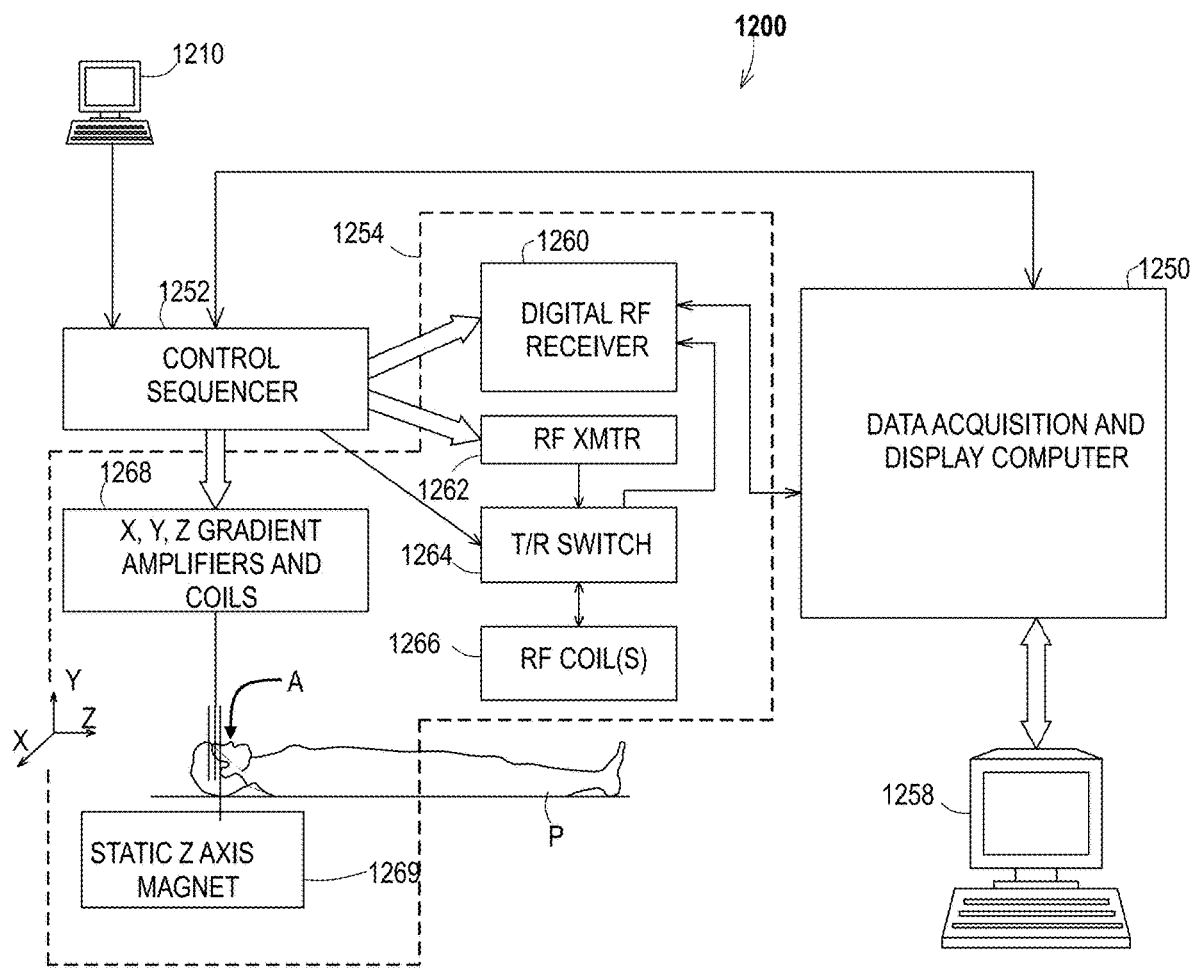
FIG. 12 is a system diagram illustrating an operating environment capable of implementing aspects of the present disclosure in accordance with one or more example embodiments.

FIG. 12 illustrates an example of one embodiment where a brain MRI is conducted during the clot analysis phases. An MRI system 1200, including a data acquisition and display computer 1250 coupled to an operator console 1210, an MRI real-time control sequencer 1252, and an MRI subsystem 1254. The MRI subsystem 1254 may include XYZ magnetic gradient coils and associated amplifiers 1268, a static Z-axis magnet 1269, a digital RF transmitter 1262, a digital RF receiver 1260, a transmit/receive switch 1264, and RF coil(s) 1266. The MRI subsystem 1254 may be controlled in real time by control sequencer 1252 to generate magnetic and radio frequency fields that stimulate magnetic resonance phenomena in a subject P to be imaged, for example to implement magnetic resonance imaging sequences in accordance with various embodiments of the present disclosure. A contrast-enhanced image of an area of interest A of the subject P (which may also be referred to herein as a "region of interest") may be shown on display 1258. The display 1258 may be implemented through a variety of output interfaces, including a monitor, printer, or data storage or even a mobile device.

The area of interest A corresponds to a region of the brain associated with the clot of subject P. The area of interest shown in the example embodiment of FIG. 12 corresponds to a brain region, but it should be appreciated that the area of interest for purposes of implementing various aspects of the disclosure presented herein is not limited to the brain area. It should be recognized and appreciated that the area of interest in various embodiments may encompass various areas of subject P associated with various physiological characteristics.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to MRI implementations or the particular system shown in FIG. 12. One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 13:
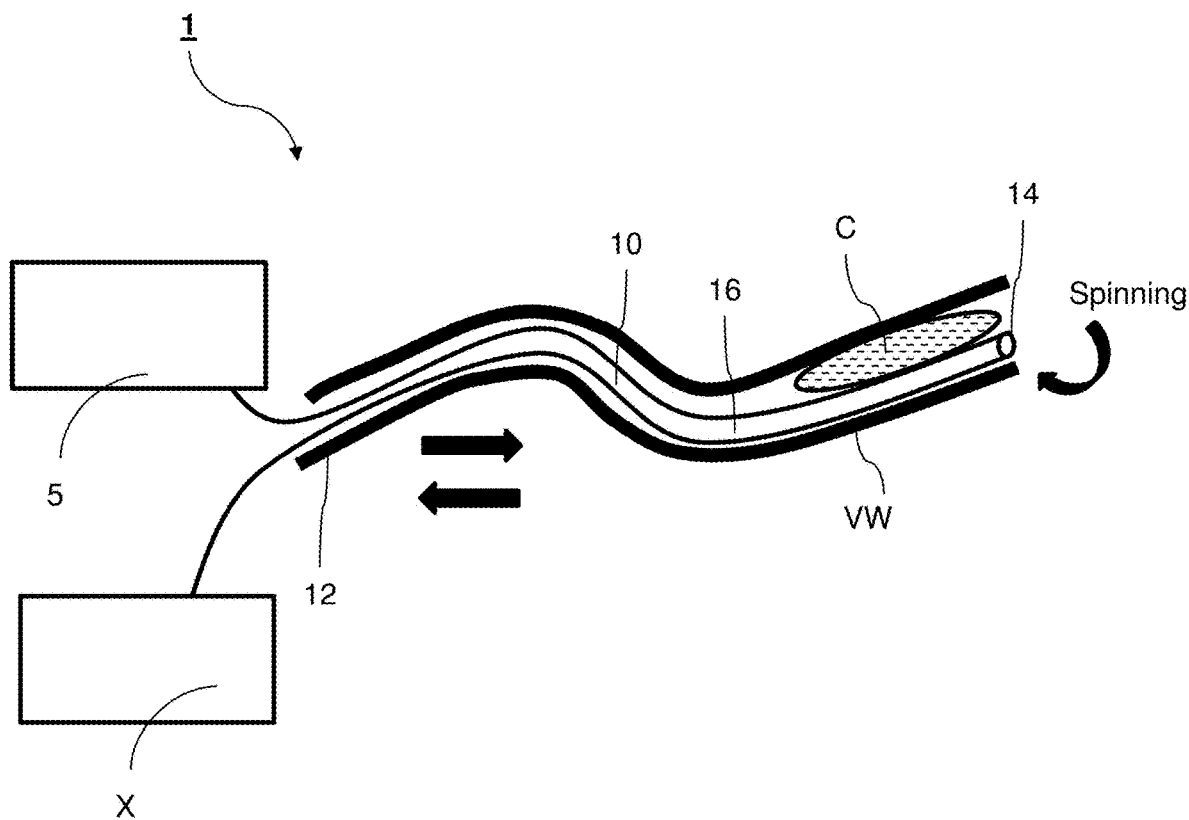
FIG. 13 depicts a system for sensing properties of a clot and surrounding vasculature.

FIG. 13 depicts one example system 1 for sensing properties of a clot C and surrounding vasculature, including the vessel/vessel wall VW. System 1 can include a light source X in communication with a catheter 10. System 1 can include a spectroscopic mechanism or spectrometer 5 in communication with a catheter 10. Throughout this disclosure, the term "spectrometer" or "spectroscopic mechanism" is intended to mean an instrument that is used to separate and/or measure spectral components of a physical phenomenon. In some aspects, spectrometer(s) of this disclosure can show the intensity of light as a function of wavelength or of frequency. A spectrometer of this disclosure can mean a mechanism that utilizes the phenomenon of optical dispersion whereby light can include a continuous spectrum, an emission spectrum, or an absorption spectrum and each element can leave a spectral signature in the pattern of lines observed so a spectral analysis can reveal the composition of the object being analyzed (e.g., a clot, vasculature in a patient, etc.).

Catheter 10 of system 1 can be deliverable to the site of clot C in the vasculature and include a proximal end 12, a distal end 14, and a lumen 16 disposed therebetween. System 1 of this disclosure is particularly useful in analyzing and assessing properties of clot C and surrounding vasculature in vitro prior to clot removal (e.g., by mechanical thrombectomy procedures). Such properties can include cellular content, red blood cells, platelets and white blood cells, non-cellular protein content such as fibrin, von Willebrand factor, collagen, and other components such as serum, calcified deposits, lipids, shape, size, heterogeneity of distribution of constituents, pathogenesis, and age.

One or more of the foregoing properties can be detected by system 1 using spectrometer 5. For example, in certain examples, spectrometer can utilize Near Infrared Spectroscopy (NIR) and/or Raman Spectroscopy. NIR and Raman are both relatively fast, non-destructive light-based techniques with the ability to penetrate several millimeters into clots as well as surrounding tissue and produce a spectrum that relates to the chemical composition and/or physical properties of the respective area exposed to the light source. Information contained in the resultant spectral bands can be interpreted to provide almost instantaneous analysis of the nature of the material being tested, such as chemical composition and/or physical properties of the clot.

Clot C can be scanned with catheter 10 using a fiberoptic bundle core connected to spectrometer 5 and disposed in lumen 16. The distal end 14 can include have a mirror set at a predetermined angle (e.g., 45°) onto which light coming from the spectrometer 5 can be reflected from the mirror (e.g., at an angle of 90°) towards the wall of the vessel VW. It is understood that scattered light and reflected light is transmitted back to the spectrometer 5 via the same mirror and fiberoptic bundle of lumen 16. A spectrum of the transmitted light can then be generated that can include information used to determine material properties and/or chemical composition of the material from which the light was reflected (e.g., clot C, vessel VW, etc.).

Catheter 10 of system 1 can be capable of spinning or being rotated so that a rotational scan of the inside of the vessel VW can be acquired (e.g., a rotational scan of 360°, 180°, or some desired degree of rotation as needed or required). During one procedure, the distal end 14 (e.g., the tip) can be pulled backwards through clot C while also simultaneously being spun or rotated after being initially placed distal to clot C. In so doing, system 1 can generate a spectral map over a predetermined length of vessel VW that is occluded.

As previously described, clots can have different composition and material properties as compared to surrounding blood and vessel walls. Accordingly, a length of the clot C can be ascertained by measuring different spectral features as well as compositional variations in the clot C and surrounding tissue, since each will have different spectral features. In this respect, clot composition and heterogeneity can be measured by system 1. For example, system 1 can detect in vivo whether clot C is platelet rich, fibrin rich, red blood cell rich, etc. System 1 can also be configured to detect water content of the clots. Based on this detecting input from spectrometer 5 used with fiberoptic bundle of lumen 16, system 1 can undertake a clot compositional and/or property analysis for use in selecting the most appropriate treatment to remove the clot C and reperfuse vessel VW.

Figure 23:
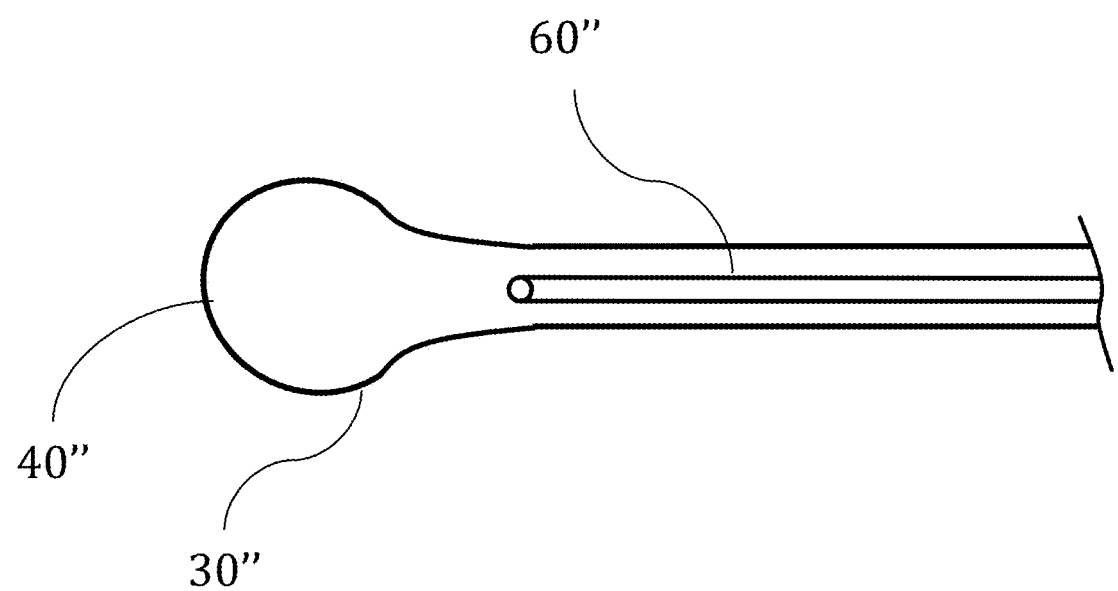
FIG. 23 is an exemplary illustration of an atraumatic clot-circumventing configured distal tip of a guidewire.

In certain examples, for the system 1 to function accurately, a calibration can be required, as further explained in one non-limiting example approach of FIG. 23. For example, a calibration data set can be constructed by analyzing one or more clots with known properties to form a baseline using the instrumentation of system 1. Referencing method or uses contemplated for use in calibrating system 1 can also include histology and water content measurement whereby reference values can be correlated with spectral features using multivariate analysis.

Figure 14:
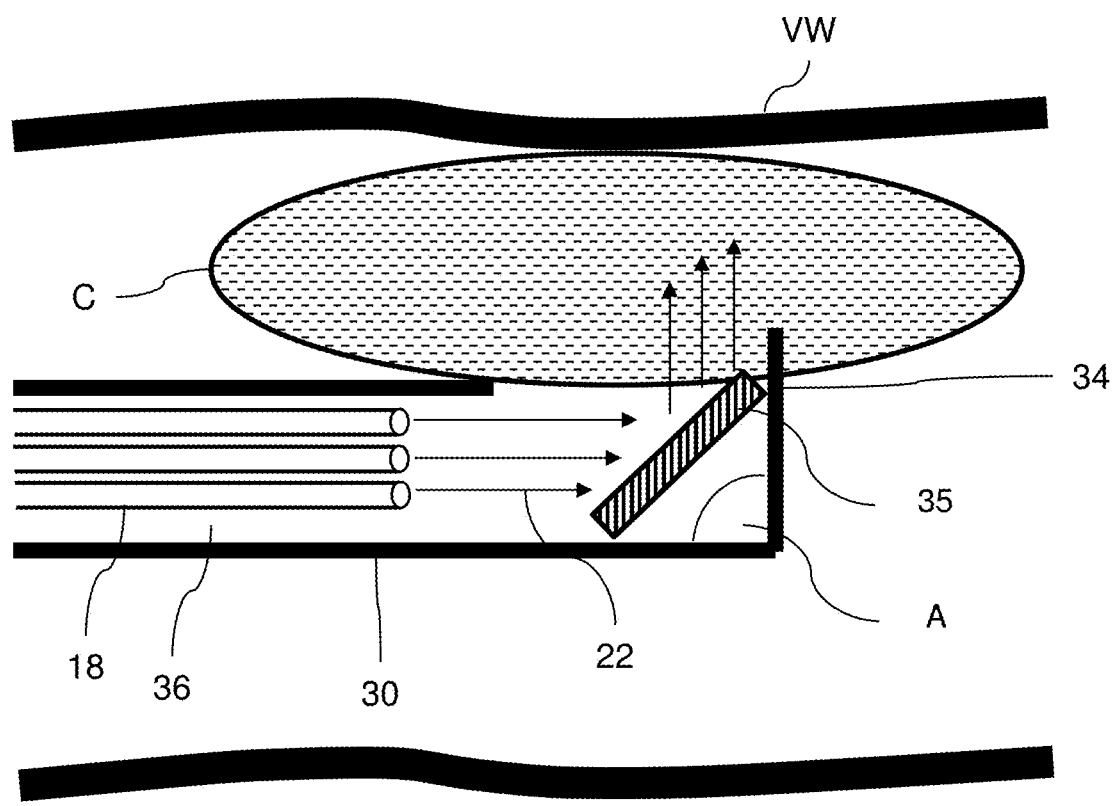
FIG. 14 depicts a system for sensing properties of a clot and surrounding vasculature.

FIG. 14 depicts one example arrangement of system 1 with fiberoptic bundle 18 shown being disposed in lumen 16 positioned within lumen 36 of catheter 30, which can be positioned within lumen 16 of catheter 10. Catheter 30 is a NIR catheter that includes a distal end 34 and a proximal end 32 (not shown) with bundle 18 extended from a spectrometer 5 (not shown, but positioned adjacent proximal end 32). Bundle 18 is capable of emitting incident light 22 towards mirror 35, which is oriented at a predetermined angle A (e.g., 45°) with respect to distal end 34 walls. In turn, light 22 is reflected off mirror 35 towards clot C at a predetermined angle (e.g., 90°). It is contemplated that mirror 35 can be oriented in other orientations with respect to end 34 or the distal end 34 can be arranged as needed or required to emit light 22 on the desired region to be scanned of the patient, including one or more locations of clot C and surrounding vessel wall VW.

Figure 15:
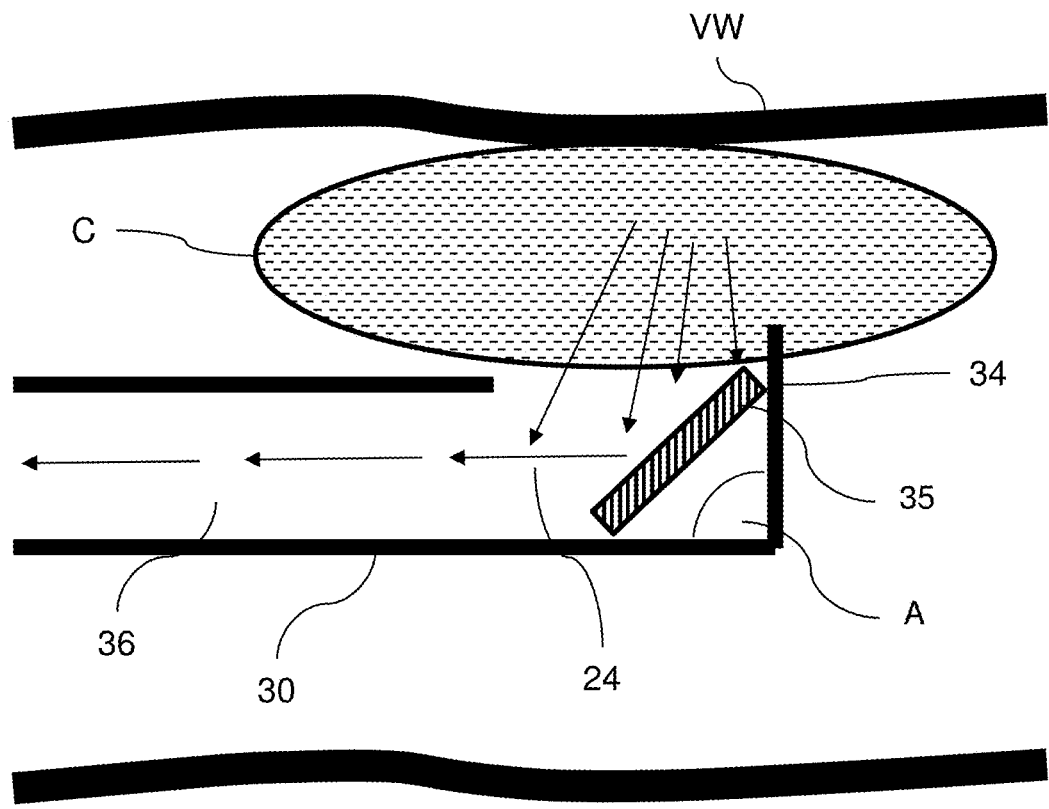
FIG. 15 depicts a system for sensing properties of a clot and surrounding vasculature.

FIG. 15 depicts one example arrangement of system 1 with NIR catheter 30, previously shown in FIG. 14, and with bundle 18 removed for viewing clarity. As can be seen, now light 22 previously emitted from bundle 18 of FIG. 14 is now light 24 that is scattered and/or deflected from clot C and/or surrounding vasculature VW. Light 24 in turn is then deflected into mirror 35 and proximally through lumen 36 of catheter 30 ultimately to spectrometer 5 to generate spectral data for analyzing, classifying, and determining information related to clot C and surrounding vasculature VW.

Figure 16:
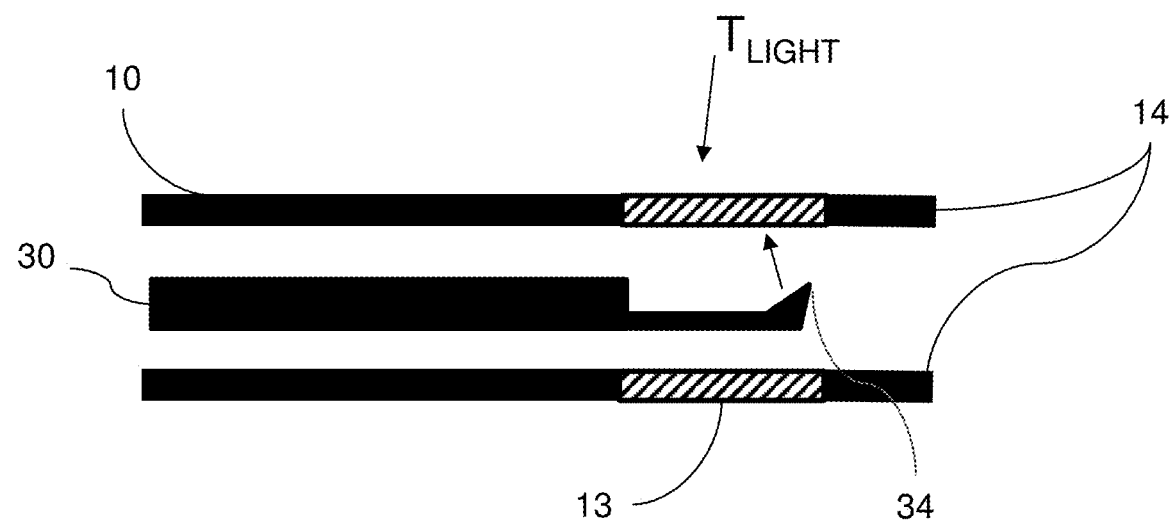
FIG. 16 depicts a system for sensing properties of a clot and surrounding vasculature.

FIG. 16 depicts one example arrangement of system 1 now including both catheter 10 and NIR catheter 30, previously shown in FIGS. 14-15. As shown, catheter 30 can be disposable inside lumen 16 of catheter 10 and translatable therein for use at the site of the clot. As shown, microcatheter 10 of this example can include a window portion or transparent non-opaque, non-absorbent portion 13 adjacent distal end 34. In contrast, the remainder of catheter 10 can be opaque absorbent to the extent light from bundle 18 of catheter 30 is incapable of passing through for sensing composition and/or properties of a sample through portion 30. $T_{LIGHT}$ is shown schematically as being capable of passing through portion 13 between mirror 35 of catheter 30 and vasculature VW and/or clot C of the patient, without being absorbed. Portion 13 can be constructed using one or more transparent or substantially transparent materials, including Polycarbonate, Poly methylmethacrylate (PMMA), and perfluorinated polymers. Catheter 30 can include a near infrared region of the electromagnetic spectrum that can range between 780 to 2500 micrometers.

Figure 17:
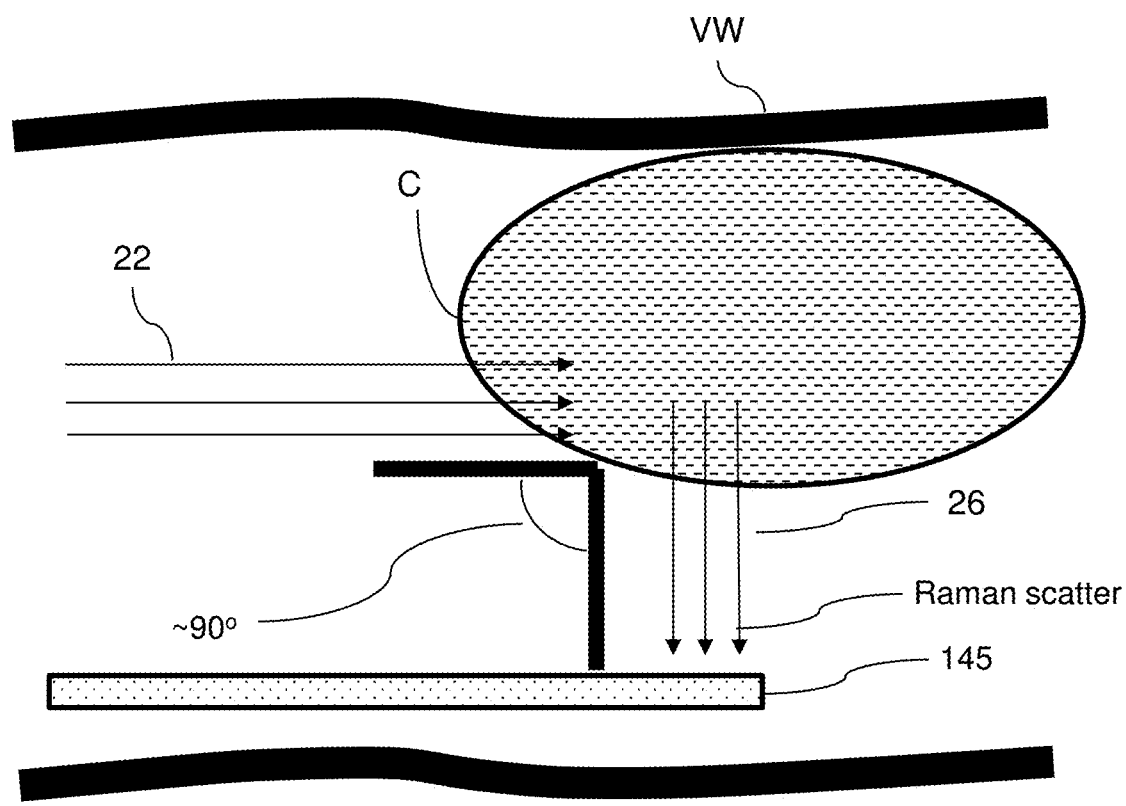
FIG. 17 depicts a system for sensing properties of a clot and surrounding vasculature.

FIG. 17 depicts one example arrangement of system 1 employing a spectrometer 5 utilizing Raman spectroscopy. It is understood that Raman spectroscopy used in system 1, including Raman scattering, can include wavelengths of light 22 being passed through clot C and/or vasculature VW whereby photons 26 from bundle 18 produce an oscillating polarization and Rayleigh scattering can be observed. In this respect, photons 26 of incident light 22 that originate from bundle 18 in catheter 30 (both not depicted for ease of clarity) come off substantially perpendicular to the direction of light 22. Then, photons 26 from clot C can be passed through a fiber optic to a filter for Raman scattering, then through a grate and then in a spectrometer 5 via mechanism 145 for determining information of clot C and/or vessel VW at one or more regions or locations. Light from grate 140 can be returned back to spectrometer 5 through use of one or more mirrors or light deflectors, similar to FIGS. 14-16.

It is understood that the Raman scattered light can be made up of Rayleigh and Raman photons. Further, photons of the Rayleigh scattering light can have equivalent properties as incident light such that filter 135 can be used to remove "identical" photons, so that remaining photons are Raman photons that can then be analyzed for spectral properties. In some examples, a similar mirror as mirror 35 is included with the system of FIG. 17. In other examples, another catheter can be included with catheter 30, similar to FIGS. 15-16, whereby catheter 30 can be disposed within lumen 16 of microcatheter 10.

Figure 18:
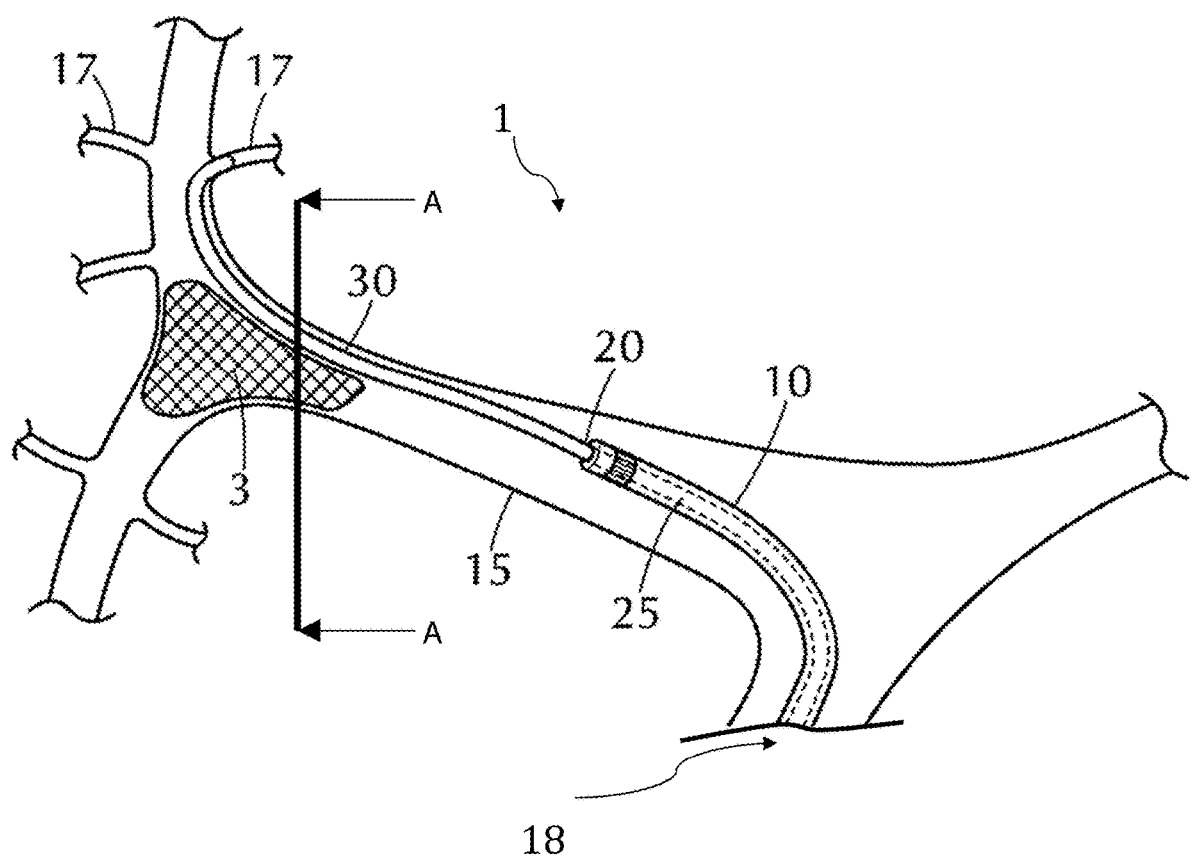
FIG. 18 is a conventional mechanical thrombectomy system including a guidewire having a conventional distal tip or end undesirably introduced into a perforator vessel after crossing through a clot, occlusion or blockage.

During the thrombectomy procedure or treatment a physician or interventionalist endovascularly introduces a guidewire through the vasculature, typically in an artery located in the groin or by direct access through the carotid artery, as shown in FIG. 18. In particular, when advanced across the occlusion or clot 3 first, the guidewire 30 may undesirably: (i) enter a perforator vessel 17 that branches from a target, main or primary artery 15 potentially causing vessel damage and perforation; and/or (ii) cause injury or damage to the vessel tissue when passed across the clot. To minimize or prevent injury to the target vessel tissue and/or perforator vessels, when the guidewire 30 is advanced across the clot 3 prior to the microcatheter 10, the physician or interventionalist may deliberately change or alter the guidewire 30 by bending its distal end. However, shaping or altering of the distal tip or end of the guidewire 30 in such manner is difficult to control by the physician or interventionalist possibly resulting in the shaped or altered distal end or tip being incapable of passing across or around the clot 3 and/or potentially causing deleterious injury or damage to the target vessel tissue when passed (or attempted to be passed) across or around the clot 3. The guidewire 30 is advanced through the vasculature to a location facing a proximal side of the targeted clot 3, blockage or occlusion. Once the guidewire 30 is properly positioned, a microcatheter 10 with an outer diameter typically less than approximately 1.0 mm, tracks over the guidewire 30 passing through a lumen 25 defined axially through the microcatheter 10.

Guidewires commonly used for these types of procedures are relatively small in diameter so that they may easily pass through a lumen having a relatively small inner diameter defining a lumen 25 extending longitudinally through the microcatheter 10. Conventional guidewire 30 outer diameter sizes range from approximately 0.010" to approximately 0.014", while the inner diameter range of the lumen 25 of the microcatheter 10 is between approximately 0.016" and approximately 0.027". Typically, the outer diameter of the guidewire 30 used is 0.014", while the inner diameter of the microcatheter 10 is 0.021". Smaller size guidewires having an approximately 0.010" outer diameter and microcatheters having an inner diameter lumen of approximately 0.016" are sometimes used, particularly in smaller or more distal vessels.

Figure 19A:
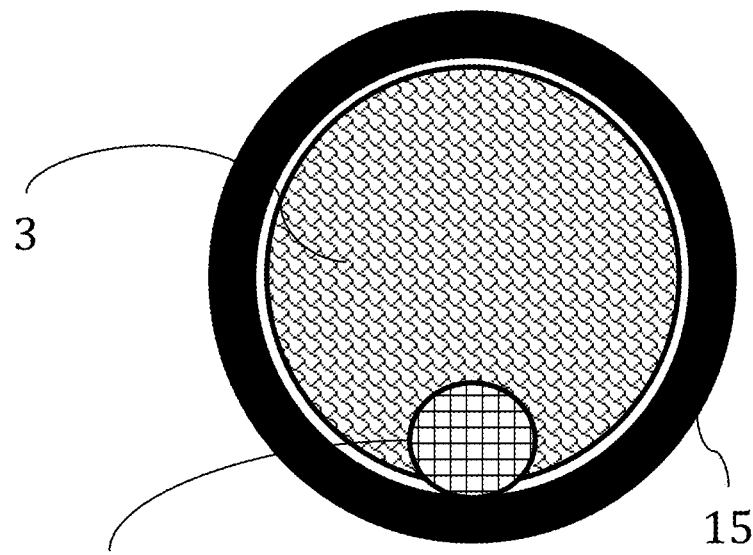
FIG. 19A is a view of a guidewire from FIG. 18 along section A-A.
Figure 19B:
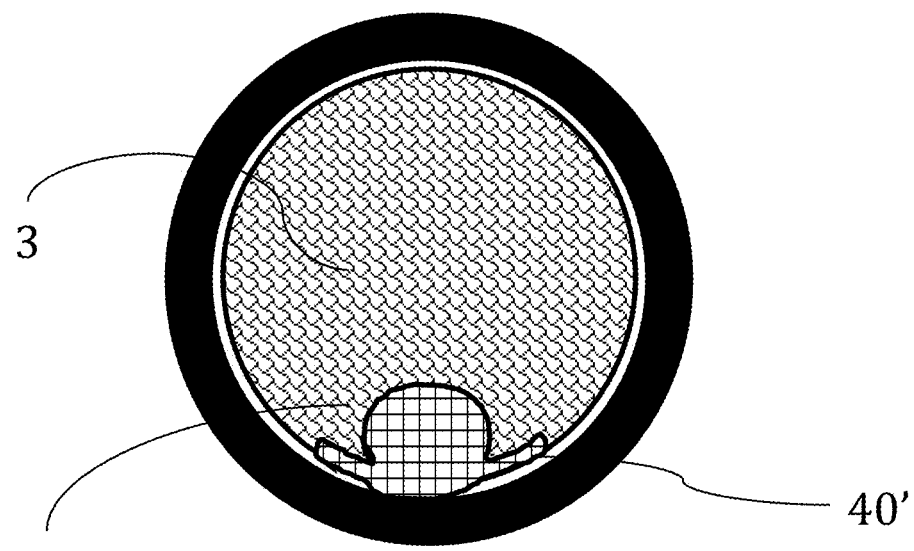
FIG. 19B is a view of another guidewire from FIG. 18 along section A-A.

FIG. 19A is a view of a guidewire 30 from FIG. 18 along section A-A. In particular, in this view it can be seen that guidewire 30 is rounded and has been advanced across the occlusion 3. In contrast, guidewire 30' of FIG. 19B depicts a rounded guidewire with a planar, flattened distal tip 40' that is capable of being orientated in only two configurations, as explained more particularly below.

Figure 20:
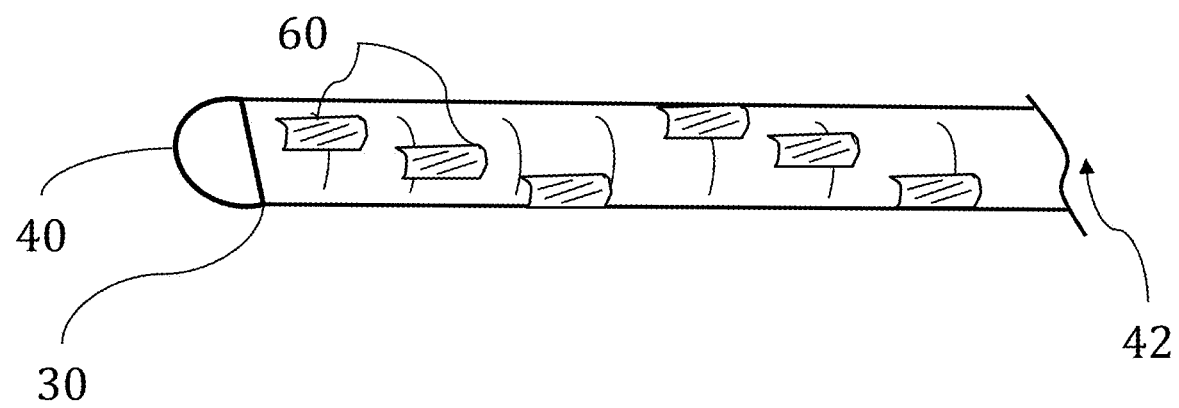
FIG. 20 is an illustration of an example guidewire with sensors for detecting properties of a clot.

FIG. 20 is an illustration of an example guidewire 30 with sensors 60 for detecting properties of clot 30, as previously shown in FIG. 19A. In particular, FIG. 20 depicts six (6) sensors that are substantially rectangular and circumferentially spaced about an outer surface of guidewire 30. The sensors 60 are shown extending proximally from distal tip 40 towards the proximal end of guidewire 30 (see, e.g., FIG. 1). However, the solution of FIG. 20 is not so limited and any number of sensors, whether fewer or more, are contemplated for use as needed or required. Sensor 60 may also be configured with any shape as needed or required. It is understood that guidewire 30 is a conventional guidewire and that sensors 60 could be any of those contemplated within this disclosure, including NIR, Raman spectroscopy, impedance sensors, or fiberoptic strands or bundles operable to transmit and collect certain ranges of the electromagnetic spectrum.

Figure 21:
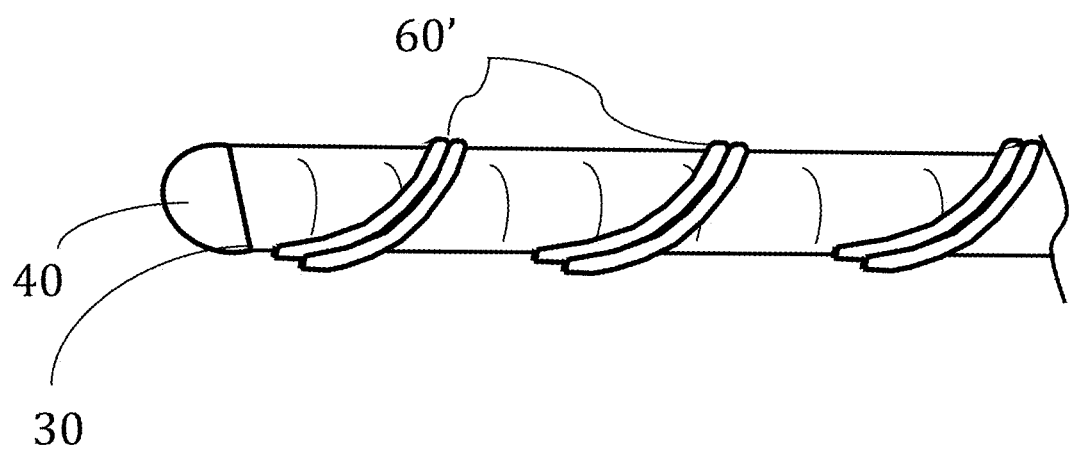
FIG. 21 is an illustration of an example guidewire with sensors for detecting properties of a clot.

FIG. 21 is an illustration of an example guidewire 30 with sensors 60' for detecting properties of clot 30, as previously shown in FIG. 19A. In particular, FIG. 21 depicts sensors 60' that are circumferentially wrapped around and/or spaced about an outer surface of guidewire 30. The sensors 60', similar to sensors 60, are shown extending proximally from distal tip 40 towards the proximal end (not depicted) of guidewire 30. However, the solution of FIG. 16 is not so limited and any number of sensors, whether fewer or more, are contemplated for use as needed or required. Sensor 60 may also be configured with any shape as needed or required.

Figure 22A:
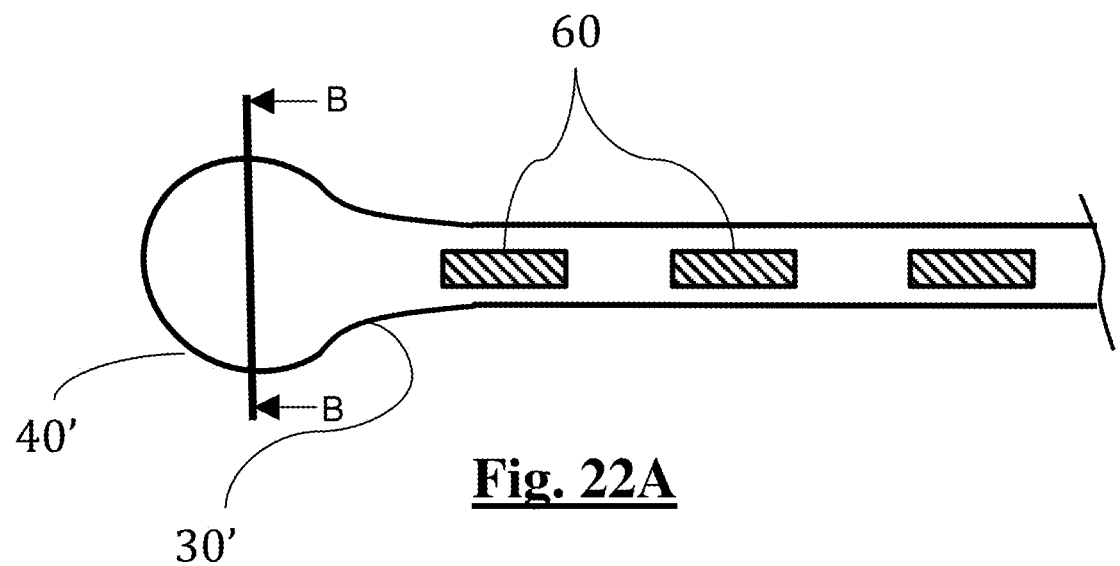
FIG. 22A is an exemplary illustration of an atraumatic clot-circumventing configured distal tip of a guidewire.

FIG. 22A is an exemplary illustration of an atraumatic clot-circumventing configured distal tip 40' of a guidewire 30'. Tip 40' can be a flattened portion of the core wire cut or stamped into a paddle shape, as described more particularly in U.S. patent application Ser. No. 16/003,527, now U.S. Pat. No. 10,667,833 issued Jun. 2, 2020, which is incorporated by reference herein in its entirety as if set forth verbatim. As can be seen, the paddle shaped distal tip 40' is in a relaxed or non-compressed state (not subject to application of an external mechanical force). Rather than pre-forming or pre-shaping the guidewire 30' to a desired geometric shape, the distal tip 40' can have a circular lateral cross-section and/or may alternatively be flattened out and then cut or stamped into a desired geometric shape to form the atraumatic clot-circumventing configured distal end or tip (e.g., as the depicted "planar paddle shape" 40').

Because the guidewire 30 discussed previously in FIGS. 20-21 is round, there is no easy way to control the orientation of the guidewire 30 as to the clot 3 and any sensors 60. To resolve this problem, planar guidewire 30' is basically configured to be oriented only in the depicted flat or planar position of FIG. 22A or a collapsed condition prior to deployment. This is particularly advantageous with guidewire 25' since sensors 60 would be caused to face the clot 60 during use, rather than rotating or moving or otherwise moving in a manner that causes sensors 60 to misread or inaccurately sense properties of clot 60. For example, the sensors 60 of previous FIGS. 20-21 may at times face the vessel wall 15 whereas other times may be half way between the walls 15 and clot 3. To resolve this, rather than developing a complex algorithm to sort out and process the resultant signals, which may not be easy to do and which result in reduced sensing accuracy, the herein disclosed planar guidewire 30', including planar tip 40', can be operable to move between one of two orientations as it crosses the clot as shown in FIG. 14B.

Turning back to FIG. 22A, sensors 60 can be advantageously positioned on both sides of the guidewire 30' and/or aligned with tip 40'. In turn, the resultant clot sensing signals detected through sensors 60 will be much easier to distinguish and process since they will be oriented as either fully facing the clot 3 or fully facing the vessel wall 15.

In this respect, distal tip 40' can be flattened to form a thin support structure or substrate 50, typically having a thickness ranging from approximately 0.0005" to approximately 0.010", preferably the thickness ranges from approximately 0.001" to approximately 0.005". Tip 40' may alternatively be achieved by assembling a pre-formed planar paddle shaped distal end or tip, having the same specified thickness range, on an end of a separate core wire, such as by welding, soldering or bonding. Two separate components assembled or joined together is particularly well suited to applications in which the pre-formed planar paddle and core wire on which the paddle is to be assembled are made of different materials.

Figure 22B:
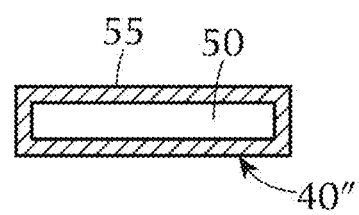
FIG. 22B is a cross section view of FIG. 22A taken along section B-B.

As illustrated in the cross-sectional view in FIG. 22B taken along section B-B of FIG. 22A. An outer covering or layer 55 may be applied to the external surface of the supporting structure 50. Outer covering or layer 55 may comprise one or more coverings, coating layers, or films. For instance, the outer covering or layer 55 may comprise a polymer jacket applied directly to the outer surface of the support structure or substrate 50 with or without a lubricious coating, e.g., a hydrophilic material, applied directly to the outer surface of the polymer jacket. The outer jacket may also contain radiopaque fillers to enhance fluoroscopic visibility of the tip.

The guidewire 30' may be retracted or drawn back through the distal end 20 of the microcatheter 10. In this respect, the distal tip 40' of guidewire 30' can move between collapsed to expanded configuration in a manner akin to that of rolling one's tongue (e.g., in the collapsed configuration, lateral edges of distal end 40' can be in a curled or curved or wrapped state and then can curl or roll towards one another during deployment to the expanded, paddle configuration). Upon exiting from the lumen 25 of the microcatheter 10, the paddle shaped distal end or tip 40" of the guidewire is automatically restored to its former planar relaxed or non-compressed state (not subject to application of an external mechanical force) (as seen in FIG. 22A).

FIG. 23 is an exemplary illustration of an atraumatic clot-circumventing configured distal tip 40" of a guidewire 30", similar to tip 40' of guidewire 30' except for that the guidewire 30" of FIG. 23 includes fiber sensor 60" that can be aligned with the planar, flattened surface of guidewire 30".

In other embodiments, a temperature measurement device is disclosed for sensing temperature readings at different locations in the vasculature, including along and inside a clot. The device can be configured to identify, among other information, clot type or composition of the clot generally or of internal and external regions of the clot. In some examples, the device can be configured to determine clot heterogeneity along the length of the clot. In some examples, the device can be configured to characterize the clot in vivo, for example, to a determine the origin of the clot (e.g., based on temperature readings of the clot it can be determined that the clot is from an atrial appendage or ruptured atherosclerotic plaque).

In some examples, the temperature measurement device can be part of a system for analyzing temperature differentials that in turn can utilize the temperature readings with respect to the clot and surrounding areas to provide information related to the clot to improve treatment. In some embodiments, device can include one or more sensors for sensing temperature heterogeneity in and around a clot. In turn, the system is configured to correlate the sensed temperature from device with differences in properties of the clot, including physical and/or chemical properties, clotting mechanisms, time of clot formation, and the like. By detecting temperature heterogeneity of the clot, as well as other intravascular temperatures (e.g., at vessel wall, in regions of restricted and unrestricted flow, etc.), the system can further characterize the clot for improving diagnosis and treatment for the patient. Temperature readings by device can also be used by system to correlate and identify vulnerable plaque in and surrounding the clot to similarly characterize the clot. In some embodiments, device may also be configured to measure the pH of the clot and its surrounding areas for similar analysis of the clot.

The temperature measurement device can be in the form of a guidewire or a catheter configured to precisely measure the temperature at multiple points within a clot, along the length of the clot, at positions of the vessel wall at or adjacent the clot, proximal to the face of the clot, and distal to a clot. In some examples, the distal end of the device can be used to take these temperature measurements compared with a reference temperature at a location proximal to the clot and in a region of unrestricted blood flow. The location proximal could be at the mid-length point of the device or it could be at a point that is proximal of a bifurcation (e.g., carotid bifurcation where the clot is in one of the vessels coming off the bifurcation). It is contemplated that the temperature within the clot would be higher than the temperature in a region which has blood flow. In this respect, a difference in temperature between normal flowing blood and the blood in the region surrounding the clot can be used to characterize the clot. The device could also be used to measure the temperature of the vessel wall in the region of the clot.

The temperature measurement device could include one or more sensors embedded in a guidewire or catheter. In some examples, the device could have a single sensor at the distal tip and the temperature could be measured at different points by moving the device tip to different locations. By measuring a temperature differential between points, a relatively small region of the clot can be characterized using a minute thermocouple junction. Examples of temperature measurement devices are shown in FIGS. 24A-26A.

Figure 24A:
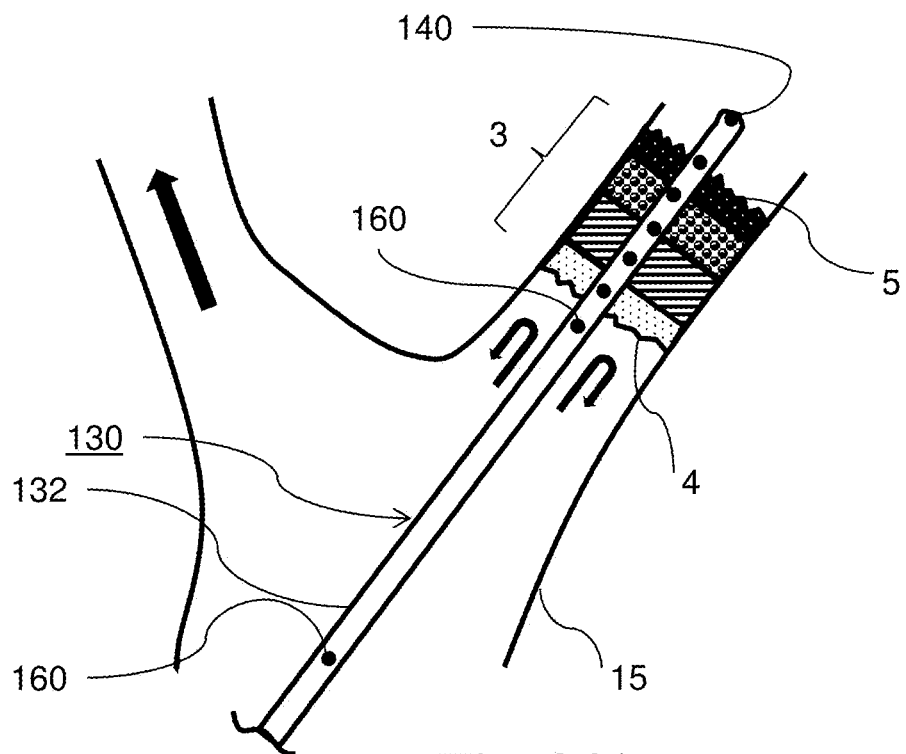
FIG. 24A depicts a device for sensing temperature of a clot and surrounding vasculature.
Figure 24B:
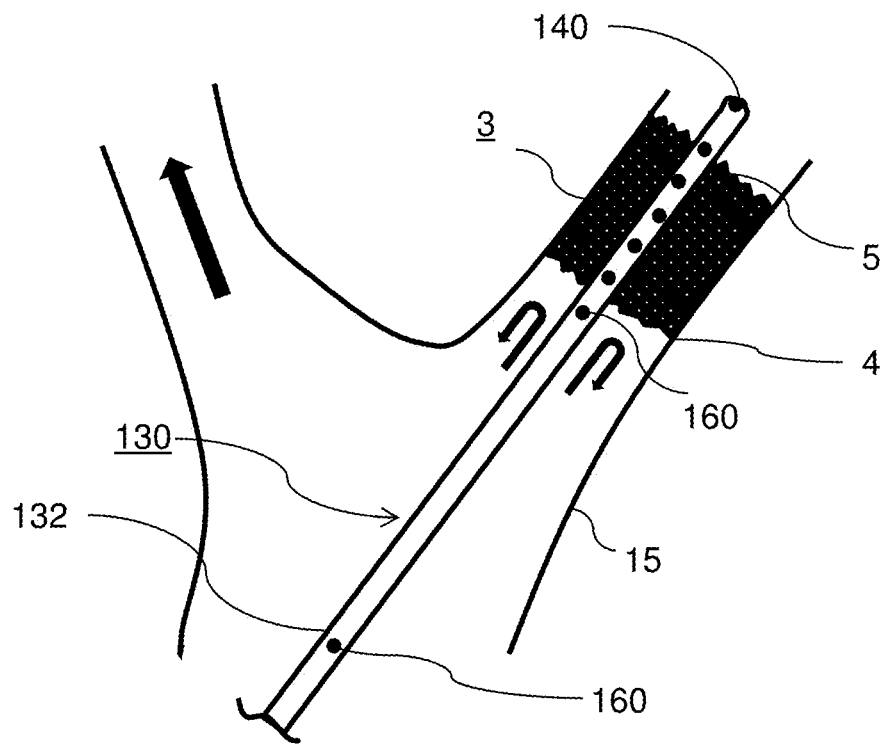
FIG. 24B depicts a device for sensing temperature of a clot and surrounding vasculature.

In particular, in FIGS. 24A-B, one example of a temperature measurement device is depicted with guidewire 130. Guidewire 130 can be a conventional guidewire with an atraumatic tip and be extended into the vasculature distally and through or about clot 3. Clot 3 in FIG. 24A is shown having an example gradient with discrete sections merely as an illustration of typical clots that vary their physical properties throughout, including from proximal face 4 and distal face 5 of clot 3. Clot 3 in FIG. 24B is shown in having uniform color, though this does not necessarily mean that clot 3 is homogenous or has any more or less of a particular property.

Guidewire 130 can be substantially elongate yet flexible to be able to be translated through the vasculature to the site of the clot. The arrows shown are intended to depict example blood flow in vessel 15. Guidewire 130 can include a single temperature sensor 160 or a plurality of sensors 160 as shown. In FIG. 24A, guidewire 130 includes one sensor 160 in the unrestricted flow region 132 of vessel 15, though more than a single sensor 160 could be used as needed or required to provide desired accuracy of the region 132. On or about the distal end 140 of guidewire 130, one or more additional sensors 160 can also be positioned. Sensors 160 can be selectively to correspond to locations of the clot 3. As shown, end 140 and corresponding sensors 160 can be translated distally until end 140 is distal of distal face 5 and to take temperature measurements both within the clot as well as proximal and distal thereof.

Figure 25A:
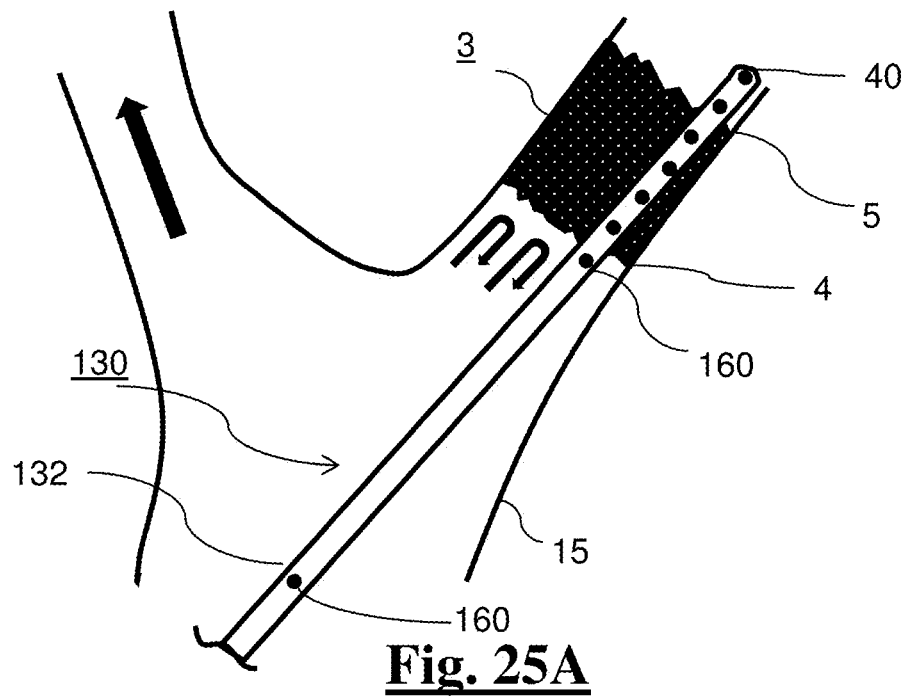
FIG. 25A depicts a device for sensing temperature of a clot and surrounding vasculature.

In FIG. 25A, distal end 140 of guidewire 130 has been translated laterally to one side of the clot so that one or more of its corresponding sensors 160 are positioned adjacent the vessel wall. In this regard, guidewire 130 can detect temperature of the vessel wall for use in further analyzing properties of clot 3 and the surrounding vasculature.

Figure 25B:
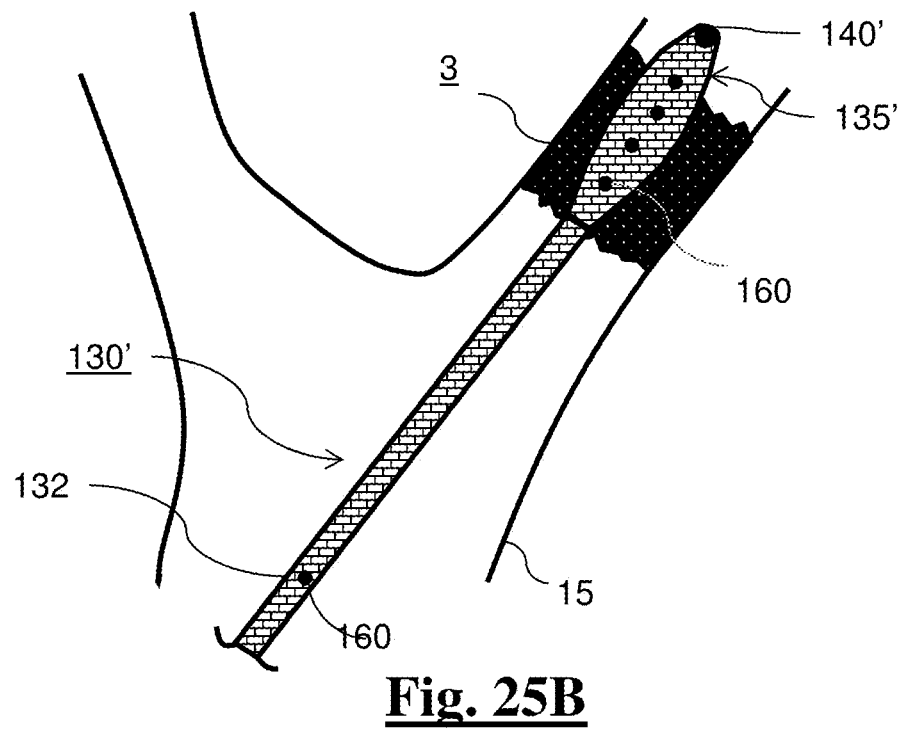
FIG. 25B depicts a device for sensing temperature of a clot and surrounding vasculature.

Turning to FIG. 25B, a modified guidewire 130' is depicted, similar to planar guidewire previously discussed in FIGS. 22A-24A. In this respect, guidewire 130' can include one or more sensors 160 positioned proximal of the clot 3 and about the distal end 140'. Distal end 140' can include a curved or expanded perimeter capable of being in an expanded configuration. Guidewire 130' can be in an expanded configuration as shown as a result of being deployed from a catheter (not depicted), from being actuated by an end user from the proximal end of guidewire 130', etc. In turn, while only six (6) sensors 160 are depicted in FIG. 25B, the distal end 140' with its expanded distal end 140' can include multiple temperature sensors 160 so more simultaneous temperature measurements can be taken throughout the clot 3 for more precise clot characterization.

Figure 26A:
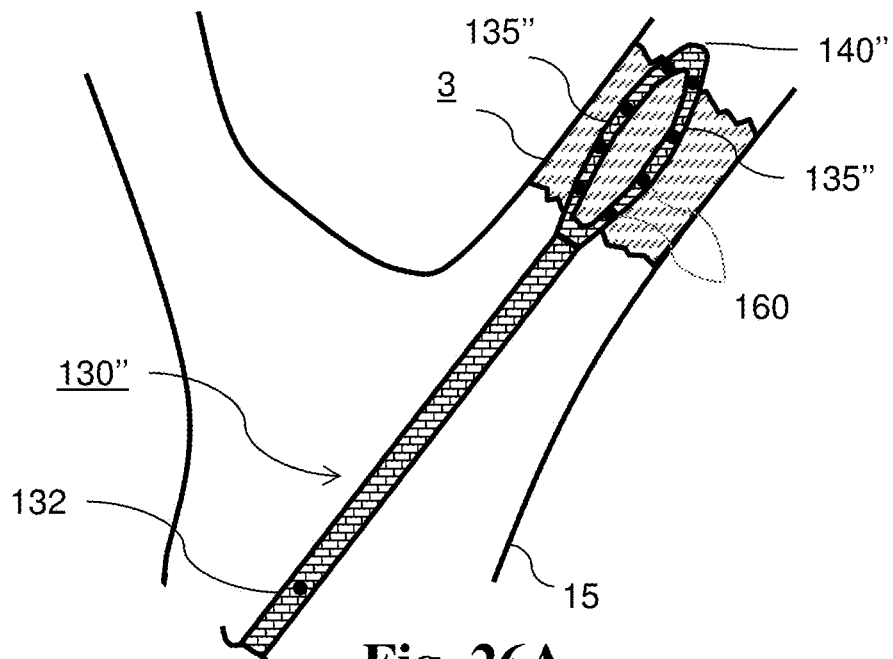
FIG. 26A depicts a device for sensing temperature of a clot and surrounding vasculature.

Turning to FIG. 26A, another modified guidewire 130" is depicted, similar to guidewire 130'. In this respect, guidewire 130" can include one or more sensors 160 positioned proximal of the clot 3 and about the distal end 140". Distal end 140" in this embodiment can include multiple loops 135" that define a curved or expanded perimeter with a gap or space formed between the respective loops 135" in the expanded configuration. Each loop 135" of distal end 140" can include multiple temperature sensors 160 so more simultaneous temperature measurements can be taken throughout the clot 3 for more precise clot characterization, including at multiple locations within the clot 3.

Figure 26B:
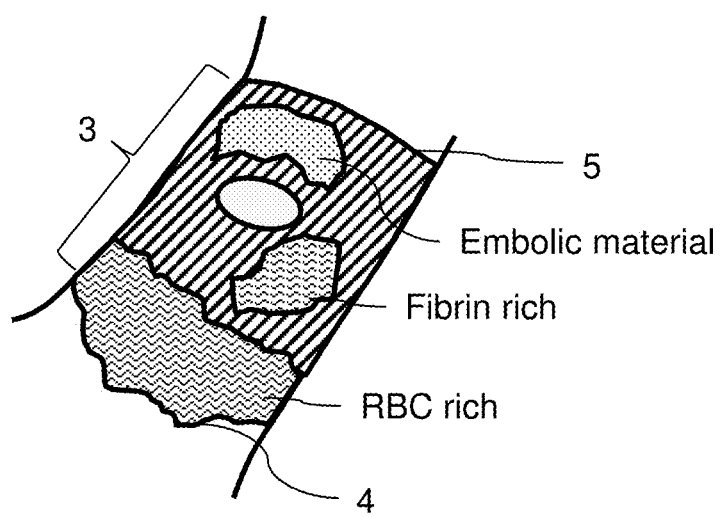
FIG. 26B is a close-up view of one example of a clot for analysis using solutions of this disclosure.

FIG. 26B is a close-up view of one example of a clot 3 as it could be analyzed by guidewire 130/130'. For example, in clot 3 of FIG. 26B it can be seen how heterogenous clot 3 can be in terms of its material composition. In the depicted example, clot 3 includes multiple regions with differing properties, such as a proximal RBC rich region, a central fibrin rich region, and distally located embolic material within the clot 3. The solutions of this disclosure are particularly advantageous since they can be used to detect in vivo the different material properties of clot 3, including any regions internal therein, to then analyze and determine the optimal treatment device(s) and corresponding treatment protocol for the patient.

Figure 27:
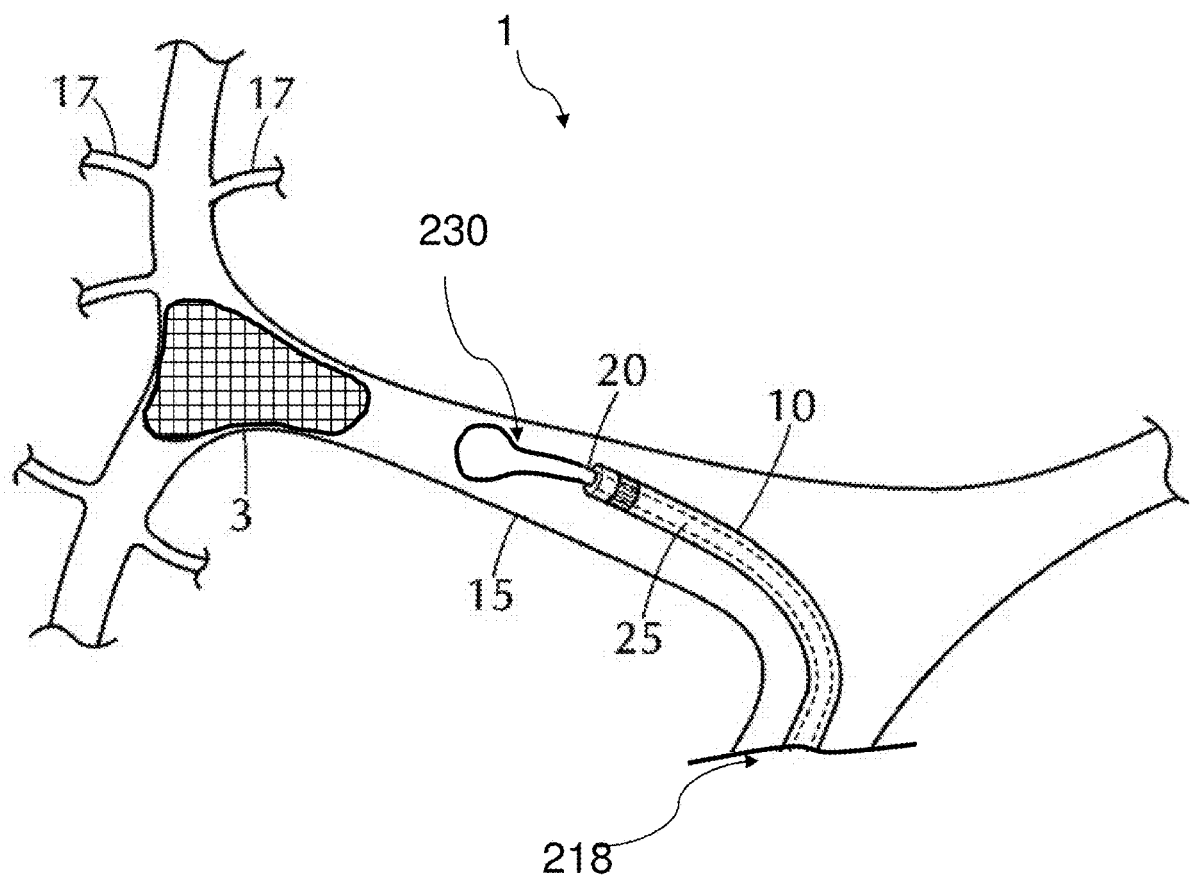
FIG. 27 is a conventional mechanical thrombectomy system including a guidewire of this disclosure before crossing through a clot, occlusion or blockage.

FIG. 27 depicts a similar thrombectomy system as in FIG. 18 except for a different guidewire 230 of this disclosure. In particular, guidewire 230 of this disclosure resolves problems with guidewire 29 and other problems in the art with its flattened, planar distal end 240 designed to be oriented in only two configurations and be prevented from advancing into vessels 17, as is the case with guidewire 29 of FIG. 18.

Figure 28:
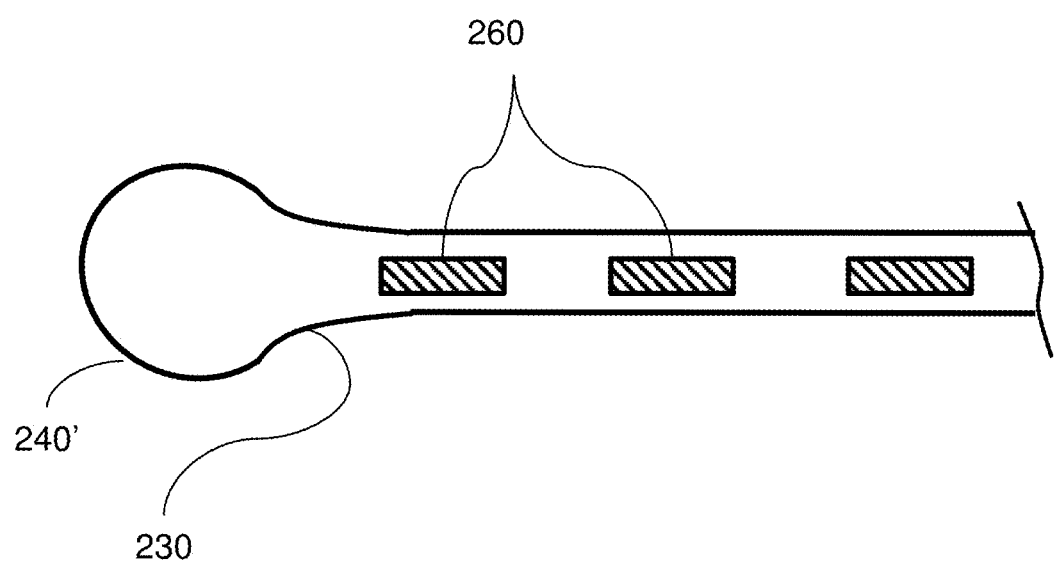
FIG. 28 is an exemplary illustration of an atraumatic clot-circumventing configured distal tip of a guidewire.

FIG. 28 is an exemplary illustration of an atraumatic clot-circumventing configured distal tip 240 of a guidewire 230. Tip 240 can be a flattened portion of the core wire cut or stamped into a paddle shape, as described more particularly in U.S. patent application Ser. No. 16/003,527, now U.S. Pat. No. 10,667,833 issued Jun. 2, 2020, which is incorporated by reference herein in its entirety as if set forth verbatim. As can be seen, the paddle shaped distal tip 240 is in a relaxed or non-compressed state (not subject to application of an external mechanical force). Rather than pre-forming or pre-shaping the guidewire 230 to a desired geometric shape, the distal tip 240 can have a circular lateral cross-section and/or may alternatively be flattened out and then cut or stamped into a desired geometric shape to form the atraumatic clot-circumventing configured distal end or tip (e.g., as the depicted "planar paddle shape" 240).

Because prior guidewires were round, there was no easy way to control the orientation of the guidewire 230 as to the clot 3 and any sensors 260. To resolve this problem, planar guidewire 230' is basically configured to be oriented only in the depicted flat or planar position of FIG. 28 or a collapsed condition prior to deployment. This is particularly advantageous with guidewire 225' since sensors 260 would be caused to face the clot 260 during use, rather than rotating or moving or otherwise moving in a manner that causes sensors 260 to misread or inaccurately sense properties of clot 3. For example, since sensors of rounded guidewires could potentially move between vessel wall and the clot itself creating confusion as to what properties are being sensed, rather than developing a complex algorithm to sort out and process the resultant signals, which may not be easy to do and which result in reduced sensing accuracy, the herein disclosed planar guidewire 230, including planar tip 240, can be operable to move between one of two orientations. Sensors 260 can be advantageously positioned on both sides of the guidewire 230 and/or aligned with tip 240. In turn, the resultant clot sensing signals detected through sensors 260 will be much easier to distinguish and process since they will be oriented as either fully facing the clot 3 or fully facing the vessel wall 15.

The guidewire 230 may be retracted or drawn back through the distal end 20 of the microcatheter 10. In this respect, the distal tip 240 of guidewire 230 can move between collapsed to expanded configuration in a manner akin to that of rolling one's tongue (e.g., in the collapsed configuration, lateral edges of distal end 240 can be in a curled or curved or wrapped state and then can curl or roll towards one another during deployment to the expanded, paddle configuration). Upon exiting from the lumen 25 of the microcatheter 10, the paddle shaped distal end or tip 240 of the guidewire is automatically restored to its former planar relaxed or non-compressed state (not subject to application of an external mechanical force) (as seen in FIG. 28).

Figure 29:
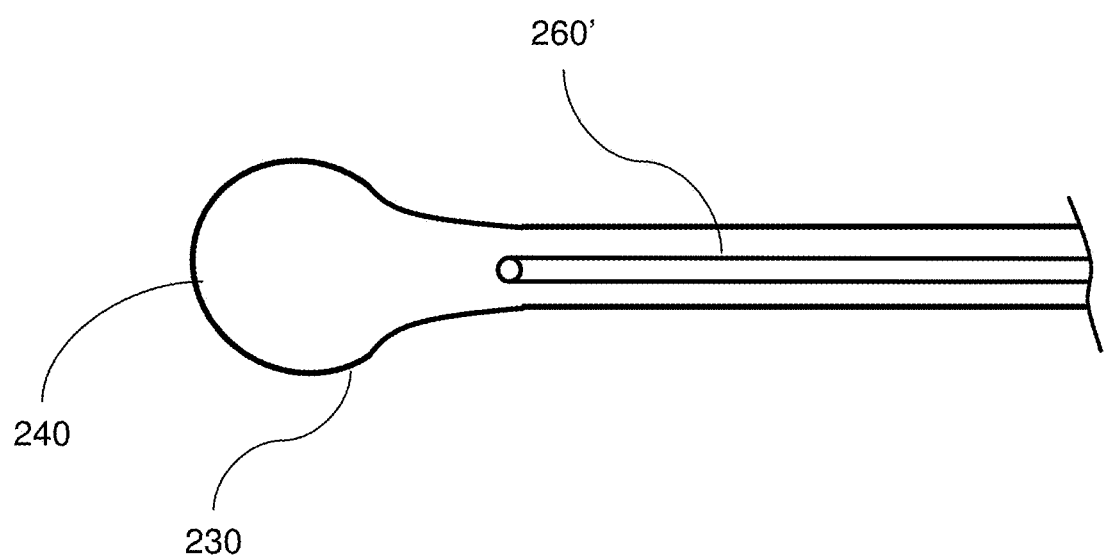
FIG. 29 is an exemplary illustration of an atraumatic clot-circumventing configured distal tip of a guidewire.

FIG. 29 is an exemplary illustration of an atraumatic clot-circumventing configured distal tip 240 of a guidewire 230, similar to tip 240 of guidewire 230 except for that the guidewire 230 of FIG. 29 includes fiber sensor 260' that can be aligned with the planar, flattened surface of guidewire 230.

Figure 30A:
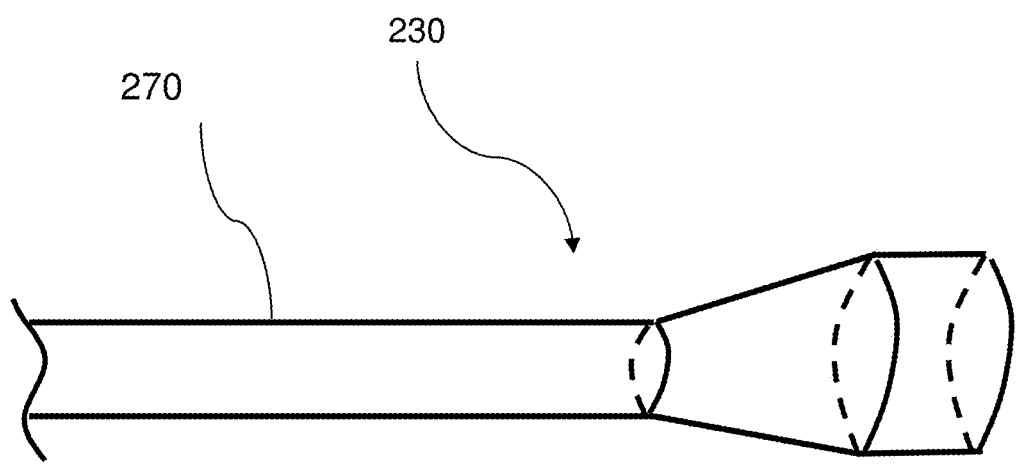
FIG. 30A illustrates an example step of one aspect of a method or use of manufacturing a guidewire of this disclosure.

Turning to FIG. 30A, an example step of one aspect of a method or use of manufacturing a guidewire 230 is shown. In the depicted step, only the distal end of a shaft 270 for a guidewire 230 of memory material (e.g., shape memory alloy such as nitinol) is shown. The shaft 270 can have any diameter, for example, by being shaped from a 0.013" core wire to be grinded to the depicted shape in FIG. 30A.

Figure 30B:
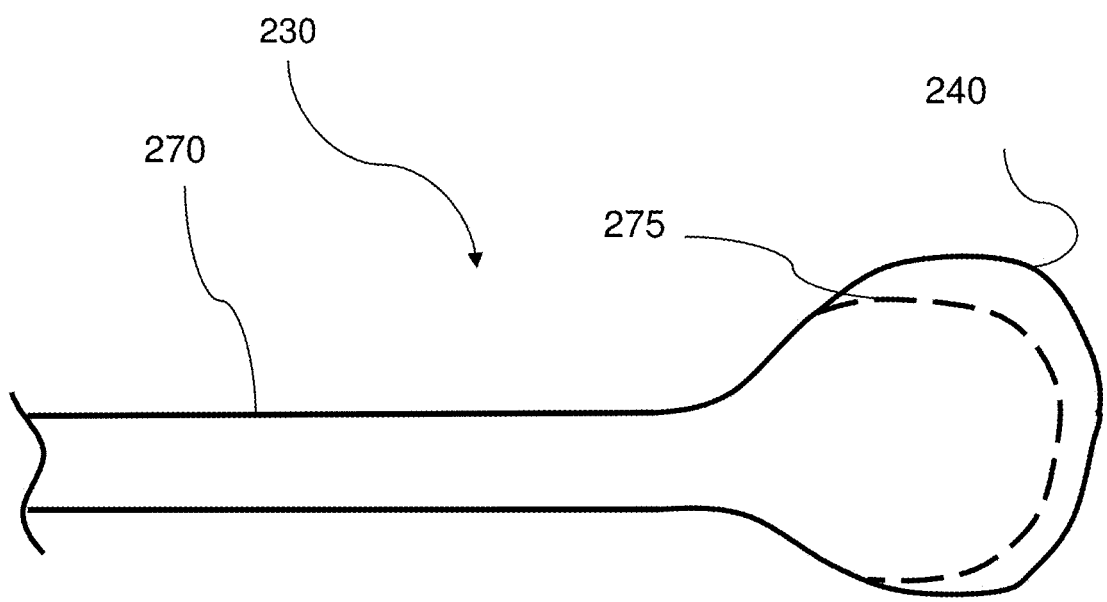
FIG. 30B illustrates an example step of one aspect of a method or use of manufacturing a guidewire of this disclosure.

Moving to FIG. 30B in a subsequent step, it can be seen that the distal end of shaft 270 has been flattened or pressed to the previously discussed planar shape of tip 240. The shape of tip 240 being flattened or otherwise looped is particularly advantageous also since is also capable of preventing the guidewire 230 from entering and damaging small perforator vessels 17 branching from the main artery. FIG. 30B also shows a cut line 275 that can be used for cutting pressed or flattened shaft 270. The step of cutting in some aspects can be done by laser, water jet, or wire electrical discharge machining (EDM), pressing, or the like for cutting the shaft to the depicted shape. After being cut, a polymer jacket can be added with, for example, radiopaque material such as filler (e.g., made of platinum alloy or other radiopaque material). Stated differently, tip 240 can be made by grinding, flattening and then cutting. The resultant flattened shape of tip 240 can then then be jacketed with a polymer outer cover.

Turning to FIG. 31A, an example guidewire 230 is depicted in a perspective view with a proximal end 238 and the previously discussed distal end 240 with flattened or planar tip. Distal tip 240 can be flattened to form a thin support structure or substrate 250, typically having a thickness ranging from approximately 0.0005" to approximately 0.010", preferably the thickness ranges from approximately 0.001" to approximately 0.006".

Tip 240 may alternatively be achieved by assembling a pre-formed planar paddle shaped distal end or tip, having the same specified thickness range, on an end of a separate core wire, such as by welding, soldering or bonding. Two separate components assembled or joined together is particularly well suited to applications in which the pre-formed planar paddle and core wire on which the paddle is to be assembled are made of different materials.

As illustrated in the cross-sectional view in FIG. 31B taken along section A-A of FIG. 31A, an outer covering or layer 255 may be applied to the external surface of the supporting structure 250. Outer covering or layer 255 may comprise one or more coverings, coating layers, or films. For instance, the outer covering or layer 255 may comprise a polymer jacket applied directly to the outer surface of the support structure or substrate 250 with or without a lubricious coating, e.g., a hydrophilic material, applied directly to the outer surface of the polymer jacket. The outer jacket may also contain radiopaque fillers to enhance fluoroscopic visibility of the tip. An example width of structure or substrate 255 can be 0.024" and a corresponding width of layer 55 can be 0.028" (e.g., a thickness of 0.002" for layer 255). However, layer 255 could be thicker and each of structure or substrate 250 and layer 255 could be greater or smaller.

As illustrated in the cross-sectional view in FIG. 31C taken along section B-B of FIG. 31A, the portion proximal of distal end 240 of guidewire 230 can have a diameter or thickness that is greater than flattened or pressed distal end 240. For example, a proximal portion of guidewire 230 can be 0.006" while a distal portion of guidewire 230 adjacent or at distal end 240 could be 0.002". In this respect, guidewire 230 can taper going from its proximal 238 to distal end 240. Guidewire 230 can taper more or less gradually as needed or required to form corresponding flattened or pressed distal end 240.

Figure 32:
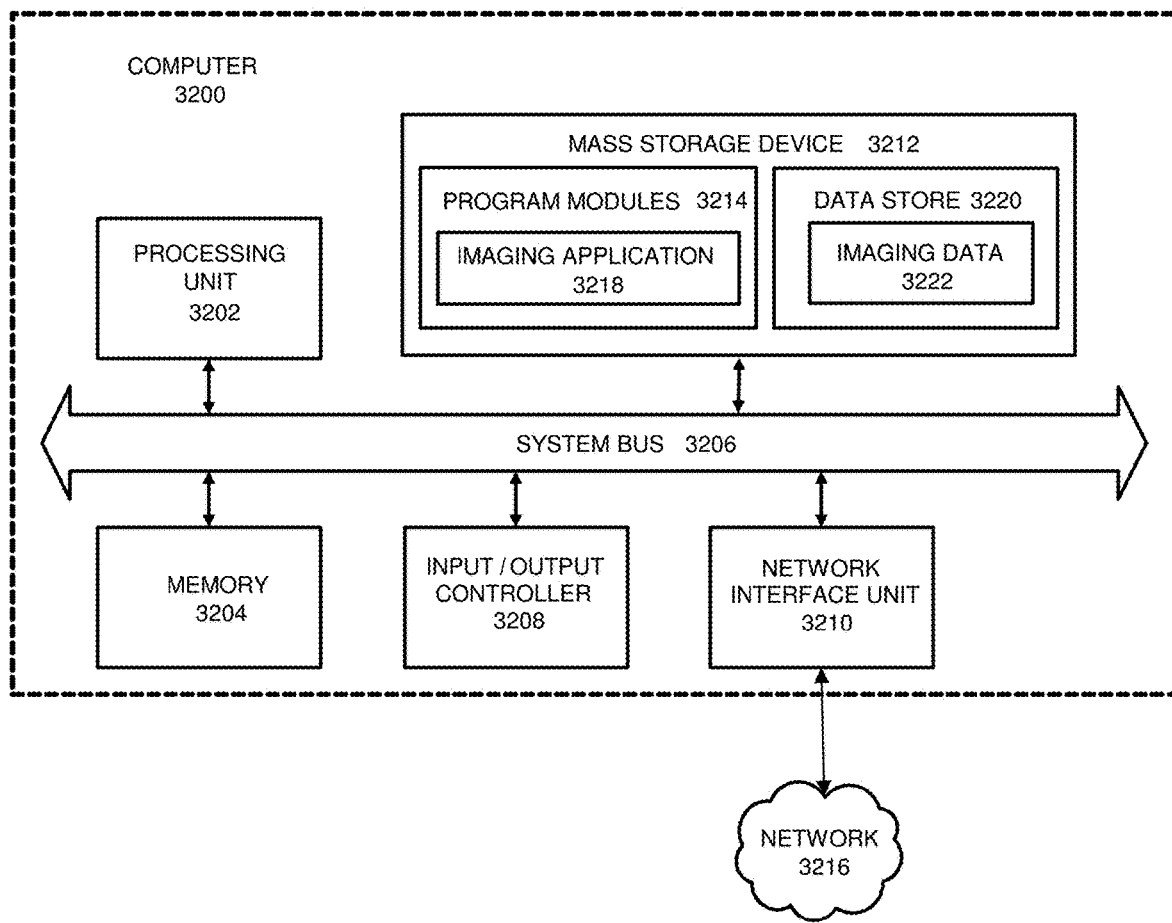
FIG. 32 is a computer architecture diagram showing a general computing system capable of implementing aspects of the present disclosure in accordance with one or more embodiments described herein.

FIG. 32 is a computer architecture diagram showing a general computing system capable of implementing aspects of the present disclosure in accordance with one or more embodiments described herein, including clot analysis and/or clot classification and/or individualizing a treatment protocol for a patient. A computer 3200 may be configured to perform one or more functions associated with embodiments of this disclosure. For example, the computer 3200 may be configured to perform operations in order to render the imaging of associated with the herein disclosed embodiments related to clot analysis and/or classification and/or individualizing treatment protocol for a respective patient. It should be appreciated that the computer 3200 may be implemented within a single computing device or a computing system formed with multiple connected computing devices. The computer 3200 may be configured to perform various distributed computing tasks, in which processing and/or storage resources may be distributed among the multiple devices. The data acquisition and display computer 3250 and/or operator console 3210 of the system shown in FIG. 32 may include one or more systems and components of the computer 3200.

As shown, the computer 3200 includes a processing unit 3202 ("CPU"), a system memory 3204, and a system bus 3206 that couples the memory 3204 to the CPU 3202. The computer 3200 further includes a mass storage device 1812 for storing program modules 1814. The program modules 3214 may be operable to analyze and/or classify one or more clots in vivo and/or in vitro, as well as individualize treatment of a patient, discussed herein. For example, to cause the computer 3200 to a clot of a patient as described in any of the figures of this disclosure. The program modules 3214 may include an imaging application 3218 for performing data acquisition and/or processing functions as described herein, for example to acquire and/or process image data corresponding to magnetic resonance imaging of an area of interest. The computer 3200 can include a data store 3220 for storing data that may include imaging-related data 3222 such as acquired data from the implementation of magnetic resonance imaging in accordance with various embodiments of the present disclosure.

The mass storage device 3212 is connected to the CPU 3202 through a mass storage controller (not shown) connected to the bus 3206. The mass storage device 3212 and its associated computer-storage media provide non-volatile storage for the computer 3200. Although the description of computer-storage media contained herein refers to a mass storage device, such as a hard disk or CD-ROM drive, it should be appreciated by those skilled in the art that computer-storage media can be any available computer storage media that can be accessed by the computer 3200.

By way of example and not limitation, computer storage media (also referred to herein as "computer-readable storage medium" or "computer-readable storage media") may include volatile and non-volatile, removable and non-removable media implemented in any method or use or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 1800. "Computer storage media", "computer-readable storage medium" or "computer-readable storage media" as described herein do not include transitory signals.

According to various embodiments, the computer 3200 may operate in a networked environment using connections to other local or remote computers through a network 1816 via a network interface unit 3210 connected to the bus 3206. The network interface unit 1810 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 3200 may also include an input/output controller 3208 for receiving and processing input from any of a number of input devices. Input device as may include one or more of keyboards, mice, stylus, touchscreens, microphones, audio capturing devices, and image/video capturing devices. An end user may utilize the input devices to interact with a user interface, for example a graphical user interface, for managing various functions performed by the computer 3200. The bus 3206 may enable the processing unit 3202 to read code and/or data to/from the mass storage device 3212 or other computer-storage media.

The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state or may include rotating media storing magnetically-encoded information. The program modules 3214, which include the imaging application 3218, may include instructions that, when loaded into the processing unit 3202 and executed, cause the computer 3200 to provide functions associated with one or more embodiments illustrated in the figures of this disclosure. The program modules 3214 may also provide various tools or techniques by which the computer 3200 may participate within the overall systems or operating environments using the components, flows, and data structures discussed throughout this description.

In general, the program modules 3214 may, when loaded into the processing unit 3202 and executed, transform the processing unit 3202 and the overall computer 3200 from a general-purpose computing system into a special-purpose computing system. The processing unit 3202 may be constructed from any number of transistors or other discrete circuit elements, which may individually or collectively assume any number of states. More specifically, the processing unit 3202 may operate as a finite-state machine, in response to executable instructions contained within the program modules 3214. These computer-executable instructions may transform the processing unit 3202 by specifying how the processing unit 3202 transitions between states, thereby transforming the transistors or other discrete hardware elements constituting the processing unit 3202.

Encoding the program modules 3214 may also transform the physical structure of the computer-storage media. The specific transformation of physical structure may depend on various factors, in different implementations of this description. Examples of such factors may include but are not limited to the technology used to implement the computer-storage media, whether the computer storage media are characterized as primary or secondary storage, and the like. For example, if the computer storage media are implemented as semiconductor-based memory, the program modules 3214 may transform the physical state of the semiconductor memory, when the software is encoded therein. For example, the program modules 3214 may transform the state of transistors, capacitors, or other discrete circuit elements constituting the semiconductor memory.

As another example, the computer storage media may be implemented using magnetic or optical technology. In such implementations, the program modules 3214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Figure 33:
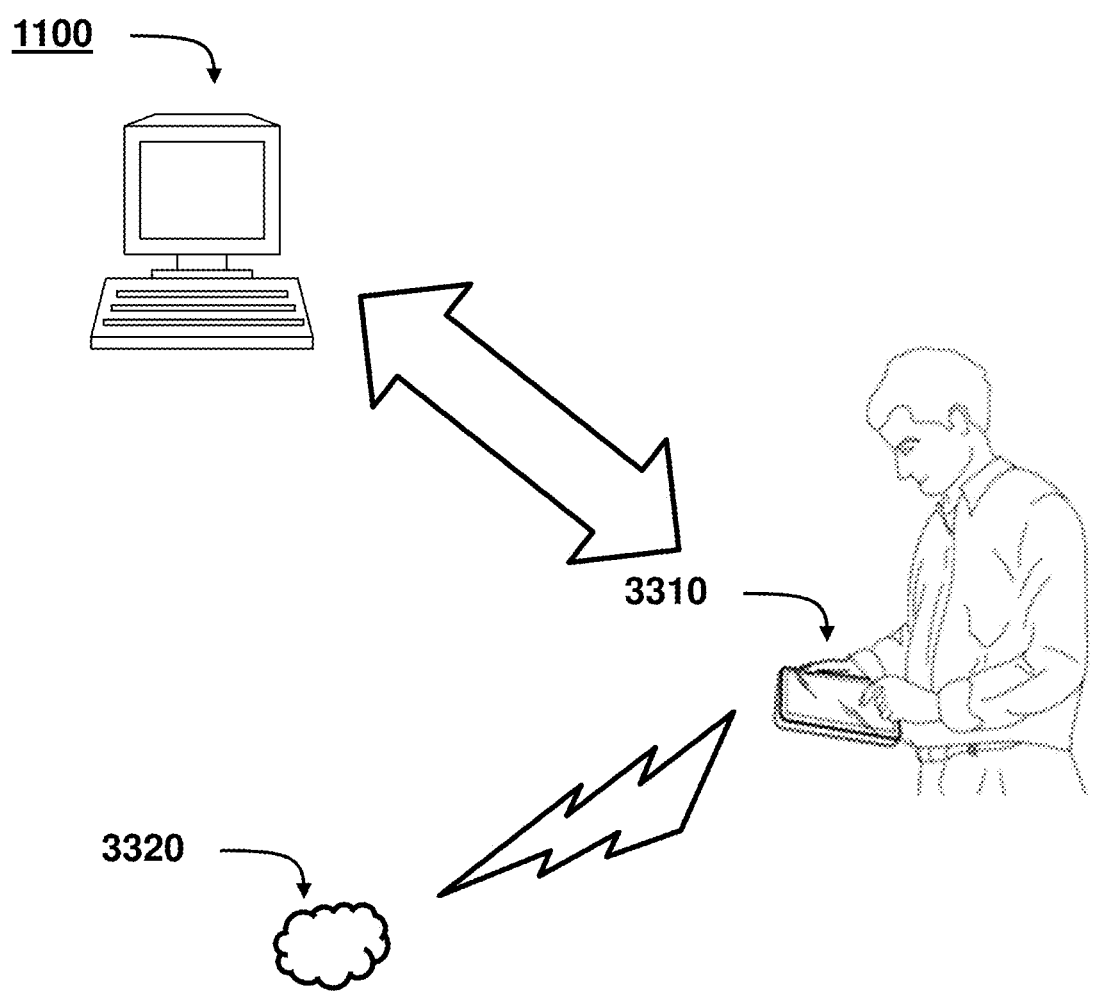
FIG. 33 depicts a schematic overview of a mobile device analyzing a clot or fragments of a clot in vitro recently removed from the patient.

FIG. 33 depicts a schematic overview of an example embodiment of a mobile device 3310 analyzing a clot 3320 or fragments of a clot 3320 in vitro recently removed from the patient. The mobile device 3310 may be any electronic device configured to capture images, such as a mobile phone, media player, portable gaming device, tablet computer, or the like. It is noted that the present disclosure is not limited to any single type of mobile device. Device 3310 can be wirelessly connected and controlled by an external computing device and/or system, such as system 3200, whereby such external system can be operable to execute instructions related to analysis and/or classification and/or individualization of a treatment protocol for the clot, according to any of the previously disclosed embodiments of this disclosure. Alternatively, device 3310 can carry out the analysis and/or classification and/or individualization of a treatment protocol for a patient and their respective clot, locally.

Device 3310 may operatively communicate with the external computing device through an application resident on device 3310. Device 3310 may include an optical system, such as an onboard camera, configured to capture images or video of clot 3320 or fragments of a clot 3320 in order to analyze and/or classify the same.

Exemplary architecture of device 3310 can include a central processing unit, where computer instructions are processed; a display interface that acts as a communication interface and provides functions for rendering video, graphics, images, and texts on the display and a keyboard interface that provides a communication interface to a keyboard; and a pointing device interface that provides a communication interface to device 3310 and/or any external computing devices coupled thereto. Example embodiments of the architecture may include an antenna interface that provides a communication interface to an antenna. Example embodiments may include a network connection interface that may provide a communication interface to an external device or network.

In certain embodiments, a camera interface may be provided that acts as a communication interface and provides functions for capturing digital images from the onboard camera and capabilities of visualizing certain aspects of the clot, including levels of fibrin, red blood cells, white blot cells, serum, and other physical properties. According to example embodiments, a random access memory (RAM) may be provided, where computer instructions and data may be stored in a volatile memory device for processing by the CPU. The architecture may include a read-only memory (ROM) where invariant low-level system code or data for basic system functions such as basic input and output (I/O), startup, or reception of keystrokes from a keyboard are stored in a non-volatile memory device. According to an example embodiment, the architecture may include a storage medium or other suitable type of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system, application programs (including, for example, a web browser application, a widget or gadget engine, and or other applications, as necessary) and data files are stored. According to an example embodiment, the architecture may include a power source that provides an appropriate alternating current (AC) or direct current (DC) to power components. According to an example embodiment, the architecture may include a telephony subsystem that allows the device to transmit and receive sound over a telephone network. The constituent devices and the CPU may communicate with each other over a bus.

Various aspects of the disclosed solution may be still more fully understood from the following description of some example implementations and corresponding results. Some experimental data is presented herein for purposes of illustration and should not be construed as limiting the scope of the disclosed technology in any way or excluding any alternative or additional embodiments.

Figure 34:
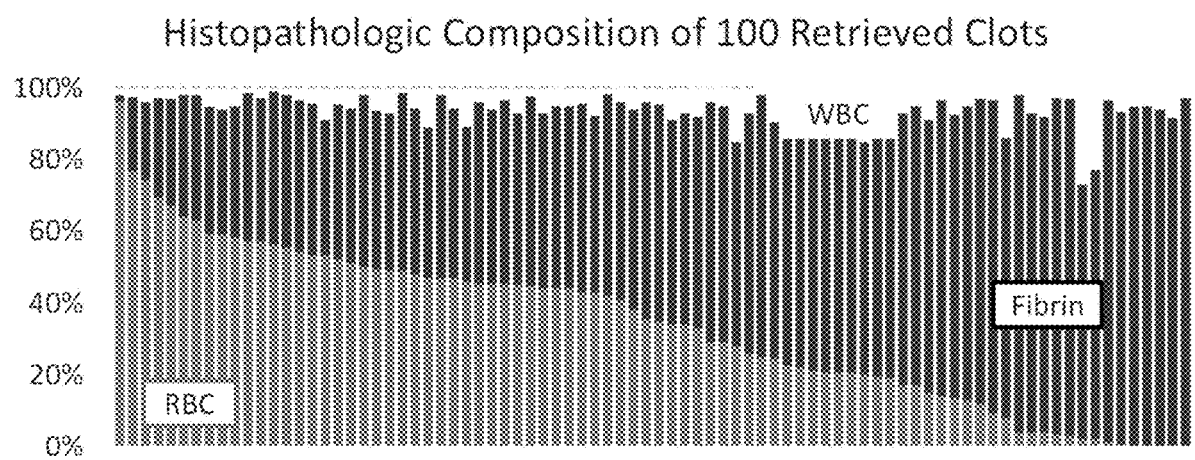
FIG. 34 depicts an overview of histopathologic composition of clots analyzed in this disclosure.

FIG. 34 depicts an overview of histopathologic composition of 100 clots analyzed in this disclosure. The clot analysis for each clot has been sorted from highest to lowest red blood cell (RBC) count and lowest to highest fibrin count. FIG. 34 shows significant variance of even just three clot physical properties across 100 clots tested in vitro that requires different treatment protocols depending on such identified physical properties.

Figure 35A:
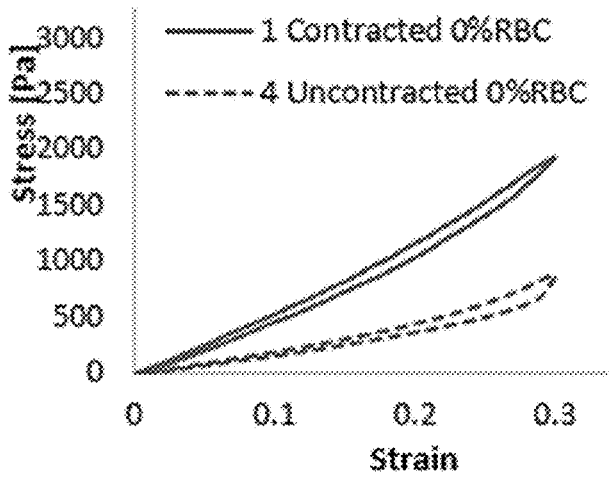
FIG. 35A depicts a graph showing the stress-strain curve of a clot in contracted and uncontracted states identified as having 0% red blood cell count.
Figure 35B:
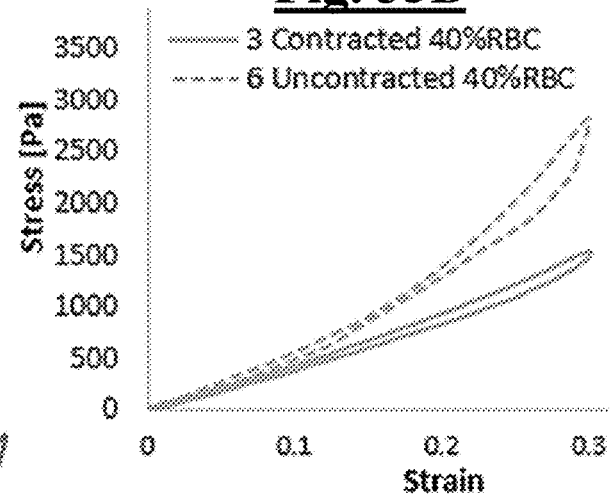
FIG. 35B depicts a graph showing the stress-strain curve of for a clot in contracted and uncontracted states identified as having 40% red blood cell count.
Figure 35C:
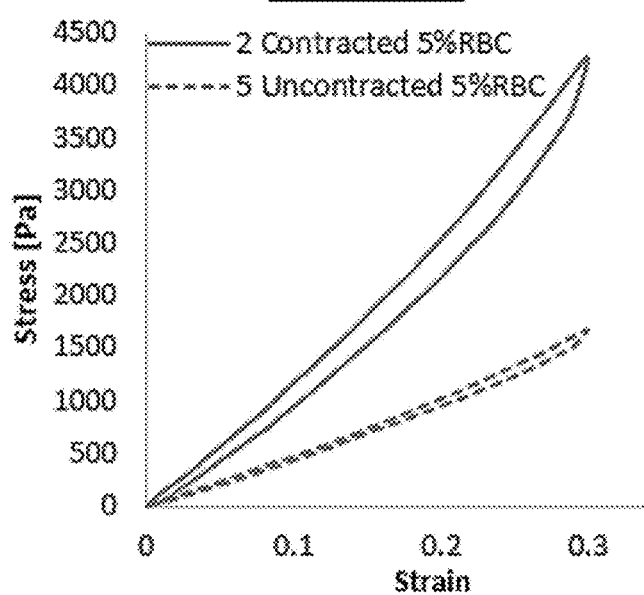
FIG. 35C depicts a graph showing the stress-strain curve of for a clot in contracted and uncontracted states identified as having 5% red blood cell count.

FIGS. 35A-C depict graphs that compare the strain rate for three separate clots classified by red blood cell count. Specifically, FIG. 35A depicts a graph showing the strain rate for a clot in contracted and uncontracted states identified as having 0% red blood cell count, FIG. 35B depicts a graph showing the strain rate for a clot in contracted and uncontracted states identified as having 40% red blood cell count, and FIG. FIG. 35C depicts a graph showing the strain rate for a clot in contracted and uncontracted states identified as having 5% red blood cell count. As can be seen, as red blood cell count varies in the clots that were analyzed, platelet activated contraction of the clot changes its corresponding stiffness and in turn the treatment necessary to restore perfusion to a vessel occluded by said clot. The solution of this disclosure is configured to treat patients across the depicted red blood cell accounts, classify, analyze, and determine the treatment protocol for the individual with the occluded vessel.

The first study of this disclosure also examined the composition of clot fragments retrieved with each pass of a device during the thrombectomy procedure and FIG. 36 is a table that shows clinical characteristics of the patients in the first study from whom clot fragments were retrieved by endovascular therapy for histopathological analysis. The first study sought to clarify the association between clot composition and pass number and how this may inform device selection, refine the procedural technique and to help develop technologies to successfully retrieve difficult clots. Numerous studies to date have examined the histopathology of clots retrieved from AIS patients, with clots retrieved in separate passes analyzed as an entirety and yet few, if any, studies have examined the composition of clots retrieved in individual passes. The aim of the first study was to evaluate clot composition over multiple passes and correlate this with procedural and patient factors (e.g., angiographic revascularisation outcome and/or stroke aetiology). As previously discussed, AIS patients with vessels occluded with RBC-rich clots versus fibrin-rich and/or platelet rich clots have differing recanalization outcomes, since RBC-rich clots generally have increased viscosity and deformability along with reduced elasticity and stiffness. Prior to this study, in animal models it was understood that vessels occluded with RBC-rich clots could achieve nearly 100% recanalization, in comparison to a significantly lower percentage (37.5%) of recanalization achieved in vessels occluded with the fibrin-rich clots.

With this understanding, the mechanical thrombectomy procedure of the first study involved multiple attempts or passes to retrieve the occluding clot and subsequently increase the chances of improved patient outcome. The mechanical thrombectomy was performed by a team of experienced neuroradiologists in accordance with local guidelines. In most cases the occlusion was reached using a guide catheter inserted via the femoral artery. After each pass, the device, intermediate catheter if withdrawn, and aspiration syringe were inspected for the presence of clot fragments. During the procedure fragments retrieved in each pass were isolated in individual sample containers. The clots were examined histopatholigically using a Martius Scarlett Blue stain, which allows the differentiation of red blood cells, fibrin and white blood cells. Quantitative analysis of the relative area occupied by each component was carried out for each clot.

Conventional studies analyzing human AIS clots have not reported on the "per-pass" composition of retrieved clots. For example, Marder et al (2006) performed a histologic analysis on 25 AIS clots and showed that 75% of retrieved clots were fibrin rich, and RBC dominant clots composed uniquely of RBCs were uncommon. Marder, supra, p. 2086-93. The results of the first study showed that fibrin rich clots required a greater number of recanalization attempts in comparison to RBC-rich clots (2.8 passes versus 4.5 passes respectively). In this current study, there was significant variation in the overall clot composition when comparing clot fragments removed in the first two passes when compared to 3 or more passes. See, e.g., FIG. 40A. Overall, the differentiation achieved through the analysis of clot composition per-pass provided a superior insight into the progression of the thrombectomy procedure in comparison to the combined "per-case" clot composition. Further, the "per-pass" clot composition was compared in said first study that included data from sixty (60) cases related to patients with procedural and clinical data including angiographic outcome and stroke aetiology.

Trial of Org 10172 in Acute Stroke Treatment (TOAST) classification system was applied to define suspected aetiology of AIS based on diagnostic and clinical information available for each patient which included: (1) Atheroembolic (2) Cardioembolic, (3) other determined aetiology, (4) undetermined or cryptogenic aetiology.

Figure 37A:
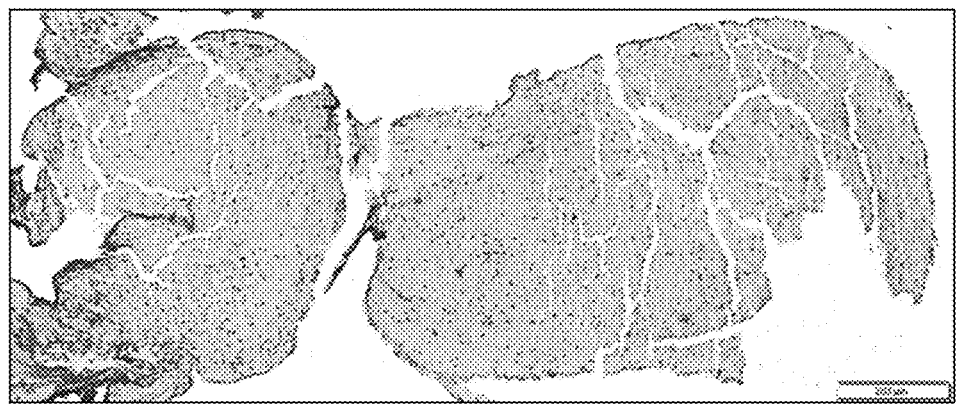
FIGS. 37A through 37D depict the distribution of fibrin and RBCs from the first study.
Figure 37B:
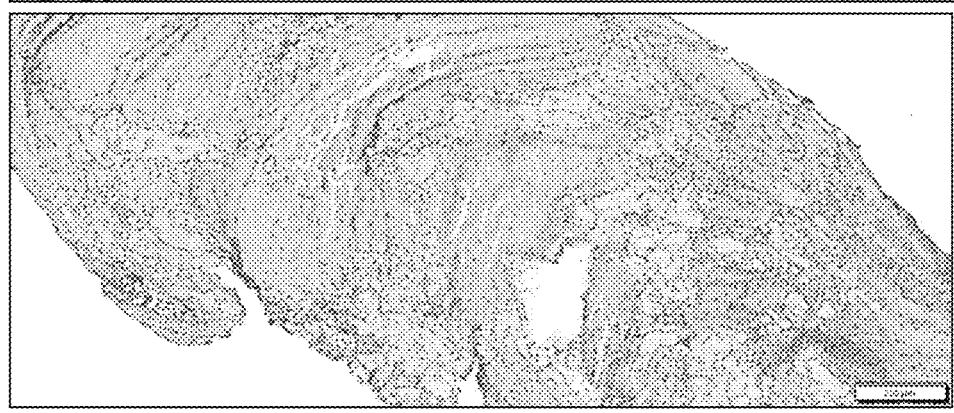
Figure 37C:
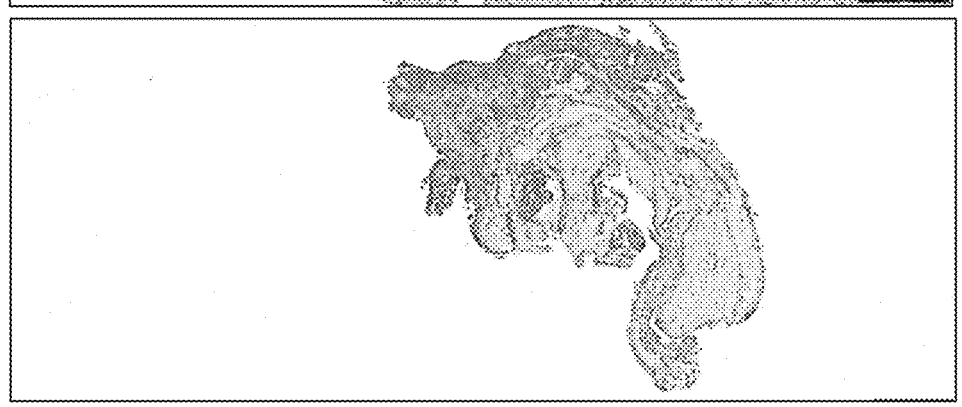
Figure 37D:

Regarding histopathology findings, Clot Material from the 106 out of a total of 138 passes were processed histologically and stained with H&E and MSB. Staining revealed high inter-pass variation, and intra-pass variation in the distribution of fibrin and RBCs as illustrated in FIGS. 37A-D. More specifically, FIGS. 37A-37D show the results of MSB staining of clots retrieved by thrombectomy in the first study. Red blood cells stained yellow are depicted in the lighter, more white portion of the depicted clot (i.e. the lighter grey) whereas fibrin stained red is depicted in the darker grey, and the nuclei of the white blood cells was stained purple and depicted in black in the close-up in FIG. 37D. FIG. 37A generally depicts a clot that is RBC rich, FIG. 37B depicts a heterogeneous clot with a mixture of RBCs and fibrin, FIG. 37C depicts a clot with areas of large fibrin and RBC domains, and FIG. 37D depicts a fibrin-rich clot. The captured image in the upper right-hand corner of FIG. 37D illustrates the aforementioned stained purple nuclei of the white blood cells.

Figure 38:
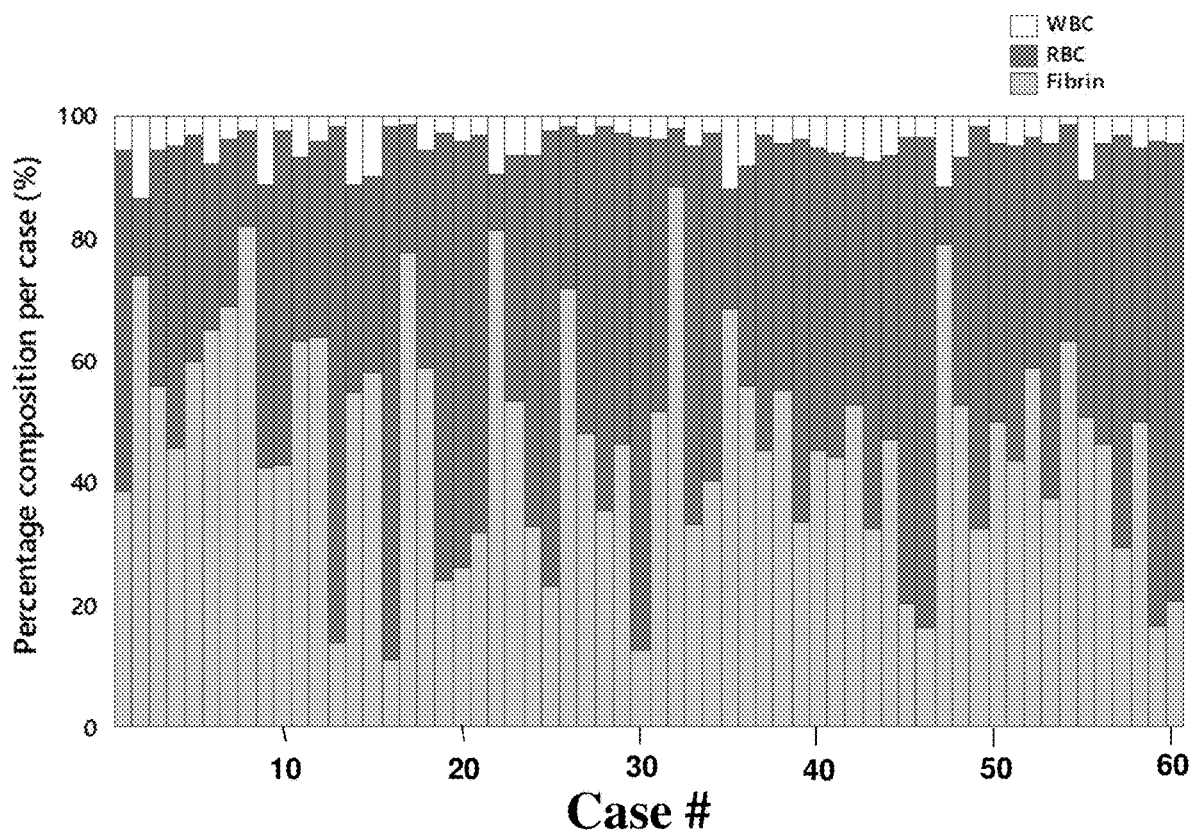
FIG. 38 depicts RBC, fibrin and WBC composition of clot fragments combined from each pass for every case in the first study.
Figure 39:
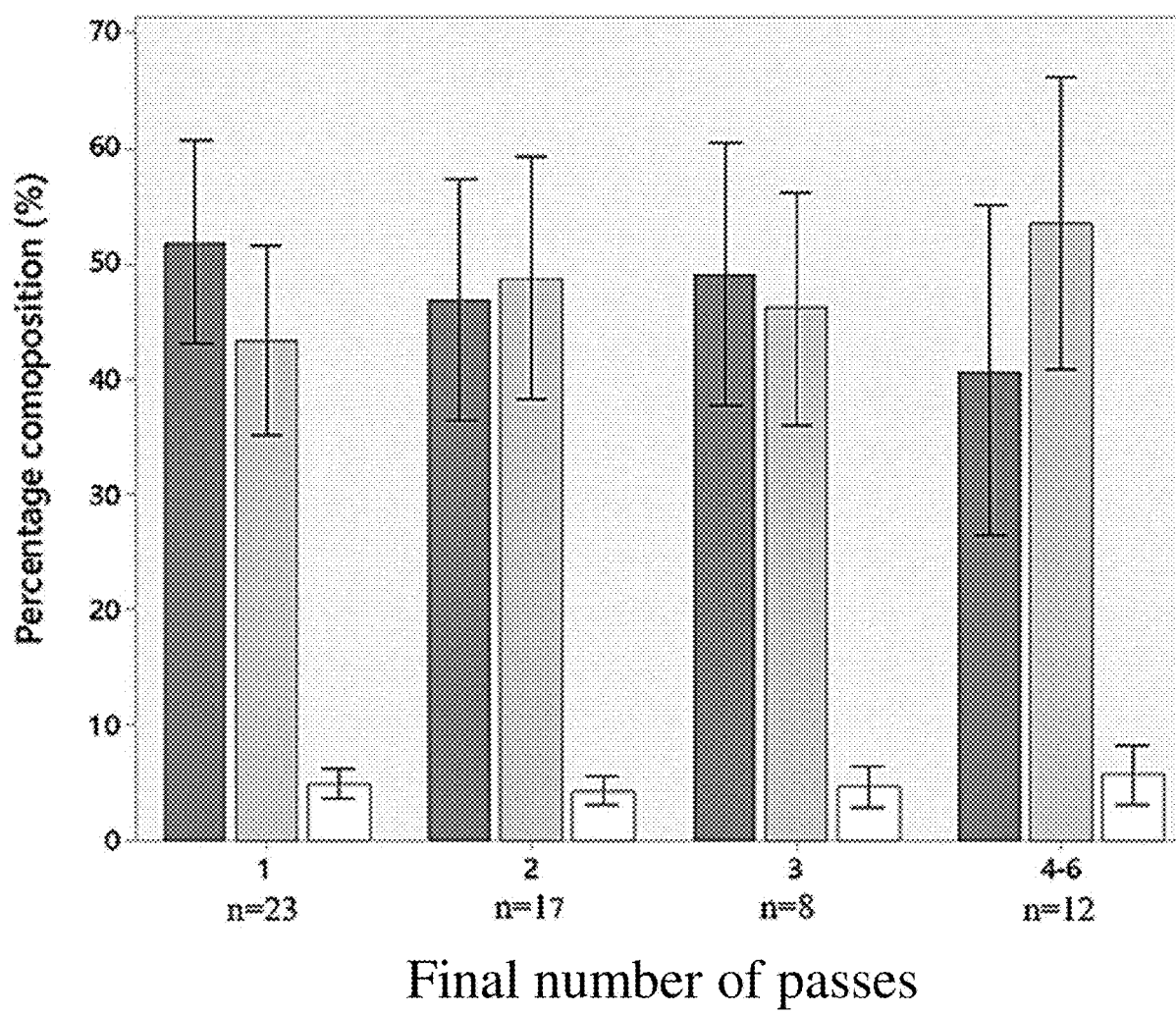
FIG. 39 depicts the mean composition in the first study of combined clot fragments for cases consisting of a total of one, two, three or four to six passes. The bars represent the mean composition. Individual standard deviations were used to calculate the intervals.

The combined clot burden removed per pass is depicted in FIG. 38. Similar to other studies of clots removed in thrombectomy, a broad distribution in the RBC and fibrin composition was observed in the first study. The WBC composition was consistently marginal across all cases. The mean composition of the clot combined from all passes was 46.4%±23.1% RBCs, 48.9%±22.0% fibrin and 4.7%±3.1% WBCs. In cases consisting of a total of 1, 2, 3 or 4 to 6 passes the average RBC content of the fragments combined from all passes was 51.8%±20.6%, 46.9%±20.3%, 49.1%±13.5% and 40.8%±22.6% respectively as shown in FIG. 39. FIG. 39 specifically depicts the mean composition in the first study of combined clot fragments for cases consisting of a total of one, two, three or four to six passes. The bars represent the mean composition. Individual standard deviations were used to calculate the intervals. In this combined clot analysis, regardless of the number of passes required to retrieve the clot there was no significant difference in the RBC, fibrin and WBC compositions between the 4 groups (p=0.490, 0.487 and 0.658 respectively).

Figure 40A:
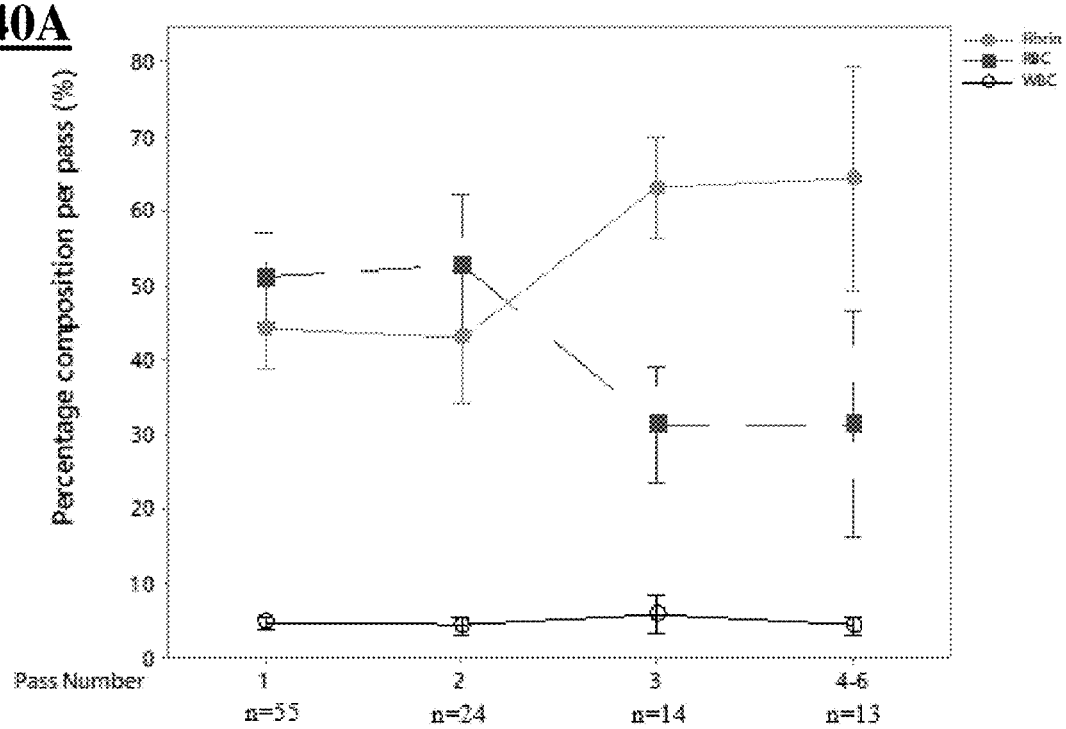
FIG. 40A depicts the mean RBC, fibrin and WBC composition of 106 clot fragments that were retrieved in Pass 1, 2, 3, 4, 5, 6 from all cases in the first study.
Figure 40B:
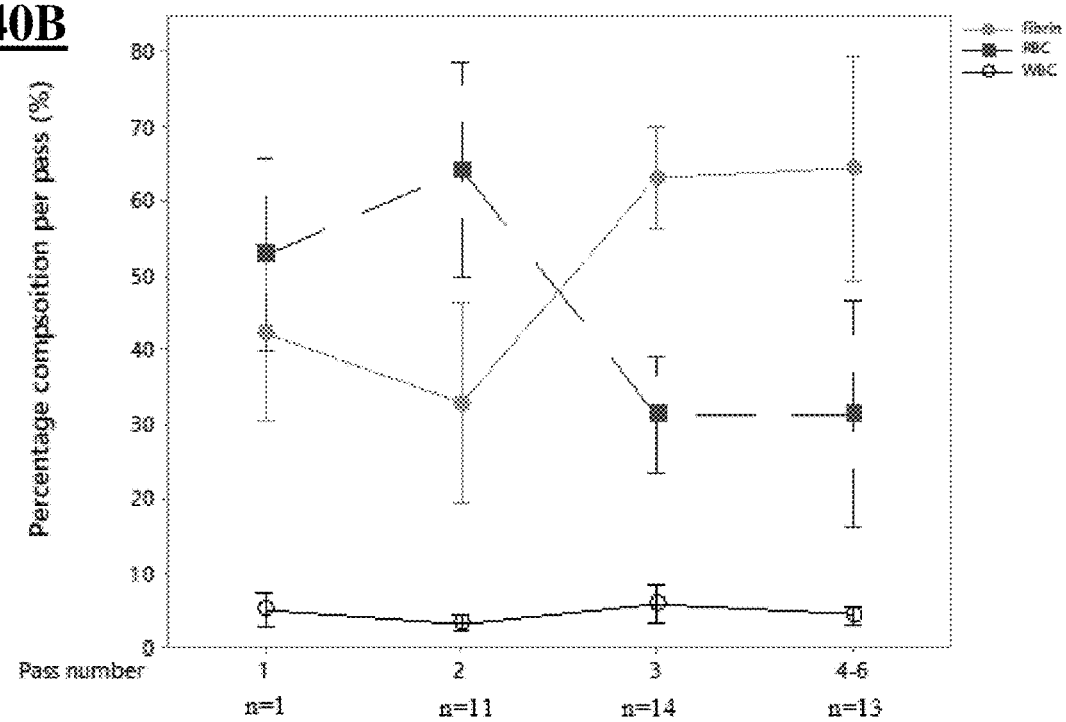
FIG. 40B depicts the mean RBC, fibrin and WBC composition of clot fragments (n=53 clot fragments) retrieved in Pass 1, 2, 3, 4, 5, 6 from those cases of the first study consisting of greater than two passes.

FIG. 40A depicts the mean RBC, fibrin and WBC composition of 106 clot fragments that were retrieved in Pass 1, 2, 3, 4, 5, 6 from all cases in the first study and shows that the mean RBC composition of material retrieved in passes 1 and 2 (51.1%±22.1% and 52.7±22.2% respectively) was significantly higher (p≤0.001) than the RBC composition in pass 3, and passes 4 to 6 combined (31.2%±13.2%, 34.1%±25.5%, 22.5%±31.6%, 37.7%±21.9% respectively). The inverse pattern was observed for fibrin composition, with clot fragments retrieved in passes 1 and 2 associated with a significantly lower (p≤0.001) fibrin composition (44.2%±20.9% and 43.0%±21.0% respectively) when compared to clot fragments retrieved in passes 3, and passes 4 to 6 combined (63.0%±11.9%, 61.6%±25.8%, 72.9%±30.7% and 58.5%±19.8% respectively). The RBC and fibrin composition of clot fragments retrieved in pass 1 when compared to those retrieved in pass 2 did not differ significantly (RBC comparison; p=0.501, fibrin comparison; p=0.963). FIG. 40B depicts the mean RBC, fibrin and WBC composition of clot fragments (n=53 clot fragments) retrieved in Pass 1, 2, 3, 4, 5, 6 from those cases of the first study consisting of greater than two passes. For both graphs the mean RBC, fibrin and WBC values are displayed for each pass. The individual standard deviations were used to calculate the intervals shown When cases consisting of 1 and 2 passes only are excluded from the analysis as illustrated in FIG. 40B, similar findings were observed. This confirms that in complex cases consisting of multiple passes, the clot fragments retrieved after pass 2 have a significantly higher Fibrin composition in comparison to the first 2 passes and generally no trends were observed regarding WBC.

FIG. 41 represents the RBC, fibrin and WBC composition of clot fragments retrieved in each pass over the 60 cases of the first study. Thirty-two (23.2%) out of 138 passes failed to retrieve at least some clot material. Of the cases that required just 1 or 2 passes to remove the clot fragments, only 12.2% of these cases involved an attempt where clot material was not removed (5/41 passes). In more complex cases involving 3 to 6 passes, 84.2% of these cases involved at least one pass where clot fragments were not removed (16/19 passes).

A clot retrieval device, such as clot retrieval device 200, was used for 90% of passes (124 passes), with a direct aspiration by catheter technique used in the remaining 10% of passes (14 passes), as shown in FIG. 36. Direct aspiration was used as a first line treatment in 10 cases. There were 3 single-pass direct aspiration cases, and in each of these cases clot material was successfully retrieved. Following 5 of the direct aspiration passes the technique was converted to the clot retrieval device for the remainder of the passes (36%). Additionally, direct aspiration failed to retrieve clot material in 2 passes (14%). There was only one case in which the technique was changed from the clot retrieval device to direct aspiration; in this 3-pass case, after a first-line clot retrieval device pass, direct aspiration was applied for the 2 subsequent passes. Among the 124 clot retrieval device passes, 30 passes failed to retrieve clot material (24%). In summary, 50% of direct aspiration passes (7 out of 14 passes) either failed to retrieve clot or converted to the clot retrieval device; where as 25% of clot retrieval device passes (31 out of 124 passes) failed to retrieve clot or converted to direct aspiration.

The average RBC, fibrin and WBC composition of clots retrieved using the clot retrieval device was 44.1%±22.7%, 51.1%±21.7% and 4.8%±3.2% respectively. The mean RBC, fibrin and WBC composition of clots retrieved by direct aspiration was 64.4%±18.1%, 31.6%±16.6% and 4.0%±2.2% respectively. The difference in the RBC and fibrin composition of fragments retrieved by direct aspiration versus the clot retrieval device was statistically significant ($p=0.003$ and $p=0.002$ respectively), while the WBC composition did not differ ($p=0.265$). The most striking difference in the compositional analysis of clots recovered by both techniques is that for direct aspiration, no clot fragments with greater than 56.4% fibrin were retrieved (6.4-56.4% fibrin (41.2%-91.8% RBC) whereas the range in composition of clot fragments retrieved by the clot retrieval device encompasses the full range of clot composition seen in the study, 9.2-92.3% fibrin (0.1-89.9% RBC). These results suggest that the clot retrieval devices, such as device 200, are capable of retrieving clots with a wide range of fibrin composition, while direct aspiration may not perform as well at retrieving clot fragments with a high fibrin composition.

Eighteen cases (30%) involved occlusions of the ICA alone and occlusions of the ICA extending into the MCA (see FIG. 36). On average, 2.3±1.3 passes were required to retrieve these clots, in comparison to 2.4±1.8 passes required to retrieved clots with no ICA involvement (MCA, ACA and Basilar artery). This difference was not statistically different ($p=0.760$). However, between the same groups a significant difference was found in the RBC and fibrin composition of clots retrieved; occlusions of the ICA only, and ICA and MCA collectively were associated with a significantly greater ($p<0.001$) RBC composition (61.3%±19.0% in occlusions involving the ICA versus 40.2%±21.8% in non-ICA vessels), and significantly lower ($p<0.001$) fibrin composition (34.3%±17.3% in the ICA versus 54.9%±21.0% in non-ICA vessels) in comparison to clot fragments retrieved from occlusions that did not involve the ICA.

Further, rt-PA was administered to 38 patients (63.3%). Of these cases, the average number of passes required to retrieve the clot fragments was 2.1±1.3 passes in comparison to 2.7±1.7 passes in cases where rt-PA was not administered. This difference was not statistically different ($p=0.127$). The average RBC, fibrin and WBC composition of clot fragments retrieved from cases where rt-PA was administered was 51.9%±18.2%, 43.2%±17.0%, 4.9%±2.6%, in comparison to 40.8%±21.4%, 54.1%+20.1% 5.1%+3.5% in cases where rt-PA was not administered. The difference in RBC and fibrin composition between the two groups was statistically different ($p=0.048$ and $p=0.039$ respectively), while there was no statistical difference in the WBC composition ($p=0.839$).

Figure 42:
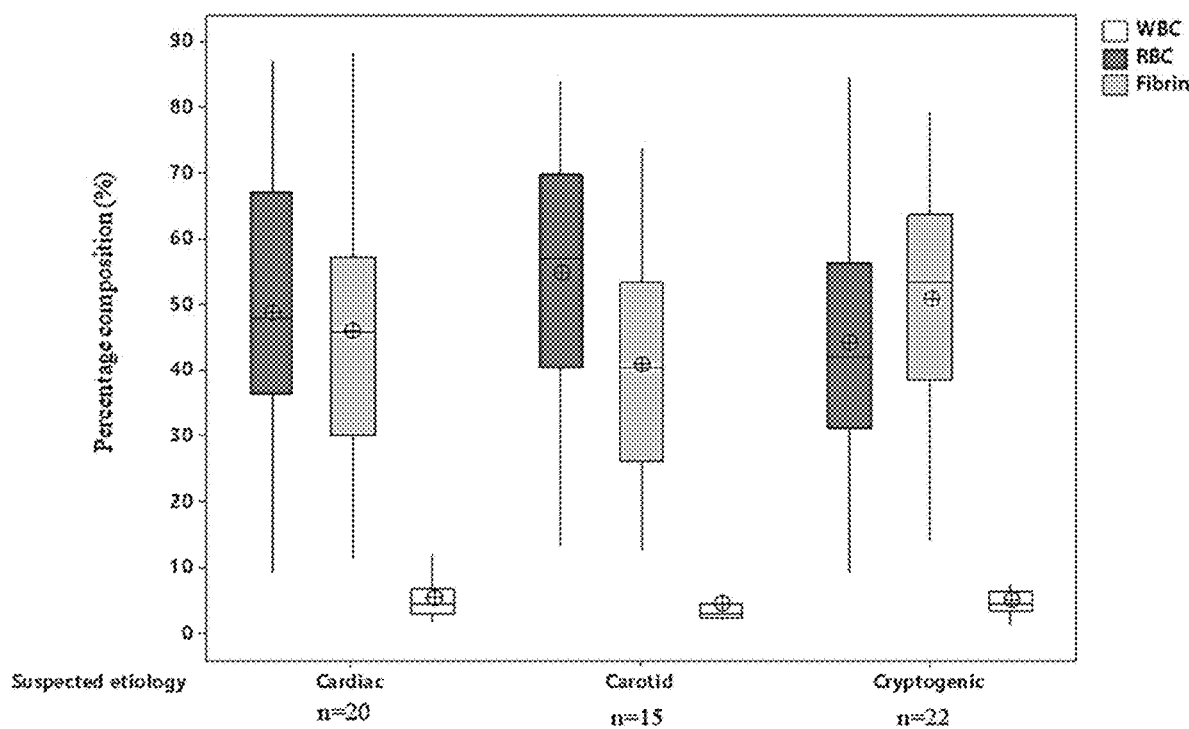
FIG. 42 depicts RBC, fibrin and WBC composition of the overall clot where fragments from each pass were combined and grouped according to cardioembolic, atheroembolic or cryptogenic aetiology. The interquartile range boxes, whiskers and median lines are shown on the graph. The mean RBC, fibrin and WBC composition for each aetiology is denoted by the symbol +.
Figure 43:
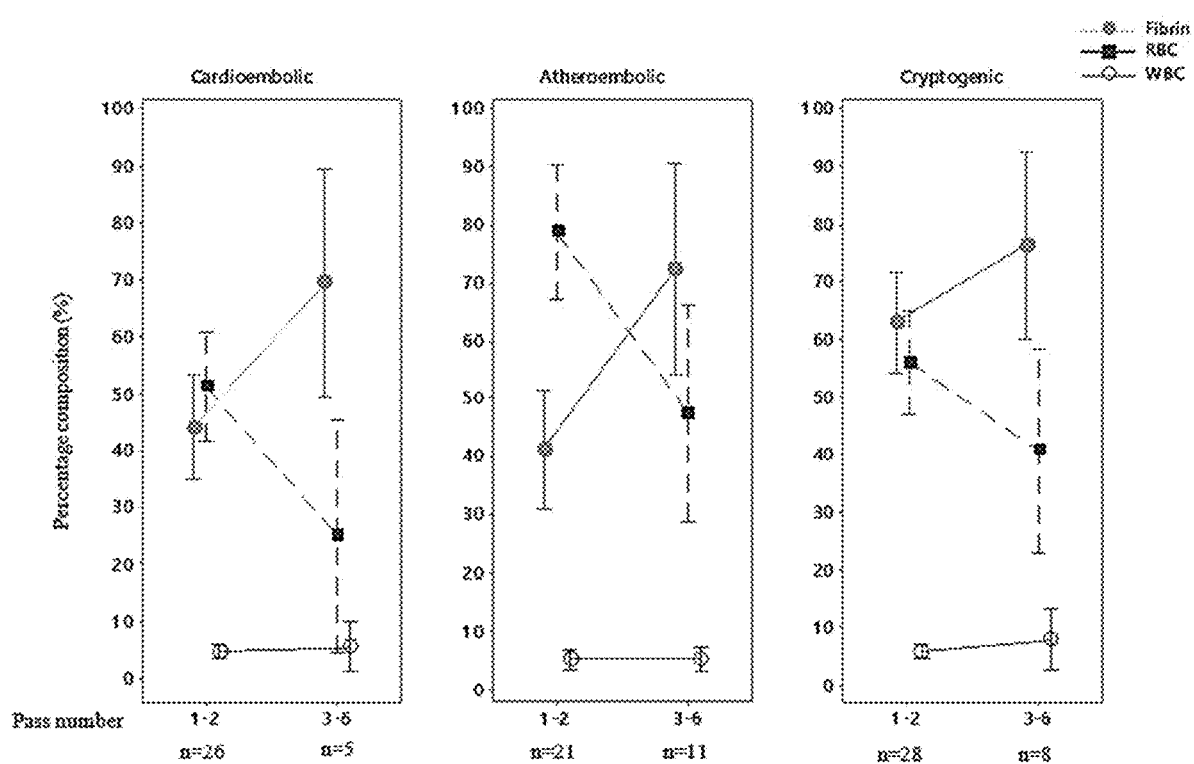
FIG. 43 depicts a breakdown of the percentage RBCs, fibrin and WBCs of fragments retrieved in passes one to six from patients with cardioembolic, atheroembolic and cryptogenic aetiology.

Analysis of clots retrieved from patients with the TOAST classifications of cryptogenic, atheroembolic and cardiogenic are shown in FIGS. 42-43. In particular, the composition of the full thrombus load recovered in the procedure, shown in Figure FIG. 42, does not show a remarkable difference between groups. FIG. 42 depicts RBC, fibrin and WBC composition of the overall clot where fragments from each pass were combined and grouped according to cardioembolic, atheroembolic or cryptogenic aetiology. The inter-quartile range boxes, whiskers and median lines are shown on the graph. The mean RBC, fibrin and WBC composition for each aetiology is denoted by the symbol+. The average RBC and fibrin composition of the entire thrombus load retrieved from cardioembolic, atheroembolic and cryptogenic stroke patients was 48.7%+23.1%, 54.9%±18.8%, and 44.2%±17.4% RBCs respectively, and 46.0%±21.9%, 40.7%±16.4% and 50.8%±16.5% fibrin respectively. Using a one-way ANOVA, the RBC and fibrin composition of the overall thrombus load removed did not differ significantly between the three different aetiology groups (RBC comparison between aetiologies; $p=0.286$, and fibrin comparison between aetiologies; $p=0.269$).

Examination of the thrombus composition in each pass is shown in FIG. 43. FIG. 43 specifically depicts a breakdown of the percentage RBCs, fibrin and WBCs of fragments retrieved in passes one to six from patients with cardioembolic, atheroembolic and cryptogenic aetiology. The mean RBC, fibrin and WBC compositions per pass for each group are illustrated on the graph. The individual standard deviations were used to calculate the intervals shown. Although the ratio of fibrin to RBCs in passes 1 and 2 was similar in cardioembolic and cryptogenic aetiology, 51.2%±23.8% and 44.9%±18.5% respectively ($p=0.282$), thrombi retrieved in passes 1 and 2 from atheroembolic aetiology has higher RBC composition (65.1%). This difference is statistically significant in the case of cryptogenic stroke ($p=0.003$), but while trending in the same direction it is not statistically different when compared to cardioembolic aetiology ($p=0.077$).

In FIGS. 42-43, there was no significant difference in the RBC, fibrin and WBC composition of fragments retrieved in passes 3-6 between the three aetiology groups ($p=0.479$) as determined using a one-way ANOVA. There was a clear significant increase in the fibrin composition between the first two passes and the later passes among all aetiology groups. Atheroembolic clots were associated with a significant preferential removal of RBC dominant fragments in passes 1 and 2 in comparison to later passes. Further analysis, just focusing on the 30% of cases that had greater than 2 passes, show the same trends as the combined analysis described above (this analysis in not provided in this manuscript).

Final angiographic reperfusion rates were 90% mTICI≥22b, 73.3% mTICI≥2c and 53.3% mTICI 3 score (see, e.g., FIG. 36). The removal of thrombus material in passes 1-3 was associated with a higher percentage of final mTICI 2c-3 scores in comparison with passes 4 to 6; in cases consisting of a total of 1, 2, 3, or 4 to 6 passes the rate of final mTICI≥2c was 78.3%, 77.8%, 85.7% and 50% respectively, while the rate of final mTICI≥2b was 87%, 88.9%, 100% and 91.7%. The full distribution of reperfusion outcomes is shown in FIG. 36.

The mean fraction of RBCs and fibrin composition was calculated for cases with a final mTICI of 2b, 2c and 3. Cases with mTICI of 0, 1 and 2a were excluded in this analysis. There was no significant association between RBC and fibrin composition with final mTICI score ($p=0.173$ and $p=0.182$ respectively), although there was a trend towards an increasing RBC content with increasing mTICI scores. The respective mean RBC and fibrin compositions for cases with a final mTICI of 2b or greater are as follows; mTICI 2b: 37%±15% and 58%±15%, mTICI 2c: 42%±22% and 52%±19%, mTICI 3: 54%±19% and 42%±18%. Similarly, there was no significant correlation between mTICI score after each pass and the RBC and fibrin composition of the fragments retrieved in that pass (p=0.193, 0.229 respectively).

In a second study of this disclosure, the preparation of platelet-contracted clot analogues (PCCs) and non-contracted clot analogues (NCCs) were evaluated. Blood mixtures of various haematocrits were prepared from citrated ovine blood by mixing platelet-rich plasma (PRP) and platelet-poor plasma (PPP) with different quantities of red blood cells (RBCs). Clots were prepared from these blood mixtures after reversing the anti-coagulant. A mechanical test, previously used to test embolic clots recovered from cases of acute ischemic stroke (AIS), was performed to measure the mechanical behavior of the clot analogues and allow comparison to the ex vivo clots. Scanning electron microscopy and histology were used to investigate the microstructure and composition of the clot analogues. Association between the mechanical properties of the clots and their behavior when they interact with mechanical thrombectomy devices was carried out using an in vitro silicone artery flow-model.

In the second study, fresh venous blood was collected from sheep for the preparation of the clot samples for testing. Ovine blood was chosen as it has been found to be a suitable substitute for human blood for coagulation studies. Blood was collected and ACPD (Adenine citrate phosphate dextrose) anticoagulant solution was added. The blood was then transported to the lab and stored at room temperature until used. All clots were prepared within 5 hours of blood collection.

To begin clot preparation, the blood was centrifuged at 180 g for 10 minutes to form a top layer of platelet-rich plasma (PRP). After isolation of the PRP, the remaining blood mixture was then centrifuged again at 2200 g to create platelet-poor plasma (PPP). The PPP was carefully collected, ensuring that the buffy layer was not disrupted. The buffy layer was then removed as waste to isolate the RBC beneath. Two families of clot analogues were produced: (1) PCC and (2) non-contracted clot (NCC). PCCs were formed from blood mixtures with different haematocrit (H) by mixing the platelet rich plasma (PRP) with the red blood cells in controlled ratios. Similarly, the NCCs were produced by mixing the platelet poor plasma (PPP) with the red blood cells in the same ratios.

Once the various blood mixtures were produced, coagulation was initiated by the addition of a 2.06% calcium chloride solution to the blood components in a 1:9 ratio. The clots were matured overnight in an incubator at 37° C. Confirmation of contraction was established and assessed gravimetrically by weighing the solid and liquid phases in the clot molds. The color of the serum was also monitored to establish if the RBCs had been incorporated into the clot or remained in suspension after clotting. The resulting cylindrical clots were cut to an appropriate height and placed in PBS for 30 minutes prior to mechanical testing.

A Dynamic Mechanical Analyzer (DMA, Q800; TA Instruments, New Castle, Del.), which has a force resolution of 0.00001N and a strain resolution of nm, was used in the second study to investigate the mechanical behavior of the clot analogues. The test was carried out using a submersion compression clamp in the controlled force mode and the samples were tested in saline at 37° C. Cylindrical clot samples were cut to have an approximate height of 3 mm and calipers were used to measure the diameter, 220-grit sandpaper was adhered to the compression disk to prevent the samples from slipping out during the test. The samples were first subjected to force ramp to 15N at a rate of 0.5N/min.

MSB staining in the second study was selected as an appropriate method to stain for fibrin and erythrocytes. Sections the clots were fixed in a 10% buffered formalin solution after removal from the incubator, and left for 48 hours. The samples were then embedded in a paraffin wax and cut into 5 µm sections. The sections were dewaxed and hydrated with distilled water in preparation for staining.

Sections were photographed using an Olympus VS120 digital slide scanner. The objective lens, brightness, and height of the condenser, as well as the saturation, brightness, and contrast settings of the image acquisition software were standardized to ensure uniformity of the digitized images. Images were acquired at 40× magnification from 5 randomly chosen areas of the slide.

The analogue samples were fixed with 2.5% glutaraldehyde and dehydrated in a series of ethanol concentrations up to 100%. The samples were frozen in liquid nitrogen and fractured so that the interior surface of the clot analogues could be examined. The samples were then critical-point dried, mounted and sputter-coated with iridium.

The second study also included a three-dimensional in vitro model based on the human intracranial circulation was used for the thrombectomy experiments. The model consisted of the complete intracranial circulation with both carotids and vertebral arteries, complete circle of Willis, and functional anterior and posterior communicating arteries with distal circulation up to M2 and A2. Saline was heated to 37° C. and circulated through the model using a peristaltic pump. The rate of flow through the model was set to be within the range of clinically representative flow rates. Different clot types were cut to an appropriate size and introduced into the in-vitro flow model to simulate a large vessel occlusion of the middle cerebral artery. The clots were cut to have dimensions of 3 mm×3 mm×8 mm and were introduced into the carotid artery and allowed to migrate in the vessel under pulsatile flow to the target location to facilitate M1 occlusion.

Two retrieval techniques were used in the second study to retrieve the clot analogues; contact aspiration with an aspiration catheter (ADAPT) and retrieval via stent-retriever combined with local aspiration into an intermediate catheter (Solumbra). An ACE 64 (Penumbra, Alameda, Calif., USA) intermediate catheter was used for the former, and a 33×5 mm stentriever device, as previously described with respect to device 200, and an ACE 64 intermediate catheter were used for the latter. A Medium Support 0.014" straight tip guidewire (Boston Scientific, Marlborough. USA) and an ev3 Rebar (ev3, Irvine, Calif., USA) 0.021" microcatheter were used to cross the clot for the retrievals using the stent-retriever. For contact aspiration alone, the catheter was advanced to the face of the clot over the guidewire and aspiration was applied using a Penumbra aspiration pump (Penumbra. Alameda, Calif., USA). The interaction of the clot with the devices was investigated by observing the behavior of the clot and device during retrieval.

Results of the second study are explained as follows. The weight of the blood mixtures and the resultant clots were measured on a gravimetric balance. Volume reduction due to contraction was calculated by expressing the weight of each clot as a percentage of the original blood mixture from which it was derived. As such, the weight of NCCs was equal to the weight of the blood mixture. However, PCCs had a reduced weight due to a reduction in volume in the form of expelled serum. An additional gravimetric assessment of the NCCs was carried out whereby the NCCs were mechanically compressed by spinning twice in a centrifuge for 10 minutes at 2200 g. The final weight of these mechanically contracted clots also correlated to the % Hematocrit of the blood mixtures, thereby confirming that RBCs, entrapped in the blood clot at the time of clot initiation, were a limiting factor for the final clot volume.

Figure 44:
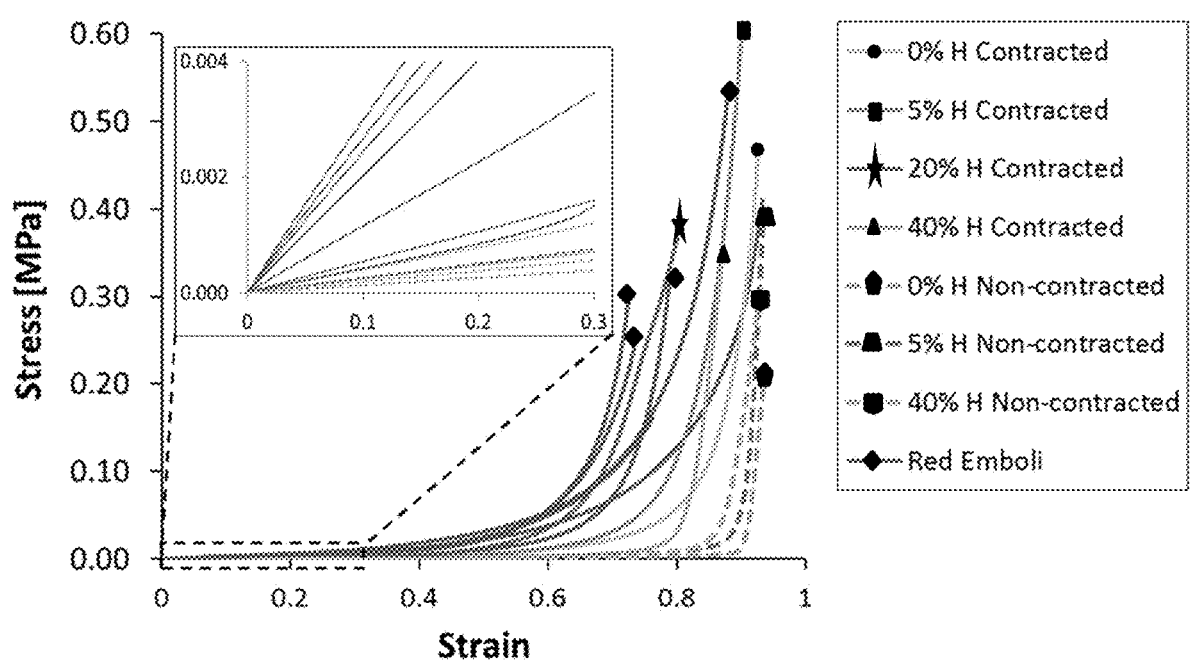
FIG. 44 depicts a stress-strain curve from the DMA testing comparing the mechanical behavior of both the contracted and non-contracted clot groups during the second study of this disclosure.

All clots of the second study exhibited non-linear stress-strain behavior, with two distinct regions, as shown in FIG. 44. In the initial region, large deformation can be seen occurring at small levels of stress, as the fibers rearrange within the material network. However, as the load is increased, the fibrin fibers aligned perpendicular to the direction of the applied force and there was a sharp increase in stress as the, now aligned, fibers were stretched. The mechanical testing showed that the compressive stiffness of the PCCs was higher than that of the NCCs across all haematocrits. There was a non-linear correlation between clot stiffness and haematocrit for PCCs. At low levels of strain the 5% H clot was found to be the stiffest clot in the contracted clot group, followed by the 20% H, 0% H and 40% H respectively. However, for large strains (>60%), the 20% H clot was found to have the greatest stiffness, followed by the 5% H and the 0% H, with the 40% H contracted clot having the lowest stiffness at all strain levels. In the NCC group, all the clots had a very similar profile with negligible difference in compressive stiffness.

Figure 45:
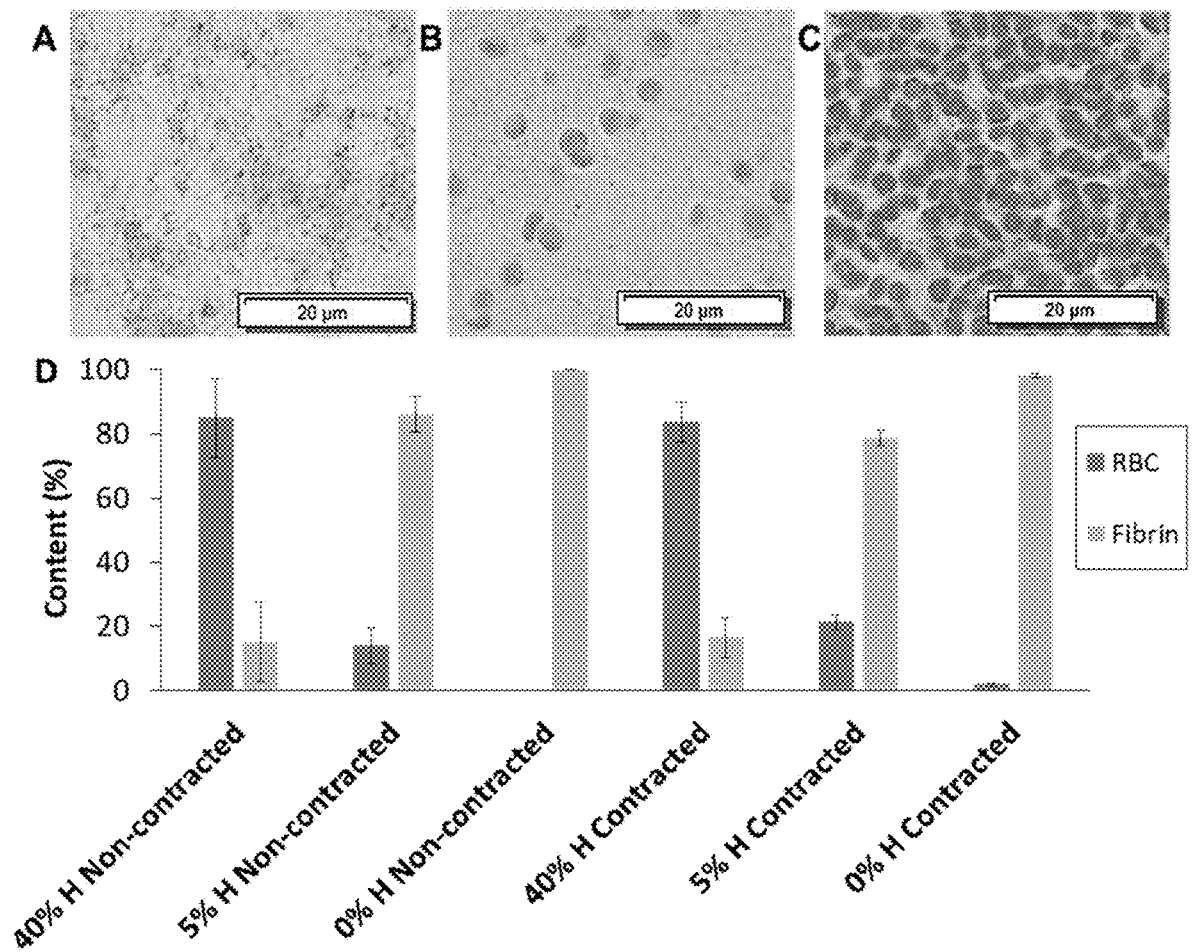
FIG. 45 depicts MSB staining of contracted and non-contracted clot samples across multiple haematocrits.

The mechanical behavior of the clot analogues were compared to thromboembolic secondary to AIS that had been removed via aspiration thrombectomy. The clot analogues spanned the range of these ex vivo emboli. Both groups of clot analogues were found to have lower stiffness than the human thromboemboli at low levels of strain (e.g., <30%), however the PCCs reached similar levels of stress at higher levels of strain. The NCCs were found to be an order of magnitude lower across all levels of strain. Histological examination of the clot analogues shows little difference in the fibrin and RBC content when comparing the PCCs and NCCs at the same haematocrit levels, as shown in FIG. 45.

Figure 46:
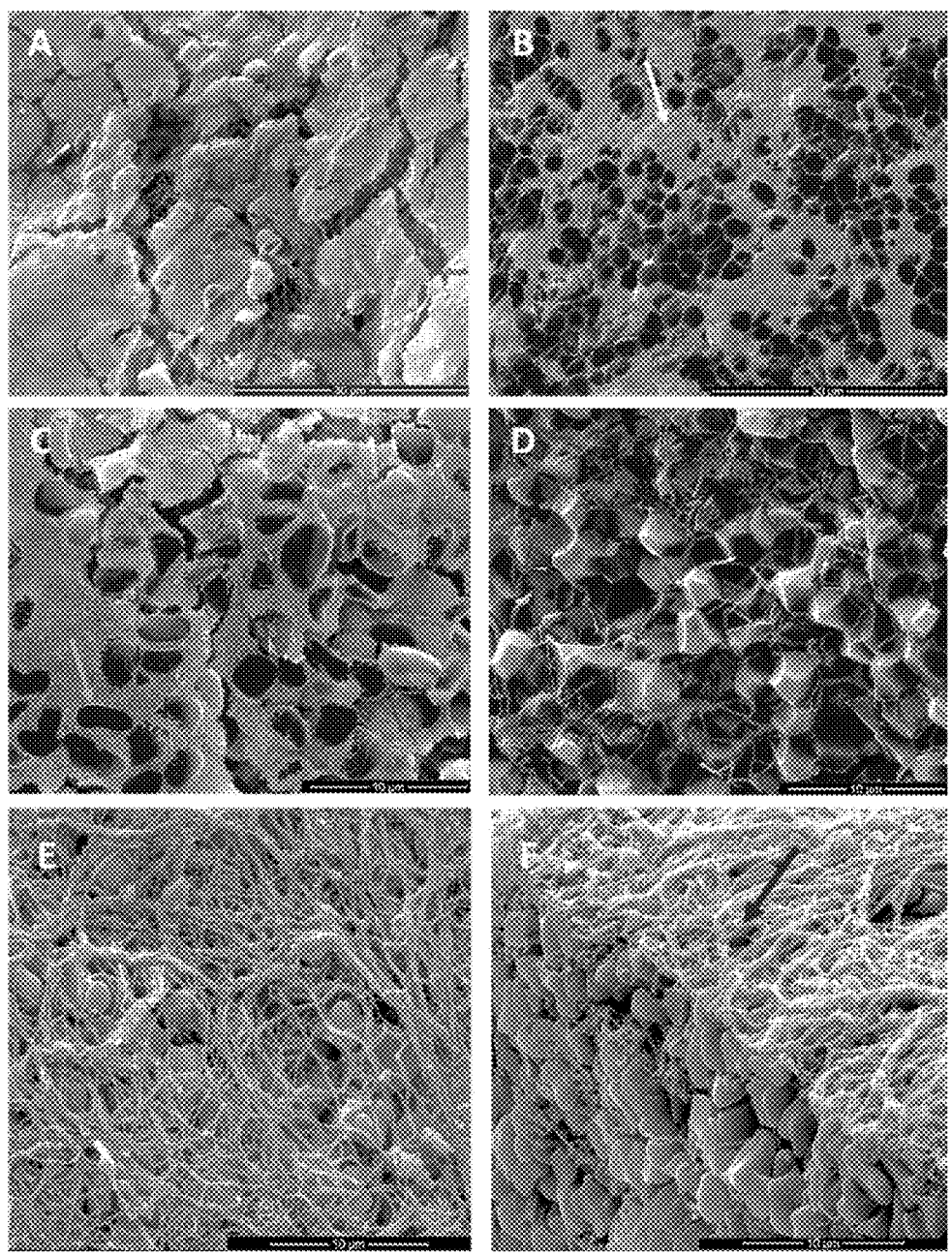
FIG. 46 depicts colored SEM images taken of the clot analogues, with fibrin colored lighter and RBCs colored darker.

However, under SEM the microstructure of both groups were significantly different, as shown in FIG. 46 compares SEM images from NCCs and PCCs. In particular, images A and B of FIG. 46 show the interior of a 5% H non-contracted and contracted clot analogue respectively, with the white arrow indicating an area of compressed fibrin. Image C of FIG. 46 depicts the interior of a 40% H non-contracted. The arrow highlights a typical biconcave-shaped RBC trapped within a loose fibrin mesh. Image D of FIG. 46 shows the polyhedrocytes present in the interior of a 40% H contracted clot analogue. Images E and F of FIG. 46 are SEM images illustrating the large fibrin strands covering the exterior surface of the clot analogues (Image E), comparing the interior and exterior surfaces (Image F) of the clot, with the arrow indicating the outer surface Two types of fibrin fibers were observed, thick fibers (179.8 nm±80 nm) with relatively few branches and thin hyper branched fibers (45.75 nm±11.5). The former was observed in abundance on the exterior of the clots and traversing the interior, while the latter is seen in the interior only. When platelets were observed to interact with the fibrin network, it was through attachments to the thicker fibrin fibers. Resembling a porous sponge in the NCCs, the thin and highly branched fibrin occupies the spaces between the red blood cells and thicker fibrin fibers (Images A and C). This spongy fibrin network is significantly compressed through the action of clot contraction (Images B and D), appearing as a very thin layer on the faces of closely packed RBCs in Image D.

Noticeable changes in red blood cell shape were apparent when comparing NCCs and PCCs. The typical biconcave-shaped RBCs were clearly observed in the NCCs, whereas the PCCs consist of compressed fibrin structures, compacted around polyhedron-shaped RBCs, so called 'polyhedrocytes'. The thicker fibrin were seen to entrap the polyhedrocytes in a latticework of fibers. Imprints seen where the fibrin had come away from the flat faces of the RBCs established that contractile forces exerted by platelets, and conveyed through the fibrin, are responsible for the RBC shape change.

By varying the haematocrit of the blood mixtures used to form the clots the proportion of RBCs incorporated in the clot was altered, in all cases it was confirmed that the RBCs had been captured by the fibrin network by observation that the resultant serum was clear and straw colored, although for the 40% H clots the serum had slightly pink coloration, that indicated that a very small proportion of the RBCs did not get included. In NCCs, no remarkable difference was observed in the interior microstructure when comparing clots formed with a different % H, however in PCCs, clots with a smaller number of RBCs incorporated have large seams of fibrin surrounding smaller clusters of compacted RBCs, whereas clots with a large number of RBCs consist mainly of compacted RBCs with only sparse fibrin interlaced between them. All clot analogues were found to have a fibrous layer containing thicker fibrin fibers covering the exterior of the clot (Image E and F). An envelope of fibrin was observed in all of the clots, with few RBCs visible. In PCCs, a higher concentration of platelets is also visible on the outside of the clot when compared to the interior.

Mechanical thrombectomy was also simulated in the second study in an in-vitro flow model using two approaches—(1) contact aspiration with an aspiration catheter and (2) retrieval via stent-retriever (e.g., device 200 of this disclosure) combined with local aspiration into an intermediate catheter (IC). For the aspiration only technique, it was not possible to fully aspirate PCCs formed with 0% H or 5% H into the aspiration catheter, however the clots were subsequently successfully retrieved by removing the catheter and clot en bloc. NCCs were successfully aspirated fully through the aspiration catheter. The results from the combined approach was similar. The lower haematocrit PCCs were not fully retrieved into the IC using the stent retriever requiring en bloc removal of the clot with the stent retriever and IC, however it was possible to fully retract the NCCs and stent retriever through the catheter. The clots were not observed to lose fragments during the retrieval steps, but a considerable reduction in volume was noted for the NCCs collected.

NCCs and PCCs formed from blood with a higher haematocrit were fully retrieved into the intermediate catheter, either with aspiration alone or through use of the stentriever. However, considerably more fragmentation was observed for the 40% H PCC compared to the 40% NCC as they entered the IC using both techniques. Both clot types resulted in the collection of numerous fragments in the collection chamber of the aspiration pump.

In the second study, under compression testing the clot analogues were found to have a similar, non-linear stress-strain relationship and mechanical behaviour to published data for clot material. It was observed that platelet contraction had the effect of increasing stiffness and together with adjustment of the haematocrit enabled close matching of stiffness to representative thromboemboli of AIS origin. The greater stiffness of the PCCs can be explained by examining their microstructure since contracting platelets have been found to actively remodel the fibrin network by tightening the fibres, and thus enhancing clot stiffness. This is evident from the SEM images of the contracted clot group. The NCCs are found to consist of a loose fibrin mesh, whereas the PCCs consist of stretched, compacted fibrin. The loose fibrin mesh is likely to be more easily deformed under compression compared to the compacted fibrin, thus resulting is lower clot stiffness.

In clots that contain RBCs, the shape of the RBCs and their interaction with the surrounding fibrin were used to understand how the mechanical properties changed through the process of platelet driven contraction. Prior to clot contraction RBCs maintain a biconcave shape and were homogeneously dispersed throughout the fibrin network, following platelet contraction the RBCs are compacted closely with individual cells exhibiting a polyhedrocyte shape. Red blood cells were unlikely to change their volume under compression, but they were highly deformable, which for example, enabled them to assume a cigar shape when they required to squeeze through capillaries. The cells shape changed to a polyhedron, assumed during thrombus contraction, imparts a space-efficient, close-packed structure to the clot. Close packing of red-blood cells created a water-tight seal and allows a maximum reduction in clot volume, both of which are important for haemostasis and reperfusion, respectively.

Contracted clots formed from blood mixtures with a high haematocrit were dominated by red blood cells that were homogeneously dispersed throughout. However, clots formed from lower haematocrit blood mixtures exhibited grouping of the red blood cells into RBC rich domains, surrounded by compressed fibrin. Local clustering of RBCs could imply a mechanism to promote movement of RBCs out of the fibrin meshwork during clot contraction. Thicker fibrin fibres surrounding the RBCs were observed to leave imprints in the faces of the polyhedrocytes, indicating that it was through these thick fibrin fibres that the platelet-driven contraction of the clots is propagated. The hyperbranched, thin-fibre fibrin was observed to compress significantly after contraction, which indicates that it is the compression of this porous material with the subsequent expulsion of serum, which accounts for the majority of clot volume reduction between initial clot formation and the final contracted state. The RBCs were found to be homogeneously distributed throughout these statically formed analogues in both groups, with a fibrin rich layer enveloping all clots. For clots that contained platelets, the platelets were also observed in much greater abundance on the outer layer.

In mechanical testing, the 40% H clot had the lowest compressive stiffness of the PCCs, which was likely due to the lower levels of fibrin present to reinforce the matrix. However, the clots formed from 20% H blood had a greater compressive stiffness than 0% H and 5% H clots. The trend suggested that contracted clots with a combination of a relatively large quantity of tightly entrapped RBCs with enough platelet-fibrin surrounding them were least likely to change volume during thrombectomy.

SEM analysis of the fibrin and RBC microstructure clearly showed why the different clots formed from blood solutions with the same haematocrit varied in mechanical behaviour so much. Taken together, the significant difference in mechanical properties and microstructure but without an appreciable difference in histology, implies that examination of the histology of explanted human clots alone should not be used in isolation as a predictor of the mechanical behaviour of the clots in thrombectomy.

The second study therefore observed that a selection of repeatable clot analogues with mechanical properties that span the range of human thromboemboli have been created to be used for in vitro modelling of AIS and simulation of thrombectomy. Platelet contraction significantly affects clot volume and microstructure, and in turn clot stiffness. Although significant difference in mechanical properties and microstructure was observed between PCCs and NCCs, histological quantification of fibrin and RBCs in these clots did not show an appreciable difference. The implication is that histological studies alone of explanted human clots may not prove to be predictive of the mechanical behavior of the clots in thrombectomy FIG. 47 shows an example method or use 4700 for managing one or more acute ischemic events. The method or use can include step 4710 delivering any catheter of this disclosure to a site of a clot in the vasculature. The method or use can also include 4720 taking a first measurement of the clot using the spectroscopic sensing device at a first location of the site of the clot in the vasculature. The method or use can also include step 4730 generating a spectrum from the first measurement, whereby the spectrum relates to at least one of a chemical composition and physical properties of the clot.

Figure 48:
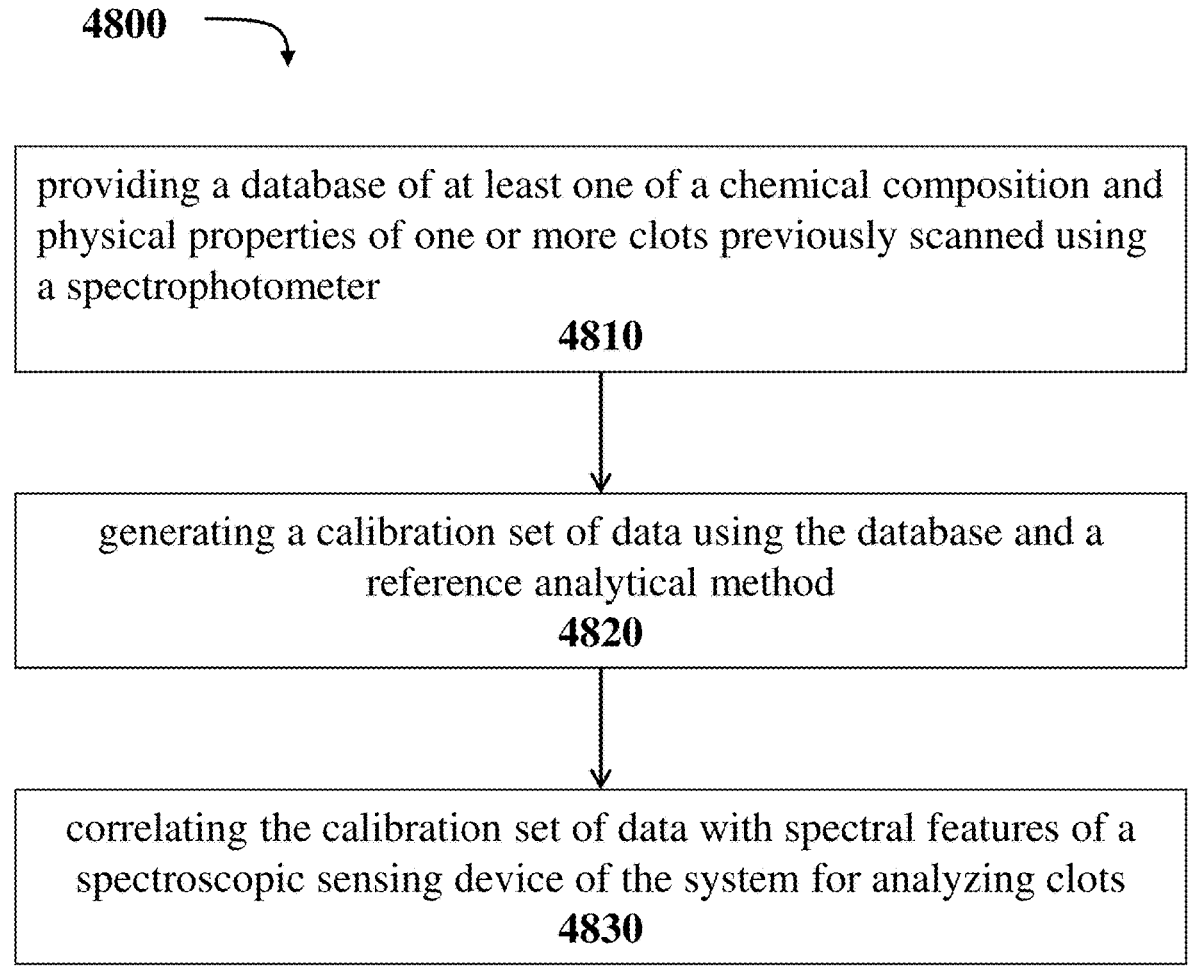
FIG. 48 shows a flow diagram depicting an example method or use of this disclosure for managing one or more acute ischemic events.

FIG. 48 shows an example method or use 4800 for calibrating a system for analyzing clots. The method or use can include step 4810 providing a database of at least one of a chemical composition and physical properties of one or more clots previously scanned using a spectrophotometer. Step 4820 can include generating a calibration set of data using the database and a reference analytical method or use. Step 4830 can include correlating the calibration set of data with spectral features of a spectroscopic sensing device of the system for analyzing clots.

FIG. 49 shows one embodiment of a flow diagram depicting an example method or use 4900 of this disclosure for managing one or more acute ischemic events. Method or use 4900 can include 4910 determining criteria of a clot; 4920 classifying the clot based on the criteria and generating a classification; 4930 determining an individualized treatment protocol for the clot based on the classification, the individualized treatment protocol comprising one or more techniques selected from using aspiration, restoring perfusion using a first reperfusion device; and/or restoring perfusion using a second reperfusion device; and 4940 treating the clot based on the individualized treatment protocol.

FIG. 50 shows an example method or use 5000 for managing one or more acute ischemic events. The method or use can include step 5010 delivering a guidewire through a microcatheter to a site of a clot in the vasculature, the guidewire comprising one or more sensors connected to or adjacent a distal end of the guidewire, the one or more sensors configured to measure properties of the clot in the vasculature. The method or use can also include 5020 sensing properties of the clot using the one or more sensors at a first location of the site of the clot in the vasculature. The method or use can also include step 5030 generating an output from the sensed properties, whereby the output relates to at least one of a chemical composition and physical properties of the clot.

FIG. 51 shows an example method or use 5100 for managing one or more acute ischemic events. The method or use can include step 5110 delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot. Step 5120 can include sensing properties of the clot using the temperature sensors at a first location distal of the clot, a second location in the clot, and third location proximal of the clot. Step 5130 can include generating an output from the sensed properties, whereby the output relates to at least one of a chemical composition and physical properties of the clot.

FIG. 52 shows an example method or use 5200 for making a guidewire for an endovascular medical system for treating a clot located in a target vessel. The method or use can include step 5210 forming a substantially planar distal end of the guidewire. The method or use can include step 5220 positioning one or more sensors on the guidewire for sensing the clot; and wherein the distal end is substantially planar on the distal end and wider than a remainder of the guidewire proximal thereof, and wherein the predetermined shape is configured to prevent the guidewire tip from entering a perforating vessel when the guidewire is delivered to the clot. It is to be understood that other steps described in this disclosure are contemplated for use with the method or use 5200 of FIG. 52.

FIG. 53 shows an example method or use 5300 for making a guidewire for an endovascular medical system for treating a clot located in a target vessel. Method or use 5300 can include step 5310 forming a substantially planar distal end of the guidewire. Method or use 5300 can include step 5320 cutting a predetermined shape into the distal end of the guidewire, wherein the distal end is wider than a remainder of the guidewire proximal thereof, and wherein the predetermined shape is configured to prevent the guidewire tip from entering a perforating vessel when the guidewire is delivered to the clot.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method or use step is present in the composition or article or method or use, but does not exclude the presence of other compounds, materials, particles, method or use steps, even if the other such compounds, material, particles, method or use steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method or use does not preclude the presence of additional method or use steps or intervening method or use steps between those steps expressly identified. Steps of a method or use may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The descriptions contained herein are examples illustrating the solution and are not intended to limit the scope. As described herein, the solution contemplates many variations and modifications of a system, device, and/or method or use that can be used to analyze one or more clots and individualize treatment based on the analysis. Variations can include but are not limited to alternative geometries of elements and components described herein, utilizing any of numerous materials for each component or element (e.g. radiopaque materials, memory shape metals, etc.), utilizing additional components, utilizing additional components to perform functions described herein, or utilizing additional components to perform functions not described herein, for example. These modifications would be apparent to those having ordinary skill in the art to which this invention relates and are intended to be within the scope of the claims which follow.

The specific configurations, choice of materials and the size and shape of various elements can be varied according to particular design specifications or constraints requiring a system or method or use constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

The following clauses list non-limiting embodiments of the disclosure:

1. A method or use for managing one or more acute ischemic events, the method or use comprising:
   determining criteria of a clot;
   classifying the clot based on the criteria and generating a classification;
   determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and
   treating the clot based on the individualized treatment protocol.
2. The method or use according to clause 1, wherein the classifying the clot is carried out in vivo.
3. The method or use according to clause 1, wherein the first reperfusion device is a stent retriever and the second reperfusion device is a pinch retriever.

4. The method or use according to clause 1, wherein the classifying the clot comprises one or more of a clinical exam, a blood test, a computerized tomography (CT) scan, a magnetic resonance imaging (MRI) scan, a carotid ultrasound, a cerebral angiogram, and an echocardiogram.

5. The method or use according to clause 1, wherein the determining criteria of the clot comprises:

performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

6. The method or use according to clause 1, wherein the first reperfusion device is a stent retriever configured to remove a clot or portions of a clot that are red blood cell rich and the second reperfusion device is a pinch retriever configured to remove a clot or portions of a clot that are fibrin-rich; and wherein if the classification demonstrates that the clot is red blood cell rich, then the individualized treatment protocol comprises:

passing the first reperfusion device by, through, or about the clot and then retracting the first perfusion device while engaging the clot in a lumen of the first reperfusion device to restore reperfusion to the vessel.

7. The method or use according to clause 1, wherein the first reperfusion device is a stent retriever configured to remove a clot or portions of a clot that are red blood cell rich and the second reperfusion device is a pinch retriever configured to remove a clot or portions of a clot that are fibrin-rich; and wherein if the classification demonstrates that the clot is fibrin-rich, then the individualized treatment protocol comprises:

passing the second reperfusion device by, through, or about the clot and then retracting the second perfusion device while pinching the clot to restore reperfusion to the vessel.

8. The method or use according to clause 1, wherein the determining criteria of the clot further comprises: interpreting information, by a computing device in operative communication with the clot, about the clot to determine in real-time levels of red blood cell content, white blood cell content, levels of fibrin, a clot size, a clot shape, and/or a clot location in the vasculature; and wherein the method or use further comprises:

receiving, through a graphical user interface of the computing device, the individualized treatment protocol;

monitoring, by the computing device, perfusion of the vessel with the clot; and, alerting, by the computing device, in response to perfusion being restored in the vessel.

9. The method or use according to clause 1, wherein the computing device is linked to a database comprising correlation data for interpreting information about the clot and determining the individualized treatment protocol;

wherein the database is remote from the computing device.

10. The method or use according to clause 1, wherein the determining criteria of the clot comprises:

delivering a catheter to a site of the clot in the vasculature;

taking a first reading of the clot by a using instrumentation for near infrared spectroscopy (NIR) coupled to the catheter at a first location of the site of the clot in the vasculature; and generating a spectrum from the first reading, whereby the spectrum relates to at least one of a chemical composition and physical properties of the clot.

11. The method or use according to clause 10, wherein the determining criteria of the clot further comprises: interpreting information contained in the spectrum to determine in real-time at least one of levels of red blood cell content, white blood cell content, levels of fibrin, a clot size, a clot shape, and a clot location in the vasculature.

12. The method or use according to clause 10, further comprising:

taking a second reading of the clot by using the instrumentation for NIR at a second location distal or proximal of the clot and the first location;

generating a spectrum from the second reading, whereby the spectrum of the second reading relates to at least one of a chemical composition and physical properties of the clot; and interpreting information contained in the spectrum of the first reading and the second reading to determine in real-time at least one of levels of red blood cell content, levels of white blood cell content, levels of fibrin, a clot size, a clot shape, and a clot location in the vasculature.

13. The method or use according to clause 1, wherein the determining criteria of the clot comprises:

delivering a catheter to a site of the clot in the vasculature;

taking a first reading of the clot by a using instrumentation for Raman spectroscopy coupled to the catheter at the site of the clot in the vasculature; and generating a spectrum from the first reading, whereby the spectrum relates to at least one of a chemical composition and physical properties of the clot.

14. The method or use according to clause 13, wherein the determining criteria of the clot further comprises: interpreting information contained in the spectrum to determine in real-time at least one of levels of red blood cell content, white blood cell content, levels of fibrin, a clot size, a clot shape, and a clot location in the vasculature.

15. The method or use according to clause 13, further comprising:

taking a second reading of the clot by using the instrumentation for Raman spectroscopy at a second location distal or proximal of the clot and the first location;

generating a spectrum from the second reading, whereby the spectrum of the second reading relates to a chemical composition and/or physical properties of the clot; and interpreting information contained in the spectrum of the first reading and the second reading to determine in real-time at least one of levels of red blood cell content, white blood cell content, levels of fibrin, a clot size, a clot shape, and/or a clot location in the vasculature.

16. The method or use according to clause 1, wherein the treating of the clot comprises retrieving a portion of the clot, the method or use further comprising:

analyzing the retrieved clot and/or one or more fragments of the clot, and selecting a clot treatment step based on analyzing the retrieved clot or analyzing accessing and crossing the clot.

17. The method or use according to clause 1, wherein the determining criteria of the clot comprises:
determining one or more quantitative indications selected from one or more of white blood cell levels, red blood cell levels, serum levels, fibrin levels, clot size, clot location, clot strength, clot elasticity, rate of clot formation or rate of clot lysis.

18. The method or use according to clause 17, further comprising:
comparing the first and the second clot characteristic quantitative indications to correlation data and determining at least one of a selection and order of using one or more techniques selected from aspiration, a first reperfusion device, and/or a second reperfusion device.

19. A system for treating an ischemic event, comprising:
a first reperfusion device for restoring perfusion to an occluded vessel having a clot;
a second reperfusion device for restoring perfusion to the occluded vessel having the clot;
a delivery system for delivering at least one of the first and second reperfusion devices to the clot in the occluded vessel; and
a clot analysis system analyzing the clot of the occluded vessel and determining an individualized treatment protocol using at least one of the first and the second reperfusion devices.

20. The system according to clause 19, wherein the clot analysis system is configured to implement at least one of the following:
determine criteria of the clot;
classify the clot based on the criteria and generate a classification;
determine the individualized treatment protocol for the clot based on the classification, the individualized treatment protocol comprising one or more techniques selected from using at least one of aspirating, restoring perfusion using the first reperfusion device, and restoring perfusion using the second reperfusion device.

21. The system according to clause 20, the clot analysis system further comprises at least one of a computerized tomography (CT) scanning system and a magnetic resonance imaging (MRI) scanning system, and wherein the clot analysis system is configured to analyze information from at least one of a CT scan and a MRI scan to determine physical and/or chemical composition of the clot.

22. The system according to clause 20, wherein the first reperfusion device is a stent retriever configured to remove a clot or portions of a clot that are red blood cell rich;
wherein the second reperfusion device is a pinch retriever configured to remove a clot or portions of a clot that are fibrin-rich; and
wherein if the classification demonstrates that the clot is red blood cell rich, then the individualized treatment protocol comprises passing the first reperfusion device by, through, or about the clot and then retracting the first perfusion device while engaging the clot in a lumen of the first reperfusion device to restore reperfusion to the vessel.

23. The system according to clause 19, wherein the clot analysis system is configured analyze the clot in vivo.

24. The system according to clause 19, wherein the first reperfusion device is a stent retriever and the second reperfusion device is a pinch retriever.

25. A system for treating an ischemic event, comprising:
means for providing in vivo analysis information of a clot of the subject having an ischemic event;
means for providing an indication of an individualized treatment protocol for the subject based upon the analysis information, the individualized treatment comprising one or more techniques selected from using aspiration, restoring perfusion using a first reperfusion device, and/or restoring perfusion using a second reperfusion device; and
means for treating the clot based on the individualized treatment protocol.

26. The system according to clause 25, wherein the first reperfusion device is a stent retriever configured to remove a clot or portions of a clot that are red blood cell rich and the second reperfusion device is a pinch retriever configured to remove a clot or portions of a clot that are fibrin-rich; and
wherein if the indication demonstrates that the clot is red blood cell rich, then the individualized treatment protocol comprises:
means for passing the first reperfusion device by, through, or about the clot and then retracting the first perfusion device while engaging the clot in a lumen of the first reperfusion device to restore reperfusion to the vessel.

27. The system according to clause 25, wherein the first reperfusion device is a stent retriever configured to remove a clot or portions of a clot that are red blood cell rich and the second reperfusion device is a pinch retriever configured to remove a clot or portions of a clot that are fibrin-rich; and
wherein if the classification demonstrates that the clot is fibrin-rich, then the individualized treatment protocol comprises:
means for passing the second reperfusion device by, through, or about the clot and then retracting the second perfusion device while pinching the clot to restore reperfusion to the vessel.

28. A catheter configured for delivery to and analyzing a clot in a blood vessel, the catheter comprising:
a lumen having a proximal end and a distal end; and
a spectroscopic mechanism for analyzing clot composition at a site of the clot in the vasculature.

29. The catheter according to clause 28, wherein the spectroscopic mechanism is configured to emit light capable of penetrating the clot to produce a spectrum that relates to the chemical composition and/or physical properties of one or more portions of the clot exposed to light of the spectroscopic mechanism.

30. The catheter according to clause 29, wherein the spectrum comprises spectral bands that provide indications related to the chemical composition and/or physical properties of one or more portions of the clot.

31. The catheter according to clause 28, wherein the spectroscopic mechanism further comprises:
a fiberoptic bundle extended up to or adjacent the distal end of the catheter; and
a mirror oriented at a predetermined angle adjacent or at the distal end;
wherein light is emitted from the fiberoptic bundle and reflected towards a vessel wall of the vasculature of the clot.

32. The catheter according to clause 31, wherein the predetermined angle is approximately 45°.

33. The catheter according to clause 31, wherein the light is reflected towards the vessel wall from the mirror at approximately 90°.

34. The catheter according to clause 28, wherein the catheter is capable of rotating 360° and taking a 360° scan of the vessel with the clot.

35. The catheter according to clause 28, wherein the spectroscopic mechanism is integrated with the catheter and is configured to emit light capable of penetrating the clot to analyze the clot using near-infrared spectroscopy (NIRS).

36. The catheter according to clause 35, wherein the spectroscopic mechanism comprises a near infrared region of the electromagnetic spectrum (780 to 2500 micrometers).

37. The catheter according to clause 28, wherein the spectroscopic mechanism is integrated with the catheter and is configured to analyze the clot composition using Raman spectroscopy.

38. The catheter according to clause 28, wherein the spectroscopic mechanism is integrated with the catheter and is configured as a visible light diagnostic device that emits light capable of penetrating the clot to analyze the clot composition.

39. A microcatheter for analyzing an ischemic clot in the vasculature, the microcatheter comprising:
a lumen having a proximal end and a distal end; and
a spectroscopic sensing device connected to the distal end, the spectroscopic sensing device configured to measure properties of the clot through the distal end of the microcatheter.

40. The microcatheter according to clause 39, wherein the distal end comprises:
a window portion that is transparent; and
an absorbent portion adjacent the window portion that is opaque.

41. The microcatheter according to clause 40, wherein the window portion is constructed using one or more of Polycarbonate, Poly methylmethacrylate (PMMA), and perfluorinated polymers.

42. The microcatheter according to clause 39, wherein the spectroscopic sensing device comprises a near infrared region of the electromagnetic spectrum (780 to 2500 micrometers).

43. A method or use for managing one or more acute ischemic events, the method or use comprising:
delivering a catheter to a site of a clot in the vasculature, the catheter comprising:
a lumen having a proximal end and a distal end; and
a spectroscopic sensing device connected to the distal end, the spectroscopic sensing device configured to measure properties of the clot through the distal end of the catheter;
taking a first measurement of the clot using the spectroscopic sensing device at a first location of the site of the clot in the vasculature; and
generating a spectrum from the first measurement, whereby the spectrum relates to at least one of a chemical composition and physical properties of the clot.

44. The method or use according to clause 43, the catheter further comprising:
a window portion adjacent the distal end; and
an opaque absorbent portion adjacent the window portion.

45. The method or use according to clause 43, further comprising:
advancing the distal end of the catheter distal of the clot; and then
retracting the distal end of the catheter backwards through the clot while simultaneously spinning the catheter to produce a spectral map over a length of vessel that is occluded by the clot.

46. The method or use according to clause 43, further comprising:
ascertaining one or more physical properties of the clot by measuring different spectral features of the clot based on the spectrum.

47. The method or use according to clause 43, further comprising: interpreting information contained in the spectrum to determine in real-time at least one of levels of red blood cell content, white blood cell content, levels of fibrin, a clot size, a clot shape, and a clot location in the vasculature.

48. The method or use according to clause 43, further comprising:
taking a second measurement of the clot using the spectroscopic sensing device at a second location distal or proximal of the clot and the first location; and
generating a spectrum from the second measurement, whereby the spectrum of the second measurement relates to at least one of a chemical composition and physical properties of the clot.

49. The method or use according to clause 48, wherein the step of taking the first measurement or the second measurement comprises:
emitting light from the spectroscopic sensing device that penetrates the clot at the respective first or second location; and
generating the spectrum that relates to the one of chemical composition and physical properties of the clot exposed to the emitted light of the spectroscopic device.

50. The method or use according to clause 48, further comprising: interpreting information contained spectral bands of the spectrum of the first or second measurement to determine in real-time at least one of levels of red blood cell content, levels of white blood cell content, levels of fibrin, a clot size, a clot shape, and a clot location in the vasculature.

51. The method or use according to clause 43, further comprising: rotating the catheter 360° and scanning inside of the vessel of the clot to generate a 360° scan.

52. The method or use according to clause 43, further comprising: pulling the catheter tip backwards, after being initially placed distal to the thrombus, through an occlusion whilst simultaneously spinning.

53. The method or use according to clause 43, wherein the spectroscopic sensing devices further comprises:
a fiberoptic bundle disposed inside the microcatheter and extended up to or adjacent the distal end of the microcatheter; and
a mirror oriented at a predetermined angle adjacent or at the distal end;
wherein the step of taking the first measurement or the second measurement comprises:
emitting emitted from the fiberoptic bundle; and
reflecting the light towards the clot and/or a vessel wall of the vasculature of the clot.

54. The method or use according to clause 53, wherein the predetermined angle of the mirror is approximately 45°.

55. The method or use according to clause 53, wherein the light is reflected towards the vessel wall from the mirror at approximately 90°.

56. The method or use according to clause 43, wherein the spectroscopic sensing device is integrated with the catheter and is configured to emit light capable of penetrating the clot to analyze the clot using near-infrared spectroscopy.
57. The method or use according to clause 43, wherein the spectroscopic sensing device is integrated with the catheter and is configured to emit light capable of penetrating the clot to analyze the clot using Raman spectroscopy.
58. The method or use according to clause 43, wherein the spectroscopic sensing device is a visible light diagnostic device integrated with the catheter and is configured to emit light capable of penetrating and analyzing the clot.
59. The method or use according to clause 43, further comprising:
classifying the clot based on criteria and generating a classification.
60. The method or use according to clause 59, wherein the step of classifying the clot comprises one or more of a clinical exam, a blood test, a computerized tomography (CT) scan, a magnetic resonance imaging (MRI) scan, a carotid ultrasound, a cerebral angiogram, and an echocardiogram.
61. The method or use according to clause 59, wherein the step of classifying the clot comprises one or more of histological quantification of clot components, mechanical engineering test of the clot
62. The method or use according to clause 43, further comprising: determining criteria of the clot by performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.
63. The method or use according to clause 62, wherein the step of determining criteria of the clot further comprises: interpreting information, by a computing device in operative communication with the clot, about the clot to determine in real-time levels of red blood cell content, white blood cell content, levels of fibrin, a clot size, a clot shape, and/or a clot location in the vasculature; and
wherein the method or use further comprises:
receiving, through a graphical user interface of the computing device, the individualized treatment protocol;
monitoring, by the computing device, perfusion of the vessel with the clot; and,
alerting, by the computing device, in response to perfusion being restored in the vessel.
64. The method or use according to clause 63, wherein the computing device is linked to a database comprising correlation data for interpreting information about the clot and determining the individualized treatment protocol;
wherein the database is remote from the computing device.
65. The method or use according to clause 43, wherein the determining criteria of the clot comprises:
determining one or more quantitative indications selected from one or more of white blood cell levels, red blood cell levels, serum levels, fibrin levels, clot size, clot location, clot strength, clot elasticity, rate of clot formation or rate of clot lysis.
66. The method or use according to clause 65, further comprising:
comparing the first and the second clot characteristic quantitative indications to correlation data and determining at least one of a selection and order of using one or more techniques selected from aspiration, a first reperfusion device, and/or a second reperfusion device.
67. A method or use of calibrating a system for analyzing clots, the method or use comprising:
providing a database of at least one of a chemical composition and physical properties of one or more clots previously scanned using a spectrophotometer;
generating a calibration set of data using the database and a reference analytical method or use; and
correlating the calibration set of data with spectral features of a spectroscopic sensing device of the system for analyzing clots.
68. The method or use according to clause 67, wherein the system for analyzing clots comprises:
a catheter comprising a lumen having a proximal end and a distal end; and
the spectroscopic sensing device connected to the distal end, the spectroscopic sensing device configured to measure properties of the clot through the distal end of the catheter.
69. The method or use according to clause 68, wherein the spectroscopic sensing device is integrated with the catheter and is configured to emit light capable of penetrating the clot to analyze the clot using near-infrared spectroscopy (NIRS).
70. The method or use according to clause 68, wherein the spectroscopic sensing device comprises a near infrared region of the electromagnetic spectrum (780 to 2500 micrometers).
71. The method or use according to clause 68, wherein the spectroscopic sensing device is integrated with the catheter and is configured to analyze the clot composition using Raman spectroscopy.
72. The method or use according to clause 68, wherein the spectroscopic sensing device is integrated with the catheter and is configured as a visible light diagnostic device that emits light capable of penetrating the clot to analyze the clot composition.
73. An endovascular medical system for use with a clot located in a target vessel for managing one or more acute ischemic events, the system comprising:
a guidewire extending in a longitudinal direction from a proximal end to a distal end, the distal end being configured to control its orientation relative to the clot and the target vessel;
wherein the guidewire comprises one or more sensors disposed on or adjacent the distal end, the one or more sensors configured for sensing properties of the clot in vivo and treating the clot based on the sensed properties.
74. The system according to clause 73, wherein the distal end of the guidewire is configured to prevent injury to an inner wall of the target vessel.
75. The system according to clause 73, wherein the one or more sensors are impedance sensors disposed on an outer surface of the guidewire.
76. The system according to clause 73, wherein the one or more sensors are one or more fiberoptic strands or bundles disposed on an outer surface of the guidewire and operable to transmit and collect certain ranges of the electromagnetic spectrum.

77. The system according to clause 73, wherein the distal end of the guidewire is an atraumatic clot-circumventing configured distal end, and wherein the one or more sensors are circumferentially disposed about an outer surface of the guidewire.

78. The system according to clause 73, wherein the distal end of the guidewire is a flattened distal portion having a planar geometric shape and thickness less than an outer diameter of a remaining non-flattened portion.

79. The system according to clause 78, wherein at least one of the one or more sensors is disposed on the flattened distal portion for sensing properties of the clot; and the other of the one or more sensors is disposed on the remaining non-flattened portion for sensing properties of the vessel wall.

80. The system according to clause 78, wherein the flattened distal portion has a paddle geometric shape.

81. The system according to clause 73, wherein the distal end of the guidewire is an atraumatic clot-circumventing configured distal end that is conformable in the lateral direction complementary to a contour of the inner wall of the target vessel when passed between the inner wall of the target vessel and the clot; and when in a compressed state subject to application of an external mechanical force, a widest width in a lateral direction of the distal end of the guidewire is reduceable.

82. The system according to clause 73, further comprising: a microcatheter comprising a proximal end and a distal end, wherein the guidewire is advanceable through the microcatheter, and while in a non-compressed state not subject to application of an external mechanical force, the atraumatic clot-circumventing distal end of the guidewire having the widest width in the lateral direction greater than the inner diameter of the lumen.

83. The system according to clause 73, further comprising: a microcatheter comprising a proximal end and a distal end, wherein the guidewire is advanceable through the microcatheter; and while in a non-compressed state not subject to application of an external mechanical force, the atraumatic clot-circumventing distal end of the guidewire having the widest width in the lateral direction greater than twice the inner diameter of the lumen.

84. A method or use for managing one or more acute ischemic events, the method or use comprising:

delivering a guidewire through a microcatheter to a site of a clot in the vasculature, the guidewire comprising one or more sensors connected to or adjacent a distal portion of the guidewire, the one or more sensors configured to measure properties of the clot in the vasculature;

sensing properties of the clot using the one or more sensors at a first location of the site of the clot in the vasculature; and generating an output from the sensed properties, whereby the output relates to at least one of a chemical composition and physical properties of the clot.

85. The method or use according to clause 84, further comprising: selecting one or more devices and/or procedural steps to treat the clot based on the output.

86. The method or use according to clause 84, wherein the distal portion of the guidewire is an atraumatic clot-circumventing configured distal end, and wherein the one or more sensors are circumferentially disposed or wrapped about an outer surface of the guidewire.

87. The method or use according to clause 84, wherein the distal portion of the guidewire is a flattened distal portion having a planar geometric shape and thickness less than an outer diameter of a remaining non-flattened portion.

88. The method or use according to clause 84, further comprising:

positioning at least one of the one or more sensors on a flattened distal portion for sensing properties of the clot; and positioning the other of the one or more sensors on the remaining non-flattened portion for sensing properties of the vessel wall.

89. The method or use according to clause 84, further comprising:

classifying the clot based on the sensed properties and generating a classification.

90. The method or use according to clause 84, wherein the one or more sensors are near infrared (NIR) sensors disposed on an outer surface of the guidewire.

91. The method or use according to clause 84, wherein the one or more sensors are impedance sensors disposed on an outer surface of the guidewire.

92. The method or use according to clause 84, wherein the one or more sensors are impedance sensors disposed on an outer surface of the guidewire.

93. The method or use according to clause 84, wherein the one or more sensors are Raman spectroscopy sensors disposed on an outer surface of the guidewire and operable to transmit and collect certain ranges of the electromagnetic spectrum.

94. The method or use according to clause 84, wherein the one or more sensors are one or more fiberoptic strands or bundles disposed on an outer surface of the guidewire and operable to transmit and collect certain ranges of the electromagnetic spectrum.

95. The method or use according to clause 84, further comprising:

ascertaining one or more physical properties of the clot by measuring different spectral features of the clot based on the output.

96. The method or use according to clause 84, further comprising: interpreting information contained in the output to determine in real-time at least one of levels of red blood cell content, white blood cell content, platelet content, levels of fibrin, a clot size, a clot shape, a clot density, and a clot location in the vasculature.

97. The method or use according to clause 84, further comprising:

sensing properties of the clot using the one or more sensors at a second location distal or proximal of the clot and the first location; and generating an output from the second location, whereby the output of the second location relates to at least one of a chemical composition and physical properties of the clot.

98. The method or use according to clause 84, further comprising: classifying the clot based on the output and one or more of a clinical exam, a blood test, a computerized tomography (CT) scan, a magnetic resonance imaging (MRI) scan, an ultrasound scan, a cerebral angiogram, and an echocardiogram.

99. The method or use according to clause 84, further comprising: determining criteria of the clot by
performing at least one of a CT scan and an MRI scan; and
analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.
100. The method or use according to clause 84, further comprising:
determining criteria of the clot by:
determining one or more quantitative indications selected from one or more of white blood cell levels, red blood cell levels, serum levels, fibrin levels, clot size, clot location, clot strength, clot elasticity, rate of clot formation or rate of clot lysis.
101. An endovascular medical system for use with a clot located in a target vessel for managing one or more acute ischemic events, the system comprising:
a guidewire extending in a longitudinal direction from a proximal end to a distal end, wherein the guidewire comprises a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot.
102. The system according to clause 101, wherein the one or more sensors are configured to simultaneously measure temperature of a plurality of locations of the clot and target vessel.
103. The system according to clause 101, wherein the sensors are selectively positioned at locations along the distal end to measure regions of the clot.
104. The system according to clause 101, wherein the one or more sensors are each separated a predetermined distance at locations along the distal end to measure regions of the clot.
105. The system according to clause 101, wherein the distal end of the guidewire comprises an expanded perimeter with an atraumatic clot-circumventing configured distal end in a delivery configuration, and wherein the one or more sensors are disposed about the expanded perimeter.
106. The system according to clause 105, wherein the expanded perimeter has an elliptical, curved, or paddle geometric shape.
107. The system according to clause 101, wherein the distal end of the guidewire comprises an expanded perimeter defined by a loop with a void therebetween in a delivery configuration, the loop comprising two elongate sections extended distally and joined at the distal end, and wherein the one or more sensors are disposed about the elongate sections.
108. The system according to clause 107, wherein the loop and the void has an elliptical, curved, or paddle geometric shape.
109. The system according to clause 101, wherein the distal end of the guidewire is conformable in the lateral direction complementary to a contour of the inner wall of the target vessel when passed between the inner wall of the target vessel and the clot; and
when in a compressed state subject to application of an external mechanical force, a widest width in a lateral direction of the distal end of the guidewire is reduceable.
110. A method or use for managing one or more acute ischemic events, the method or use comprising:
delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot;
sensing properties of the clot using at least one of the temperature sensors at a first location distal of the clot, a second location in the clot, and a third location proximal of the clot; and
generating an output from the sensed properties, whereby the output relates to at least one of a chemical composition and physical properties of the clot.
111. The method or use according to clause 110, wherein the step of sensing properties with the temperature sensors is done simultaneously at each location.
112. The method or use according to clause 110, further comprising: selectively positioning the sensors at predetermined locations along the distal end to measure regions of the clot.
113. The method or use according to clause 110, further comprising:
separating each sensor a predetermined distance at locations along the distal end to measure regions of the clot.
114. The method or use according to clause 110, wherein the distal end of the guidewire comprises an expanded perimeter with an atraumatic clot-circumventing configured distal end in a delivery configuration, and wherein the one or more sensors are disposed about the expanded perimeter.
115. The method or use according to clause 110, further comprising: classifying the clot based on the sensed properties and generating a classification.
116. The method or use according to clause 110, further comprising: interpreting information contained in the output to determine in real-time at least one of levels of red blood cell content, white blood cell content, levels of fibrin, a clot size, a clot shape, and a clot location in the vasculature.
117. The method or use according to clause 110, further comprising: classifying the clot based on the output and one or more of a clinical exam, a blood test, a computerized tomography (CT) scan, a magnetic resonance imaging (MRI) scan, a carotid ultrasound, a cerebral angiogram, and an echocardiogram.
118. The method or use according to clause 110, further comprising:
determining criteria of the clot by
performing at least one of a CT scan and an MRI scan; and
analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.
119. A method or use for managing one or more acute ischemic events, the method or use comprising:
delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot;

sensing properties of the clot using the temperature sensors at a plurality of locations in the clot; and generating an output from the sensed properties, whereby the output relates to at least one of a chemical composition and physical properties of the clot.

120. The method or use according to clause 119, further comprising:

sensing properties of the clot at a location distal and/or proximal of the clot.

121. Use for managing one or more acute ischemic events, comprising:

determining criteria of a clot;

classifying the clot based on the criteria and generating a classification;

determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and treating the clot based on the individualized treatment protocol.

122. Use according to clause 121, wherein the classifying the clot is carried out in vivo.

123. Use according to clause 121, wherein the first reperfusion device is a stent retriever and the second reperfusion device is a pinch retriever.

124. Use according to clause 121, wherein the classifying the clot comprises one or more of a clinical exam, a blood test, a computerized tomography (CT) scan, a magnetic resonance imaging (MRI) scan, a carotid ultrasound, a cerebral angiogram, and an echocardiogram.

125. Use according to clause 121, wherein the determining criteria of the clot comprises:

performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

126. Use according to clause 121, wherein the first reperfusion device is a stent retriever configured to remove a clot or portions of a clot that are red blood cell rich and the second reperfusion device is a pinch retriever configured to remove a clot or portions of a clot that are fibrin-rich; and wherein if the classification demonstrates that the clot is red blood cell rich, then the individualized treatment protocol comprises:

passing the first reperfusion device by, through, or about the clot and then retracting the first perfusion device while engaging the clot in a lumen of the first reperfusion device to restore reperfusion to the vessel.

127. Use according to clause 121, wherein the first reperfusion device is a stent retriever configured to remove a clot or portions of a clot that are red blood cell rich and the second reperfusion device is a pinch retriever configured to remove a clot or portions of a clot that are fibrin-rich; and wherein if the classification demonstrates that the clot is fibrin-rich, then the individualized treatment protocol comprises:

passing the second reperfusion device by, through, or about the clot and then retracting the second perfusion device while pinching the clot to restore reperfusion to the vessel.

128. Use according to clause 121, wherein the determining criteria of the clot further comprises: interpreting information, by a computing device in operative communication with the clot, about the clot to determine in real-time levels of red blood cell content, white blood cell content, levels of fibrin, a clot size, a clot shape, and/or a clot location in the vasculature; and wherein the use further comprises:

receiving, through a graphical user interface of the computing device, the individualized treatment protocol;

monitoring, by the computing device, perfusion of the vessel with the clot; and, alerting, by the computing device, in response to perfusion being restored in the vessel.

129. Use according to clause 121, wherein the computing device is linked to a database comprising correlation data for interpreting information about the clot and determining the individualized treatment protocol;

wherein the database is remote from the computing device.

130. Use according to clause 121, wherein the determining criteria of the clot comprises:

delivering a catheter to a site of the clot in the vasculature;

taking a first reading of the clot by a using instrumentation for near infrared spectroscopy (NIR) coupled to the catheter at a first location of the site of the clot in the vasculature; and generating a spectrum from the first reading, whereby the spectrum relates to at least one of a chemical composition and physical properties of the clot.

131. Use according to clause 130, wherein the determining criteria of the clot further comprises: interpreting information contained in the spectrum to determine in real-time at least one of levels of red blood cell content, white blood cell content, levels of fibrin, a clot size, a clot shape, and a clot location in the vasculature.

132. Use according to clause 130, further comprising:

taking a second reading of the clot by using the instrumentation for NIR at a second location distal or proximal of the clot and the first location;

generating a spectrum from the second reading, whereby the spectrum of the second reading relates to at least one of a chemical composition and physical properties of the clot; and interpreting information contained in the spectrum of the first reading and the second reading to determine in real-time at least one of levels of red blood cell content, levels of white blood cell content, levels of fibrin, a clot size, a clot shape, and a clot location in the vasculature.

133. Use according to clause 121, wherein the determining criteria of the clot comprises:

delivering a catheter to a site of the clot in the vasculature;

taking a first reading of the clot by a using instrumentation for Raman spectroscopy coupled to the catheter at the site of the clot in the vasculature; and generating a spectrum from the first reading, whereby the spectrum relates to at least one of a chemical composition and physical properties of the clot.

134. Use according to clause 133, wherein the determining criteria of the clot further comprises: interpreting information contained in the spectrum to determine in real-time at least one of levels of red blood cell content, white blood cell content, levels of fibrin, a clot size, a clot shape, and a clot location in the vasculature.

135. Use according to clause 133, further comprising:
taking a second reading of the clot by using the instrumentation for Raman spectroscopy at a second location distal or proximal of the clot and the first location;
generating a spectrum from the second reading, whereby the spectrum of the second reading relates to a chemical composition and/or physical properties of the clot; and
interpreting information contained in the spectrum of the first reading and the second reading to determine in real-time at least one of levels of red blood cell content, white blood cell content, levels of fibrin, a clot size, a clot shape, and/or a clot location in the vasculature.

136. Use according to clause 121, wherein the treating of the clot comprises retrieving a portion of the clot, further comprising:
analyzing the retrieved clot and/or one or more fragments of the clot, and
selecting a clot treatment step based on analyzing the retrieved clot or analyzing accessing and crossing the clot.

137. Use according to clause 121, wherein the determining criteria of the clot comprises:
determining one or more quantitative indications selected from one or more of white blood cell levels, red blood cell levels, serum levels, fibrin levels, clot size, clot location, clot strength, clot elasticity, rate of clot formation or rate of clot lysis.

138. Use according to clause 137, further comprising:
comparing the first and the second clot characteristic quantitative indications to correlation data and determining at least one of a selection and order of using one or more techniques selected from aspiration, a first reperfusion device, and/or a second reperfusion device.

139. Use of any system of this disclosure for treating an ischemic event, the system comprising:
a first reperfusion device for restoring perfusion to an occluded vessel having a clot;
a second reperfusion device for restoring perfusion to the occluded vessel having the clot;
a delivery system for delivering at least one of the first and second reperfusion devices to the clot in the occluded vessel; and
a clot analysis system analyzing the clot of the occluded vessel and determining an individualized treatment protocol using at least one of the first and the second reperfusion devices.

140. Use of any previous system for treating an ischemic event, the system comprising:
means for providing in vivo analysis information of a clot of the subject having an ischemic event;
means for providing an indication of an individualized treatment protocol for the subject based upon the analysis information, the individualized treatment comprising one or more techniques selected from using aspiration, restoring perfusion using a first reperfusion device, and/or restoring perfusion using a second reperfusion device; and
means for treating the clot based on the individualized treatment protocol.

141. Use of any previous catheter for analyzing a clot in a blood vessel.

142. Use of any previous system for managing one or more acute ischemic events, comprising:
delivering a catheter to a site of a clot in the vasculature, the catheter comprising:
a lumen having a proximal end and a distal end; and
a spectroscopic sensing device connected to the distal end, the spectroscopic sensing device configured to measure properties of the clot through the distal end of the catheter;
taking a first measurement of the clot using the spectroscopic sensing device at a first location of the site of the clot in the vasculature; and
generating a spectrum from the first measurement, whereby the spectrum relates to at least one of a chemical composition and physical properties of the clot.

143. Use according to clause 142, the catheter further comprising:
a window portion adjacent the distal end; and
an opaque absorbent portion adjacent the window portion.

144. Use according to clause 142, further comprising:
advancing the distal end of the catheter distal of the clot; and then
retracting the distal end of the catheter backwards through the clot while simultaneously spinning the catheter to produce a spectral map over a length of vessel that is occluded by the clot.

145. Use according to clause 142, further comprising:
ascertaining one or more physical properties of the clot by measuring different spectral features of the clot based on the spectrum.

146. Use according to clause 142, further comprising:
interpreting information contained in the spectrum to determine in real-time at least one of levels of red blood cell content, white blood cell content, levels of fibrin, a clot size, a clot shape, and a clot location in the vasculature.

147. Use according to clause 142, further comprising:
taking a second measurement of the clot using the spectroscopic sensing device at a second location distal or proximal of the clot and the first location; and
generating a spectrum from the second measurement, whereby the spectrum of the second measurement relates to at least one of a chemical composition and physical properties of the clot.

148. Use according to clause 147, wherein the step of taking the first measurement or the second measurement comprises:
emitting light from the spectroscopic sensing device that penetrates the clot at the respective first or second location; and
generating the spectrum that relates to the one of chemical composition and physical properties of the clot exposed to the emitted light of the spectroscopic device.

149. Use according to clause 147, further comprising:
interpreting information contained spectral bands of the spectrum of the first or second measurement to determine in real-time at least one of levels of red blood cell content, levels of white blood cell content, levels of fibrin, a clot size, a clot shape, and a clot location in the vasculature.

150. Use according to clause 142, further comprising:
rotating the catheter 360° and scanning inside of the vessel of the clot to generate a 360° scan.

151. Use according to clause 142, further comprising: pulling the catheter tip backwards, after being initially placed distal to the thrombus, through an occlusion whilst simultaneously spinning.

152. Use according to clause 142, wherein the spectroscopic sensing devices further comprises:
a fiberoptic bundle disposed inside the microcatheter and extended up to or adjacent the distal end of the microcatheter; and
a mirror oriented at a predetermined angle adjacent or at the distal end;
wherein the step of taking the first measurement or the second measurement comprises:
emitting emitted from the fiberoptic bundle; and
reflecting the light towards the clot and/or a vessel wall of the vasculature of the clot.

153. Use according to clause 152, wherein the predetermined angle of the mirror is approximately 45°.

154. Use according to clause 152, wherein the light is reflected towards the vessel wall from the mirror at approximately 90°.

155. Use according to clause 142, wherein the spectroscopic sensing device is integrated with the catheter and is configured to emit light capable of penetrating the clot to analyze the clot using near-infrared spectroscopy.

156. Use according to clause 142, wherein the spectroscopic sensing device is integrated with the catheter and is configured to emit light capable of penetrating the clot to analyze the clot using Raman spectroscopy.

157. Use according to clause 142, wherein the spectroscopic sensing device is a visible light diagnostic device integrated with the catheter and is configured to emit light capable of penetrating and analyzing the clot.

158. Use according to clause 142, further comprising:
classifying the clot based on criteria and generating a classification.

159. Use according to clause 158, wherein the step of classifying the clot comprises one or more of a clinical exam, a blood test, a computerized tomography (CT) scan, a magnetic resonance imaging (MRI) scan, a carotid ultrasound, a cerebral angiogram, and an echocardiogram.

160. Use according to clause 158, wherein the step of classifying the clot comprises one or more of histological quantification of clot components, mechanical engineering test of the clot 161. Use according to clause 142, further comprising: determining criteria of the clot by performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

162. Use according to clause 161, wherein the step of determining criteria of the clot further comprises: interpreting information, by a computing device in operative communication with the clot, about the clot to determine in real-time levels of red blood cell content, white blood cell content, levels of fibrin, a clot size, a clot shape, and/or a clot location in the vasculature; and wherein the use further comprises:
receiving, through a graphical user interface of the computing device, the individualized treatment protocol;
monitoring, by the computing device, perfusion of the vessel with the clot; and,
alerting, by the computing device, in response to perfusion being restored in the vessel.

163. Use according to clause 162, wherein the computing device is linked to a database comprising correlation data for interpreting information about the clot and determining the individualized treatment protocol; wherein the database is remote from the computing device.

164. Use according to clause 142, wherein the determining criteria of the clot comprises:
determining one or more quantitative indications selected from one or more of white blood cell levels, red blood cell levels, serum levels, fibrin levels, clot size, clot location, clot strength, clot elasticity, rate of clot formation or rate of clot lysis.

165. Use according to clause 164, further comprising:
comparing the first and the second clot characteristic quantitative indications to correlation data and determining at least one of a selection and order of using one or more techniques selected from aspiration, a first reperfusion device, and/or a second reperfusion device.

166. Use of calibrating a system for analyzing clots, comprising:
providing a database of at least one of a chemical composition and physical properties of one or more clots previously scanned using a spectrophotometer,
generating a calibration set of data using the database and a reference analytical method; and
correlating the calibration set of data with spectral features of a spectroscopic sensing device of the system for analyzing clots.

167. Use according to clause 166, wherein the system for analyzing clots comprises:
a catheter comprising a lumen having a proximal end and a distal end; and
the spectroscopic sensing device connected to the distal end, the spectroscopic sensing device configured to measure properties of the clot through the distal end of the catheter.

168. Use according to clause 167, wherein the spectroscopic sensing device is integrated with the catheter and is configured to emit light capable of penetrating the clot to analyze the clot using near-infrared spectroscopy (NIRS).

169. Use according to clause 167, wherein the spectroscopic sensing device comprises a near infrared region of the electromagnetic spectrum (780 to 2500 micrometers).

170. Use according to clause 167, wherein the spectroscopic sensing device is integrated with the catheter and is configured to analyze the clot composition using Raman spectroscopy.

171. Use according to clause 167, wherein the spectroscopic sensing device is integrated with the catheter and is configured as a visible light diagnostic device that emits light capable of penetrating the clot to analyze the clot composition.

172. Use of an endovascular medical system with a clot located in a target vessel for managing one or more acute ischemic events, the system comprising:
a guidewire extending in a longitudinal direction from a proximal end to a distal end, the distal end being configured to control its orientation relative to the clot and the target vessel, wherein the guidewire comprises one or more sensors disposed on or adjacent the distal end, the one or more sensors configured for sensing properties of the clot in vivo and treating the clot based on the sensed properties.

173. Use for managing one or more acute ischemic events, comprising:
delivering a guidewire through a microcatheter to a site of a clot in the vasculature, the guidewire comprising one or more sensors connected to or adjacent a distal portion of the guidewire, the one or more sensors configured to measure properties of the clot in the vasculature;
sensing properties of the clot using the one or more sensors at a first location of the site of the clot in the vasculature; and
generating an output from the sensed properties, whereby the output relates to at least one of a chemical composition and physical properties of the clot.

174. Use according to clause 173, further comprising: selecting one or more devices and/or procedural steps to treat the clot based on the output.

175. Use according to clause 173, wherein the distal portion of the guidewire is an atraumatic clot-circumventing configured distal end, and wherein the one or more sensors are circumferentially disposed or wrapped about an outer surface of the guidewire.

176. Use according to clause 173, wherein the distal portion of the guidewire is a flattened distal portion having a planar geometric shape and thickness less than an outer diameter of a remaining non-flattened portion.

177. Use according to clause 173, further comprising:
positioning at least one of the one or more sensors on a flattened distal portion for sensing properties of the clot; and
positioning the other of the one or more sensors on the remaining non-flattened portion for sensing properties of the vessel wall.

178. Use according to clause 173, further comprising:
classifying the clot based on the sensed properties and generating a classification.

179. Use according to clause 173, wherein the one or more sensors are near infrared (NIR) sensors disposed on an outer surface of the guidewire.

180. Use according to clause 173, wherein the one or more sensors are impedance sensors disposed on an outer surface of the guidewire.

181. Use according to clause 173, wherein the one or more sensors are impedance sensors disposed on an outer surface of the guidewire.

182. Use according to clause 173, wherein the one or more sensors are Raman spectroscopy sensors disposed on an outer surface of the guidewire and operable to transmit and collect certain ranges of the electromagnetic spectrum.

183. Use according to clause 173, wherein the one or more sensors are one or more fiberoptic strands or bundles disposed on an outer surface of the guidewire and operable to transmit and collect certain ranges of the electromagnetic spectrum.

184. Use according to clause 173, further comprising:
ascertaining one or more physical properties of the clot by measuring different spectral features of the clot based on the output.

185. Use according to clause 173, further comprising:
interpreting information contained in the output to determine in real-time at least one of levels of red blood cell content, white blood cell content, platelet content, levels of fibrin, a clot size, a clot shape, a clot density, and a clot location in the vasculature.

186. Use according to clause 173, further comprising:
sensing properties of the clot using the one or more sensors at a second location distal or proximal of the clot and the first location; and
generating an output from the second location, whereby the output of the second location relates to at least one of a chemical composition and physical properties of the clot.

187. Use according to clause 173, further comprising:
classifying the clot based on the output and one or more of a clinical exam, a blood test, a computerized tomography (CT) scan, a magnetic resonance imaging (MRI) scan, an ultrasound scan, a cerebral angiogram, and an echocardiogram.

188. Use according to clause 173, further comprising:
determining criteria of the clot by
performing at least one of a CT scan and an MRI scan; and
analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

189. Use according to clause 173, further comprising:
determining criteria of the clot by
determining one or more quantitative indications selected from one or more of white blood cell levels, red blood cell levels, serum levels, fibrin levels, clot size, clot location, clot strength, clot elasticity, rate of clot formation or rate of clot lysis.

190. Use of an endovascular medical system for use with a clot located in a target vessel for managing one or more acute ischemic events, the system comprising:
a guidewire extending in a longitudinal direction from a proximal end to a distal end, wherein the guidewire comprises a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot.

191. Use for managing one or more acute ischemic events, comprising:
delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot;
sensing properties of the clot using at least one of the temperature sensors at a first location distal of the clot, a second location in the clot, and a third location proximal of the clot; and
generating an output from the sensed properties, whereby the output relates to at least one of a chemical composition and physical properties of the clot.

192. Use according to clause 191, wherein the step of sensing properties with the temperature sensors is done simultaneously at each location.

193. Use according to clause 191, further comprising: selectively positioning the sensors at predetermined locations along the distal end to measure regions of the clot.

194. Use according to clause 191, further comprising: separating each sensor a predetermined distance at locations along the distal end to measure regions of the clot.

195. Use according to clause 191, wherein the distal end of the guidewire comprises an expanded perimeter with an atraumatic clot-circumventing configured distal end in a delivery configuration, and wherein the one or more sensors are disposed about the expanded perimeter.

196. Use according to clause 191, further comprising: classifying the clot based on the sensed properties and generating a classification.

197. Use according to clause 191, further comprising: interpreting information contained in the output to determine in real-time at least one of levels of red blood cell content, white blood cell content, levels of fibrin, a clot size, a clot shape, and a clot location in the vasculature.

198. Use according to clause 191, further comprising: classifying the clot based on the output and one or more of a clinical exam, a blood test, a computerized tomography (CT) scan, a magnetic resonance imaging (MRI) scan, a carotid ultrasound, a cerebral angiogram, and an echocardiogram.

199. Use according to clause 191, further comprising: determining criteria of the clot by performing at least one of a CT scan and an MRI scan; and analyzing information from at least one of the CT scan and the MRI scan to determine physical and/or chemical composition of the clot, including levels of red blood cell content, white blood cell content, levels of fibrin, a clot size, a clot shape, and/or a clot location in the vasculature.

200. Use for managing one or more acute ischemic events, comprising: delivering a guidewire through a microcatheter to a site of a clot in the vasculature, the guidewire extending in a longitudinal direction from a proximal end to a distal end and comprising a plurality of temperature sensors, whereby at least one of temperature sensor is positioned proximal of the distal end and one or more of the other of the sensors are positioned on or adjacent the distal end, the one or more sensors configured for sensing temperature of the clot in vivo and identifying properties of the clot;
sensing properties of the clot using the temperature sensors at a plurality of locations in the clot; and
generating an output from the sensed properties, whereby the output relates to at least one of a chemical composition and physical properties of the clot.

201. Use according to clause 200, further comprising: sensing properties of the clot at a location distal and/or proximal of the clot.

What is claimed is:

1. A method or use for managing one or more acute ischemic events, the method or use comprising:
   determining criteria of a clot;
   classifying the clot based on the criteria and generating a classification;
   determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and
   treating the clot based on the individualized treatment protocol,
   wherein the first reperfusion device is a stent retriever configured to remove a clot or portions of a clot that are red blood cell rich and the second reperfusion device is a pinch retriever configured to remove a clot or portions of a clot that are fibrin-rich;
   wherein the determining criteria of the clot further comprises interpreting information, by a computing device in operative communication with the clot, about the clot to determine in real-time levels of red blood cell content, white blood cell content, levels of fibrin, a clot size, a clot shape, and/or a clot location in the vasculature; and
   wherein the method or use further comprises:
   receiving, through a graphical user interface of the computing device, the individualized treatment protocol;
   monitoring, by the computing device, perfusion of the vessel with the clot; and,
   alerting, by the computing device, in response to perfusion being restored in the vessel.

2. The method or use according to claim 1, wherein the determining criteria of the clot comprises:
   delivering a catheter to a site of the clot in the vasculature;
   taking a first reading of the clot by a using instrumentation for near infrared spectroscopy (NIR) coupled to the catheter at a first location of the site of the clot in the vasculature; and
   generating a spectrum from the first reading, whereby the spectrum relates to at least one of a chemical composition and physical properties of the clot.

3. The method or use according to claim 2, wherein the determining criteria of the clot further comprises: interpreting information contained in the spectrum to determine in real-time at least one of levels of red blood cell content, white blood cell content, levels of fibrin, a clot size, a clot shape, and a clot location in the vasculature.

4. The method or use according to claim 2, further comprising:
   taking a second reading of the clot by using the instrumentation for NIR at a second location distal or proximal of the clot and the first location;
   generating a spectrum from the second reading, whereby the spectrum of the second reading relates to at least one of a chemical composition and physical properties of the clot; and
   interpreting information contained in the spectrum of the first reading and the second reading to determine in real-time at least one of levels of red blood cell content, levels of white blood cell content, levels of fibrin, a clot size, a clot shape, and a clot location in the vasculature.

5. The method or use according to claim 1, wherein the classifying the clot is carried out in vivo.

6. The method or use according to claim 1, wherein if the classification demonstrates that the clot is red blood cell rich, then the individualized treatment protocol comprises: passing the first reperfusion device by, through, or about the clot and then retracting the first perfusion device while engaging the clot in a lumen of the first reperfusion device to restore reperfusion to the vessel.

7. The method or use according to claim 1, wherein if the classification demonstrates that the clot is fibrin-rich, then the individualized treatment protocol comprises passing the second reperfusion device by, through, or about the clot and then retracting the second perfusion device while pinching the clot to restore reperfusion to the vessel.

8. The method or use according to claim 1, wherein the determining criteria of the clot further comprises interpreting information, by a computing device in operative communication with the clot, wherein the computing device is linked to a database comprising correlation data for interpreting information about the clot and determining the individualized treatment protocol;
wherein the database is remote from the computing device.

9. The method or use according to claim 1, wherein the determining criteria of the clot comprises:
delivering a catheter to a site of the clot in the vasculature;
taking a first reading of the clot by a using instrumentation for Raman spectroscopy coupled to the catheter at the site of the clot in the vasculature; and
generating a spectrum from the first reading, whereby the spectrum relates to at least one of a chemical composition and physical properties of the clot.

10. The method or use according to claim 9, wherein the determining criteria of the clot further comprises: interpreting information contained in the spectrum to determine in real-time at least one of levels of red blood cell content, white blood cell content, levels of fibrin, a clot size, a clot shape, and a clot location in the vasculature.

11. The method or use according to claim 9, further comprising:
taking a second reading of the clot by using the instrumentation for Raman spectroscopy at a second location distal or proximal of the clot and the first location;
generating a spectrum from the second reading, whereby the spectrum of the second reading relates to a chemical composition and/or physical properties of the clot; and
interpreting information contained in the spectrum of the first reading and the second reading to determine in real-time at least one of levels of red blood cell content, white blood cell content, levels of fibrin, a clot size, a clot shape, and/or a clot location in the vasculature.

12. The method or use according to claim 1, wherein the treating of the clot comprises retrieving a portion of the clot, the method or use further comprising: analyzing the retrieved clot and/or one or more fragments of the clot; and selecting a clot treatment step based on analyzing the retrieved clot or analyzing accessing and crossing the clot.

13. The method or use according to claim 1, wherein the determining criteria of the clot comprises: determining one or more quantitative indications selected from one or more of white blood cell levels, red blood cell levels, serum levels, fibrin levels, clot size, clot location, clot strength, clot elasticity, rate of clot formation or rate of clot lysis.

14. The method or use according to claim 13, further comprising: comparing a first and a second clot characteristic quantitative indications to correlation data and determining at least one of a selection and order of using one or more techniques selected from aspiration, the first reperfusion device, and/or the second reperfusion device.

15. A method or use for managing one or more acute ischemic events, the method or use comprising:
determining criteria of a clot;
classifying the clot based on the criteria and generating a classification;
determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and
treating the clot based on the individualized treatment protocol,
wherein the first reperfusion device is a stent retriever configured to remove a clot or portions of a clot that are red blood cell rich and the second reperfusion device is a pinch retriever configured to remove a clot or portions of a clot that are fibrin-rich;
wherein the determining criteria of the clot further comprises interpreting information, by a computing device in operative communication with the clot, wherein the computing device is linked to a database comprising correlation data for interpreting information about the clot and determining the individualized treatment protocol;
wherein the database is remote from the computing device.

16. A method or use for managing one or more acute ischemic events, the method or use comprising:
determining criteria of a clot;
classifying the clot based on the criteria and generating a classification;
determining an individualized treatment protocol for the clot based on the classification, the individualized treatment protocol comprising one or more techniques selected from using at least one of aspirating, restoring perfusion using a first reperfusion device, and restoring perfusion using a second reperfusion device; and
treating the clot based on the individualized treatment protocol,
wherein the first reperfusion device is a stent retriever configured to remove a clot or portions of a clot that are red blood cell rich and the second reperfusion device is a pinch retriever configured to remove a clot or portions of a clot that are fibrin-rich;
wherein the determining criteria of the clot comprises:
determining one or more quantitative indications selected from one or more of white blood cell levels, red blood cell levels, serum levels, fibrin levels, clot size, clot location, clot strength, clot elasticity, rate of clot formation or rate of clot lysis;
further comprising: comparing a first and a second clot characteristic quantitative indications to correlation data and determining at least one of a selection and order of using one or more techniques selected from aspiration, the first reperfusion device, and/or the second reperfusion device.

* * * * *